United States Patent [19]

Nakagawa et al.

[11] Patent Number: 5,061,794
[45] Date of Patent: Oct. 29, 1991

[54] CEPHALOSPORIN DERIVATIVES, AND ANTIBACTERIAL AGENTS

[75] Inventors: Susumu Nakagawa; Koji Yamada; Fumio Nakano; Norikazu Otake; Akira Asai; Satoru Kuroyanagi; Yoshiharu Tanaka; Moriaki Ishikawa; Ryosuke Ushijima; Ryuji Mitomo, all of Okazaki, Japan

[73] Assignee: Banyu Pharmaceutical Co., Ltd., Tokyo, Japan

[21] Appl. No.: 377,086

[22] Filed: Jul. 10, 1989

Related U.S. Application Data

[63] Continuation of Ser. No. 38,208, Apr. 14, 1987, abandoned.

[30] Foreign Application Priority Data

Apr. 14, 1986 [JP] Japan ................. 61-084079
May 1, 1986 [JP] Japan ................. 61-099440
Dec. 27, 1986 [JP] Japan ................. 61-309178

[51] Int. Cl.[5] ................ C07D 501/36; A61K 31/545
[52] U.S. Cl. .................... 514/206; 540/227
[58] Field of Search ............ 514/206; 540/227, 225, 540/221

[56] References Cited

U.S. PATENT DOCUMENTS 4,278,793 7/1981 Durckheimer et al. ............ 540/222
4,288,435 9/1981 Kamiya et al. ............ 540/222

OTHER PUBLICATIONS

Takaya et al., Chemical Abstracts, vol. 92, 58792a, (1980).
Takaya et al., Chemical Abstracts, vol. 95, 25092f, (1981).

Primary Examiner—Nicholas S. Rizzo
Attorney, Agent, or Firm—Oblon, Spivak, McClelland, Maier & Neustadt

[57] ABSTRACT

A compound having the formula:

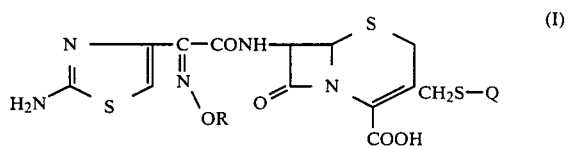

wherein R is a straight chain or branched chain lower alkyl, cyclic lower alkyl, lower alkenyl (except for 1-carboxy-1-vinyl), lower alkynyl, aralkyl, phenyl or 2-pyrrolidon-3-yl group which may be substituted, and Q is

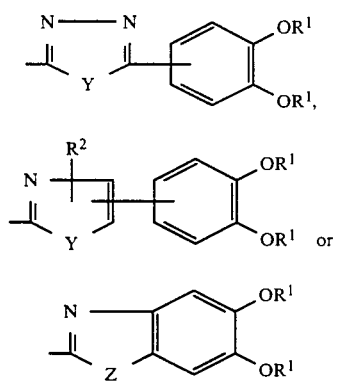

(wherein $R^1$ is a hydrogen atom or an acetyl group, $R^2$ is a hydrogen atom, a carboxyl group or a carboxymethyl group, Y is a sulfur atom or an oxygen atom, Z is a sulfur atom, an oxygen atom or an imino group which may be substituted by a lower alkyl group); or a pharmaceutically acceptable salt, physiologically hydrolyzable ester or solvate thereof.

8 Claims, No Drawings

CEPHALOSPORIN DERIVATIVES, AND ANTIBACTERIAL AGENTS

This is a continuation of application Ser. No. 07/038,208, filed on Apr. 14, 1987, now abandoned.

The present invention relates to novel cephalosporin derivatives, processes for their preparation and antibacterial agents containing them as active ingredients.

A number of cephalosporin compounds have been synthesized which have a 2-(2-aminothiazol-4-yl)-2-substituted oxyiminoacetamido group at the 7-position of the cephem nucleus. As publications which disclose such compounds, Japanese Unexamined Patent Publications No. 102293/1977, No. 116492/1977, No. 137988/1978, No. 9296/1979, No. 154786/1979, No. 157596/1979, No. 154980/1980, No. 86187/1981, No. 59895/1982, No. 99592/1982, No. 192394/1982 and No. 174387/1983, may be mentioned. It is disclosed that such compounds exhibit antibacterial activities against Gram-positive bacteria and cephalosporin resistant Gram-negative bacteria including Pseudomonas aeruginosa thus suggesting that they have excellent antibacterial activities and a broad antibacterial spectrum.

However, they do not have sufficient antibacterial activities against glucose non-fermentative Gram-negative rods such as Pseudomonas aeruginosa, Pseudomonas cepacia, Pseudomonas maltophilia and Acinetobacter calcoaceticus.

Further, a member of cephalosporin compounds have been synthesized which have a 2-(2-aminothiazol-4-yl)-2-substituted oxyiminoacetamido group at the 7-position of the cephem nucleus and an aromatic heterocyclic thiomethyl group at the 3-position of the cephem nucleus. As publications which disclose such compounds, Japanese Unexamined Patent Publications No. 149296/1976, No. 116492/1977, No. 34795/1978, No. 9296/1979, No. 44695/1979, No. 128391/1984,. No. 167576/1984 and No. 41682/1985, may be mentioned. Among such publications, only Japanese Unexamined Patent Publication No. 9296/1979 discloses a cephalosporin derivative having an unsubstituted or substituted phenyl-substituted heterocyclic thiomethyl group at the 3-position of the cephem nucleus. This publication suggests as the substituent at the 3-position of the cephem nucleus, a methyl group having a nucleophilic residue and the like, such as a heterocyclic thiomethyl group which may be substituted, and exemplifies, as the heterocyclic group, thiazolyl, oxazolyl, thiadiazolyl, oxadiazolyl, etc. Further, the publication generally and widely discloses that the heterocyclic thiomethyl group may be substituted by an aryl group such as phenyl, which may have one or more substitutes. As the aryl group, an unsubstituted or substituted phenyl group is suggested, and many substituents are disclosed in general. However, so far as the phenyl-substituted heterocyclic thiomethyl derivative is concerned, only unsubstituted or monosubstituted phenyl substituted heterocyclic thiomethyl derivatives are exemplified and synthesized (Examples 24, 40, 41, 187 and 199 of Japanese Unexamined Patent Publication No. 9296/1979). No data of the compounds against antibacterial activities are disclosed. Particularly, with respect to cephalosporin derivatives which have a 2,3- or 3,4-disubstituted phenyl-substituted heterocyclic thiomethyl group having adjacent two hydroxyl or acetoxy groups in the phenyl nucleus, there is no disclosure or suggestion of such derivatives, not to mention their synthesis in the publication.

Moreover, a number of compounds have been synthesized which have a benzene ring-fused heterocyclic thiomethyl group at the 3-position of the cephem nucleus. A publications which disclose such compounds, Japanese Unexamined Patent Publications No. 125190/1977, No. 9296/1979, No. 117493/1979, No. 19267/1980 and No. 35096/1980, may be mentioned. Japanese Unexamined Patent Publication No. 125190/1977 discloses compounds having a heterocyclic thiomethyl group such as a benzimidazolyl, benzoxazolyl or benzthiazolyl group which may be substituted, at the 3-position of the cephem nucleus, but these compounds are not synthesized at all. Further, there is no suggestion that the heterocyclic thiomethyl group have a hydroxyl group as the substituent at all. Japanese Unexamined Patent Publication No. 9296/1979 discloses as the substituent at the 3-position of the cephem nucleus, a methyl group having a nucleophilic residue, etc. e.g a benzene ring-fused heterocyclic thiomethyl group, which may be substituted, and exemplifies as the benzene ring-fused heterocyclic group, a benzothiazolyl, benzoxazolyl, benzimidazolyl or indolyl group. Further, the publication widely and generally discloses that the heterocyclic thiomethyl group can be substituted by one or more substituents However, the publication suggests only that the benzene ring of the benzene ring-fused heterocyclic thiomethyl group is unsubstituted or monosubstituted, and such compounds are synthesized (Examples 58, 91, 133, 176, 184, 185, 190 and 202 of Japanese Unexamined Patent Publication No. 9296/1979). No data of the compounds against antibacterial activities are disclosed. Particularly, the publication neither discloses nor suggests a cephalosporin derivative having two adjacent hydroxyl groups or acetoxy groups in the benzene ring of the benzene ring fused heterocyclic thiomethyl group, not to mention their synthesis. Japanese Unexamined Patent Publication No. 117493/1979 discloses a cephalosporin derivative having a thiadiazolylthiomethyl or triazolylthiomethyl, benzothiazolylthiomethyl group substituted by an alkyl group having from 3 to 6 carbon atoms, but only a cephalosporin derivative having an unsubstituted benzothiazolylthiomethyl group is synthesized (Example 11(66) of Japanese Unexamined Patent Publication No. 117493/1979). There is no disclosure of a hydroxyl group for the substituent. Japanese Unexamined Patent Publication 19267/1980 discloses a cephalosporin derivative having a heterocyclic thiomethyl group which may be substituted at the 3-position of the cephem nucleus, but does not suggest a hydroxyl group as the substituent. An unsubstituted benzimidazolylthiomethyl group is synthesized (Examples 10(10), 11 and 16(14) of the Japanese Unexamined Patent Publication No. 19267/1980). Japanese Unexamined Patent Publication No. 35096/1980 merely refers to a heterocyclic thiomethyl group which may be substituted by a lower alkyl group at the 3-position of the cephem nucleus.

β-Lactam antibiotics exhibit selective toxicity against bacteria only and present no substantial effects against animal cells, and they have been widely used for the treatment of infectious diseases caused by bacteria as antibiotics having no substantial side effects. Thus, they are highly useful drugs.

However, in recent years, glucose non-fermentative Gram-negative rods, particularly Pseudomonas aeruginosa, have been frequently isolated from immuno-compromised patients, as causative organisms of refractory infections.

Therefore, it has been desired to develop an antimicrobial agent having an improved activity against such bacteria.

It is an object of the present invention to provide novel cephalosporin derivatives having excellent antibacterial activities.

An extensive research was conducted for novel cephalosporin derivatives having a substituted phenyl-substituted heterocyclic thiomethyl group or substituted benzene ring-fused heterocyclic thiomethyl group at the 3-position of the cephem nucleus and 2-(2-aminothiazol-4-yl)-2-substituted oxyiminoacetamido group at the 7-position of the cephem nucleus. As the result, cephalosporin derivatives which have a disubstituted phenyl-substituted heterocyclic thiomethyl group or benzene ring fused heterocyclic thiomethyl group having adjacent two hydroxyl groups or acetoxy groups. These derivatives are novel compounds undisclosed in any literature, and have excellent antibacterial activities against Gram-positive bacteria and Gram-negative bacteria. Particularly, they have strong antibacterial activities against glucose non-fermentative Gram-negative rods, such as Pseudomonas aeruginosa, Pseudomonas cepacia and Acinetobacter calcoaceticus, and they have excellent stability against β-lactamase and they have low β-lactamase inducibility. The present invention has been accomplished on the basis of these discoveries. The cephalosporin derivatives of the present invention have strong activities resistant Gram-negative bacteria, particularly glucose non-fermentative Gram-negative rods including Pseudomonas aeruginosa, and excellent stability against β-lactamase.

The present invention provides a compound having the formula:

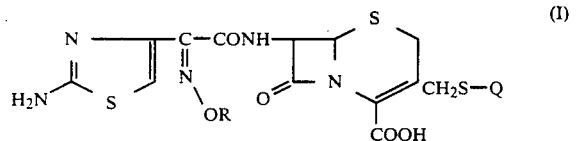

wherein R is a straight chain or branched chain lower alkyl, cyclic lower alkyl, lower alkenyl (except for 1-carboxy-1-vinyl), lower alkynyl, aralkyl, phenyl or 2-pyrrolidon-3-yl group which may be substituted, and Q is

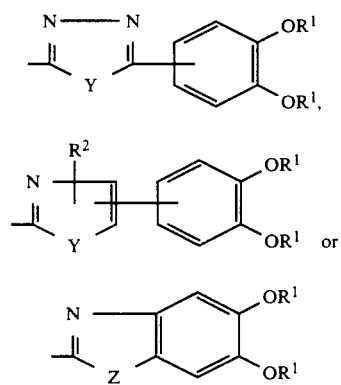

(wherein $R^1$ is a hydrogen atom or an acetyl group, $R^2$ is a hydrogen atom, a carboxyl group or a carboxymethyl group, Y is a sulfur atom or an oxygen atom, Z is a sulfur atom, an oxygen atom or an imino group which may be substituted by a lower alkyl group); or a pharmaceutically acceptable salt, physiologically hydrolyzable ester or solvate thereof Further, the present invention provides a process for preparing the compound of the formula I, or a pharmaceutically acceptable salt, physiologically hydrolyzable ester or solvate thereof, comprising reacting a compound having the formula:

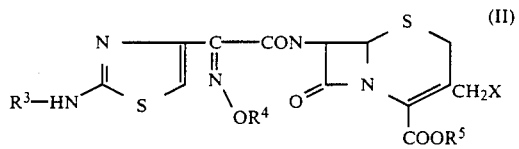

wherein $R^3$ is a hydrogen atom or an amino-protecting group, $R^4$ is a straight chain or branched chain lower alkyl, cyclic lower alkyl, lower alkenyl, lower alkynyl, aralkyl, phenyl or 2-pyrrolidon-3-yl group which may be substituted (provided that the substituent of $R^4$ is optionally protected), X is a leaving group, and $R^5$ is a hydrogen atom or a carboxyl-protecting group or a salt thereof, with a compound having the formula:

$$HS-Q^1 \qquad (III)$$

wherein $Q^1$ is

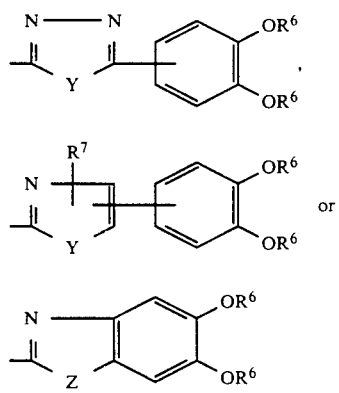

(wherein $R^6$ is a hydrogen atom or a hydroxyl-protecting group, $R^7$ is a hydrogen atom, a carboxyl group or a carboxymethyl group which is optionally protected, Y is a sulfur atom or an oxygen atom and Z is a sulfur atom, an oxygen atom or an imino group which may be substituted by a lower alkyl group), or a salt thereof, to form a compound having the formula:

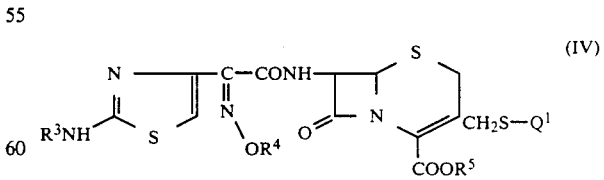

wherein $R^3$, $R^4$, $R^5$ and $Q^1$ are as defined above, and optionally removing the protecting groups.

Another process of the preparation of the compound of the formula I, or a pharmaceutically acceptable salt, physiologically hydrolyzable ester or solvate thereof, comprises acylating a compound having the formula:

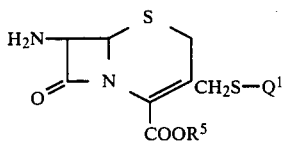

wherein $R^5$ is a hydrogen atom or a carboxyl-protecting group, and $Q^1$ is

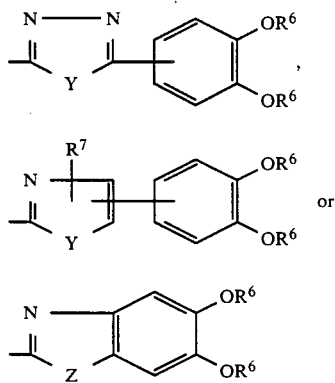

(wherein $R^6$ is a hydrogen atom or a hydroxyl-protecting group, $R^7$ is a hydrogen atom, a carboxyl group or a carboxymehtyl group which is optionally protected, Y is a sulfur atom or an oxygen atom and Z is a sulfur atom, an oxygen atom or an imino group which may be substituted by a lower alkyl group), or a salt thereof, with a carboxylic acid having the formula:

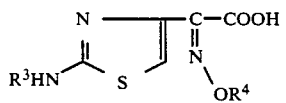

wherein $R^3$ is a hydrogen atom or an amino-protecting group, $R^4$ is a straight chain or branched chain lower alkyl, cyclic lower alkyl, lower alkenyl, lower alkynyl, aralkyl, phenyl or 2-pyrrolidon-3-yl group which may be substituted (provided that the substituent of $R^4$ is optionally protected), or a reactive derivative thereof, to form a compound having the formula:

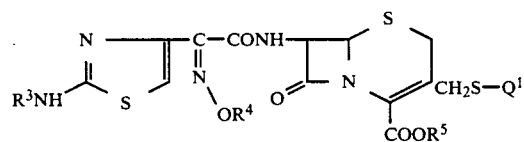

wherein $R^3$, $R^4$, $R^5$ and $Q^1$ are as defined above, and optionally removing the protecting groups.

The present invention also provides an antibacterial agent comprising an antibacterially effective amount of the compound of the formula I and a pharmaceutically acceptable carrier.

Now, the symbols and terms used in the present specification will be explained.

R in the compound of the formula I represents a straight chain or branched chain lower alkyl, lower alkenyl (except for 1-carboxy-1-vinyl), lower alkynyl, cyclic lower alkyl, aralkyl, phenyl or 2-pyrrolidon-3-yl group which may be substituted.

When R is substituted, R may have one or more substituents which may be the same or different, selected from the group consisting of alkyl having from 1 to 4 carbon atoms, hydroxyl, alkoxy having from 1 to 4 carbon atoms, acetoxy, carboxyl, carbamoyl, carboxymethyl, sulfo, sulfomethyl, substituted phenyl, and halogen such as florine, chlorine or bromine.

The straight chain or branched chain lower alkyl group which may be substituted is a straight chain or branched chain alkyl group having from 1 to 6 carbon atoms. Specifically, there may be mentioned methyl, ethyl, n-propyl, isopropyl, n-butyl, isobutyl, sec-butyl, tert-butyl, n-pentyl, n-hexyl, difluoromethyl, 2-fluoroethyl, 2,2-difluoroethyl, 2,2,2-trifluoroethyl, carboxymethyl, 1-carboxyethyl, 2-carboxyethyl or 1-carboxy-1-methylethyl.

The cyclic lower alkyl group which may be substituted is a cyclic alkyl group having from 3 to 6 carbon atoms. Specifically, there may be mentioned cyclopropyl, cyclobutyl, cyclopentyl, cyclohexyl, 1-carboxycyclopropyl, 1-carboxycyclobutyl or 1-carboxycyclopentyl.

The alkenyl group which may be substituted (except for 1-carboxy-1-vinyl) is an alkenyl group having from 2 to 6 carbon atoms. In the case where it has a benzene ring as the substituent, it is a substituted alkenyl group having at least 6 carbon atoms. Specifically, there may be mentioned vinyl, 1-propenyl, isopropenyl, 2-methyl-1-propenyl, 1,3-butadienyl, allyl, 1,1-dimethylallyl, 2-butenyl, 3-butenyl, 3-methyl-2-butenyl, 2-carboxy-1-vinyl, 1-carboxy-1-propenyl, 2-carboxy-1-propenyl, 3-carboxy-1-propenyl, 1-carboxy-2-methyl-1-propenyl, 1-carboxyallyl, 2-carboxyallyl, 3-carboxyallyl, 1-carboxy-3-butenyl, 1-carboxy-3-methyl-2-butenyl, α-carboxystyryl, δ-carboxystyryl, styryl, 1-(substituted phenyl)vinyl or 2-carboxy-1-(substituted phenyl)vinyl, provided that the phenyl can have one or more substituents which may be the same or different, selected from the group consisting of hydroxyl, acetoxy, methoxy, carboxyl, carbamcyl, carboxymethyl, sulfo, sulfomethyl and halogen such as fluorine, chlorine or romine. Particularly preferred is vinyl, isopropenyl, 2-methyl-1-propenyl, allyl, 1,1-dimethylallyl, 1-carboxy-2-methyl-1-propenyl, 2-carboxyallyl, styryl or α-caboxystyryl.

The lower alkynyl group which may be substituted is an alkynyl group having from 2 to 6 carbon atoms. Specifically, there may be mentioned ethynyl, 1-propynyl, 2-propynyl, 1,1-dimethylpropynyl, 2-carboxyethynyl, 1-carboxypropynyl or 3-carboxy-1,1.dimethylpropynyl.

As the phenyl group which may be substituted, there may be mentioned phenyl, 2-hydroxyphenyl, 3-hydroxyphenyl, 4-hydroxyphenyl, 2-acetoxyphenyl, 3-acetoxyphenyl, 4-acetoxyphenyl, 2-chlorophenyl, 3-chlorophenyl, 3-carboxyphenyl, 4-carboxyphenyl, 3,4-dihydroxyphenyl or 3,4-diacetoxyphenyl.

As the aralkyl group which may be substituted, there may be mentioned benzyl, 3-hydroxybenzyl, 4-hydroxybenzyl, 3-acetoxybenzyl, 4-acetoxybenzyl, 2-carboxybenzyl, 3-carboxybenzyl, 4-carboxybenzyl, 2-carboxymethylbenzyl, 3-carboxymethylbenzyl, 4-carboxymethylbenzyl, 2-sulfobenzyl, 3-sulfobenzyl, 4-sulfobenzyl, 2-sulfomethylbenzyl, 3-sulfomethylbenzyl, 4-sulfomethylbenzyl, 3-carboxy-4-hydroxybenzyl, 3,4-dihydroxybenzyl, 3,4-diacetoxybenzyl, α-carboxybenzyl, α-carboxy-3-hydroxybenzyl, α-carboxy-4-hydroxybenzyl, α-carboxy-3-acetoxybenzyl, α-carboxy-4-acetoxybenzyl, α-carboxy-3,4-dihydroxybenzyl or α-carboxy-3,4-diacetoxybenzyl.

Q represents the formula:

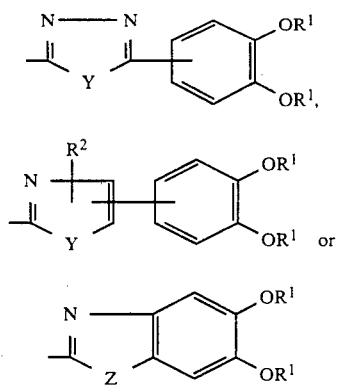

wherein $R^1$ is a hydrogen atom or an acetyl group, $R^2$ is a hydrogen atom, a carboxyl group or a carboxymethyl group, Y is a sulfur atom or an oxygen atom, Z is a sulfur atom, an oxygen atom or an imino group which may be substituted by a lower alkyl group. Namely, Q represents a disubstituted phenyl-substituted heterocyclic thiomethyl and disubstituted benzene ring-fused heterocyclic thiomethyl group having adjacent two hydroxyl or acetoxy groups, wherein the heterocyclic thiomethyl group may have a carboxy group or a carboxymethyl group.

As the disubstituted phenyl group, there may be mentioned 2,3-dihydroxyphenyl, 3,4-dihydroxyphenyl, 2,3-diacetoxyphenyl or 3,4-diacetoxyphenyl. Particularly preferred is 3,4-dihydroxyphenyl or 3,4-diacetoxyphenyl.

As the disubstituted phenyl substituted heterocyclic group, there may be mentioned 5-(disubstituted phenyl)-1,3,4-oxadiazol-2-yl, 5-(disubstituted phenyl)1,3,4-thiadiazol-2-yl, 4-(disubstituted phenyl)thiazol-2-yl, 4-(disubstituted phenyl)-5-carboxythiazol-2-yl, 4-(disubstituted phenyl)-5-carboxymethylthiazol-2-yl, 5-(disubstituted phenyl)-4-carboxythiazol-2-yl, 5-(disubstituted phenyl)-4-carboxymethylthiazol-2-yl, 4-(disubstituted phenyl)oxazol-2-yl, 4-(disubstituted phenyl)-5-carboxyoxazol-2-yl, 4-(disubstituted phenyl)-5-carboxymethyloxazol-2-yl, 5-(disubstituted phenyl)oxazol-2-yl, 5-(disubstituted phenyl)-4-carboxyoxazol-2-yl, 5-(disubstituted phenyl)-4-carboxymethyloxazol-2-yl. Particularly preferred is 5-(dihydroxyphenyl)-1,3,4-oxadiazol-2-yl, 5-(diacetoxyphenyl)-1,3,4-oxadiazol-2-yl, 5-(dihydroxyphenyl)-1,3,4-thiadiazol-2-yl, 5-(diacetoxyphenyl)-1,3,4-thiadiazol-2-yl, 4-(dihydroxyphenyl)thiazol-2-yl, 4-(diacetoxyphenyl)thiazol-2-yl, 4-(dihydroxyphenyl)-5-carboxymethylthiazol-2-yl, 4-(diacetoxyphenyl)-5-carboxymethylthiazol-2-yl, 5-(dihydroxyphenyl)-4-carboxythiazol-2-yl, 5-(diacetoxyphenyl)-4-carboxythiazol-2-yl, 5-(dihydroxyphenyl)oxazol-2-yl or 5-(diacetoxyphenyl)oxazol-2-yl.

As the disubstituted benzene ring-fused heterocyclic group there may be mentioned 5,6-disubstituted benzimidazol-2-yl, 5,6-disubstituted-1-methyl-benzimidazole-2-yl, 5, 6-disubstituted benzoxazol-2-yl or 5,6-disubstituted benzothiazol-2-yl.

The starting compound having the formula:

$$HS-Q^1 \qquad (III)$$

wherein $Q^1$ is

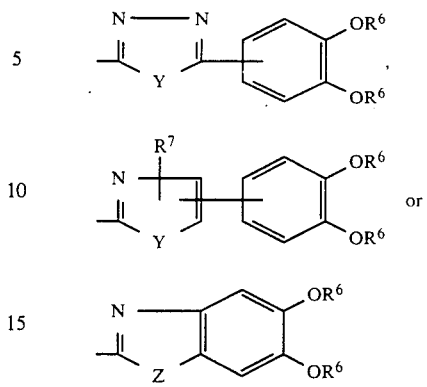

(wherein $R^6$ is a hydrogen atom or a hydroxyl-protecting group, $R^7$ is a hydrogen atom, a carboxyl group or a carboxymethyl group which is optionally protected, Y is a sulfur atom or an oxygen atom and Z is a sulfur atom, an oxygen atom or an imino group which may be substituted by a lower alkyl group), is a new compound not disclosed in any literature, and no cephalosporin derivative having disubstituted phenyl-substituted heterocyclic thiomethyl group or a disubstituted benzene ring-fused heterocyclic thiomethyl group at the 3-position of the cephem nucleus has been synthesized.

Further, the moiety

in the oxyimino group in the formula I, includes a syn-isomer (Z configuration:

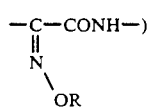

and an anti-isomer (E configuration:

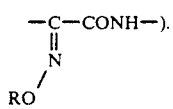

Generally, the syn-isomer (Z configuration) exhibits superior antibacterial activities. In this specification, the OR group represents the syn-isomer (Z configuration) in all cases. The nomenclature for E and Z configurations is given in Journal of the American Chemical Society, Vol. 90, p 509 (1968).

The compounds of the formula I may be converted to non-toxic salts or physiologically hydrolyzable non-toxic esters thereof by usual methods. The non-toxic salts of the compounds of the formula I mean pharmaceutically acceptable usual salts, i.e. salts at the carboxyl group of the 4-position of the cephem nucleus, at the 2-aminothiazole group at the 7-position of the cephem nucleus, or at the acidic residue such as a carboxyl group or a sulfo group or a basic residue such as amino group, as the substituent of Q and/or R.

As the addition salt with a base, there may be mentioned a salt of an alkali metal such as sodium or potassium, a salt of an alkaline earth methal such as calcium or magnesium, an ammonium salt, a salt of an organic amine such as trimetylamine, triethylamine, dicyclohexylamine, N,N'-dibenzylethylenediamine, ethanolamine, diethanolamine, triethanolamine, procaine, pyridine, picoline, quinoline or isoquinoline, or a salt of a basic amino acid such as arginine or lysine, may be mentioned. As the addition salt with an acid, a salt of an inorganic acid such as hydrochloric acid, hydrobromic acid, sulfuric acid, nitric acid, phosphoric acid, carbonic acid, hydrogencarbonic acid or perchloric acid, a salt of an organic acid such as acetic acid, propionic acid, lactic acid, maleic acid, fumaric acid, tartaric acid, malic acid or citric acid, a salt of a sulfonic acid such as methanesulfonic acid, isethionic acid, benzene sulfonic acid or p-toluenesulfonic acid, or a salt of an amino acid such as aspartic acid or glutamic acid, may be mentioned.

The non-toxic esters of the compounds of the formula I mean pharmaceutically acceptable usual esters at the carboxyl groups at the 4-position of the cephem nucleus. For instance, an alkanoyloxymethyl group such as an acetoxymethyl group or a pivaloyloxymethyl group, an alkoxycarbonyloxyalkyl group such as a 1-(ethoxycarbonyloxy)ethyl group, a phthalidyl group, and a (5-substituted-2-oxo-1,3-dioxol-4-yl)methyl group such as a (5-methyl-2-oxo-1,3-dioxol-4-yl)methyl group, may be mentioned.

The preferred examples of the compound of the formula I are as follows:

(1) 7β-[2-(2-aminothiazol-4-yl)-2-methoxyiminoacetamido]-3-[5-(3, 4-dihydroxyphenyl)-1,3,4-oxadiazol-2-yl]thiomethyl-3-cephem-4-carboxylic acid (2) 3-[5-(3,4-diacetoxyphenyl)-1,3,4-oxadiazol-2-yl]-thiomethyl-7 β-[2-(2-aminothiazol-4-yl)-2-methoxyiminoacetamido]-3-cephem-4-carboxylic acid (3) 7β-[2-(2-aminothiazol-4-yl)-2-ethoxyiminoacetamido]3-[5-(3, 4-dihydroxyphenyl)-1,3,4-oxadiazol-2-yl]thiomethyl-3-cephem-4-carboxylic acid (4) 3-[5-(3,4-diacetoxyphenyl)-1,3,4-oxadiazol-2-yl]thiomethyl-7β-[2-(2-aminothiazol-4-yl)-2-ethoxyiminoacetamido]-3-cephem-4-carboxylic acid (5) 7β-[2-(2-aminothiazol-4)-2-isopropoxyiminoacetamido]-3-[5-(3, 4dihydroxyphenyl)-1,3,4-oxadiazol- 2-yl]thiomethyl-3-cephem-4-carboxylic acid (6) 7β-[2-allyloxyimino-2-(2-aminothiazol-4-yl)acetamido]-3-[5-(3, 4-dihydroxyphenyl)-1,3,4-oxadiazol-2-yl]thiomethyl-3-cephem-4-carboxylic acid (7) 7β[2-(2-aminothiazol-4-yl)-2-propargyloxyiminoacetamido]-3-[5-(3, 4-dihydroxyphenyl)-1,3,4-oxadiazol-2-yl]thiomethyl-3-cephem-4-carboxylic acid (8) 7β-[2-(2-aminothiazol-4-yl)-2-carboxymethoxyiminoacetamido]-3-[5-(3, 4-dihydroxyphenyl)-1,3,4-oxadiazol-2-yl]thiomethyl-3-cephem-4-carboxylic acid (9) 7β-[2-(2-aminothiazol-4-yl)-2-(1-carboxy-1-methylethoxyimino) acetamido]-3-[5-3,4-dihydroxyphenyl)1-1,3, 4-oxadiazol-2-yl]thiomethyl-3-cephem-4-carboxylic acid

(10) 7β-[2-(2-aminothiazol-4-yl]-2-(1-carboxy-1-cyclopropoxyimino) acetamido]-3-[5-(3,4-dihydroxyphenyl)1,3, 4-oxadiazol-2-yl]thiomethyl-3-cephem-4-carboxylic acid

(11) 7β-[2-(2-aminothiazol-4-yl)-2-benzyloxyiminoacetamido]-3-[5-(3, 4-dihydroxyphenyl)-1,3,4-oxadiazol-2-yl]thiomethyl-3-cephem-4-carboxylic acid

(12) 7β-[2-(2-aminothiazol-4-yl)-2-(3,4-dihydroxybenzyloxyimino) acetamido]-3-[3-[5-3,4-dihydroxyphenyl)-1,3, 4-oxadiazol-2-yl]thiomethyl-3-cephem-4-carboxylic acid

(13) 7β-[2-(2-aminothiazol-4)-2-(α-carboxybenzyloxymino) acetamido]-3-[5-(3,4-dihydroxyphenyl)-1,3, 4-oxadiazol-2-yl]thiomethyl-3-cephem-4-carboxylic acid

(14) 7β-[2-(2-aminothiazol-4-yl)-2-(α-carboxy-3,4dihydroxybenzyloxyimino) acetamido]-3-[5-(3,4-dihydroxyphenyl)-1, 3,4-oxadiazol-2-yl]thiomethyl-3-cephem-4-carboxylic acid

(15) 7β[2-(2-aminothiazol-4-hydroxybenzyloxyimino) acetamido]-3-[5-(3,4-dihydroxyphenyl)-1,3, 4-oxadiazol-2-yl]thiomethyl-3-cephem-4carboxylic acid

(16) 7β-[2-(2-aminothiazol-4-yl)-2-(3-carboxy-4-hydroxybenzyloxyimino) acetamido]-3-[5-(3,4-dihydroxyphenyl)-1, 3,4-oxadiazol-2-yl]thiomethyl-3-cephem-4-carboxylic acid

(17) 7β-[2-(2-aminothiazol-4-yl)-2-(4-carboxybenzyloxyimino) acetamido]-3-[5-(3,4-dihydroxyphenyl)-1,3, 4-oxadiazol-2-yl]thiomethyl-3-cephem-4-carboxylic acid

(18) 7β-[2-(2-aminothiazol-4-yl)-2-(3-carboxybenzyloxyimino) acetamido]-3-[5-(3,4-dihydroxyphenyl)-1,3, 4-oxadiazol-2-yl]thiomethyl-3-cephem-4carboxylic acid

(19) 7β-[2-(2-aminothiazol-4-yl)-2-(4-carboxylmethylbenzyloxyimino) acetamido]-3-[5-(3,4-dihydroxyphenyl)-1,3, 4-oxadiazol-2-yl]thiomethyl-3-cephem-4-carboxylic acid

(20) 7β-[2-(2-aminothiazol-4-yl)-2-phenoxyiminoacetamido]3-]5-(3, 4-dihydroxyphenyl)-1,3,4-oxadiazol-2-yl]thiomethyl-3-cephem4-carboxylic acid

(21) 7β-[2-(2-aminothiazol-4-yl)-2-(2-carboxymethylbenzyloxyimino) acetamido]-3-[5-(3,4-dihydroxyphenyl)-1,3, 4-oxadiazol-2-yl]thiomethyl-3-cephem-4-carboxylic acid

(22) 7β-[2-(2-aminothiazol-4-yl)-2-(α-carboxybenzyloxyimino) acetamido]-3-[5-(3,4-dihydroxyphenyl)-1,3, 4-oxadiazol-2-yl]thiomethyl-3-cephem-4carboxylic acid

(23) 7β-[2-(2-aminothiazol-4-yl)-2-methoxyiminoacetamido]-3-[5-(3, 4-dihydroxyphenyl)-1,3,4-thiadiazol-2-yl]thiomethyl-3-cephem-4-carboxylic acid

(24) 3-[5-(3,4-diacetoxyphenyl)-1,3,4-thiadiazol-2-yl]thiomethyl-7β-[2-(2-aminothiazol-4-yl)-2-methoxyiminoacetamido]-3-cephem-4-carboxylic acid

(25) 7β-[2-(2-aminothiazol-4-yl)-2-methoxyiminoacetamido]-3-[5-(3, 4-dihydroxyphenyl)-1,3,4-thiadiazol-2-yl]thiomethyl-3-cephem-4-carboxylic acid

(26) 3-[5-(3,4-diacetoxyphenyl)-1,3,4-thiadiazol-2-yl]-thiomethyl-7β-[2-(2-aminothiazol-4-yl)-2-ethoxyiminoacetamido]-3-cephem-4-carboxylic acid

(27) 7β-[2-(2-aminothiazol-4-yl)-2-isopropoxyiminoacetamido]-3-[5-(3, 4-dihydroxyphenyl)-1,3,4-thiadiazol-2-yl]thiomethyl-3-cephem-4carboxylic acid

(28) 7β-[2-allyloxyimino-2-(2-aminothiazol-4-yl)-acetamido]-3-]5-(3, 4-dihydroxyphenyl)-1,3,4- thiadiazol-2 yl]thiomethyl-3-cephem-4-carboxylic acid
(29) 7β-[2-(2-aminothiazol-4-yl)-2-propargyloxyiminoacetamido]-3-[5-(3, 4-dihydroxyphenyl)-1,3,4-thiadiazol-2-yl]thiomethyl-3-cephem-4-carboxylic acid
(30) 7β-8-[2-(2-aminothiazol-4-yl)-2-benzyloxyiminoacetamido]-3-[5-(3, 4-dihydroxyphenyl)-1,3,4-thiadiazol-2-yl]thiomethyl-3-cephem-4-carboxylic acid
(31) 7β-[2-(2-aminothiazol-4-yl)-2-(3,4-dihydroxybenzyloxyimino) acetamido]-3-[5-(3,4-dihydroxyphenyl)1,3, 4-thiadiazol-2-yl]thiomethyl-3-cephem-4carboxylic acid
(32) 7β-[2-(2-aminothiazol-4-yl)-2-(1-carboxy-1methylethoxyimino) acetamido]-3-[5-(3,4-dihydroxyphenyl)-1,3, 4-thiadiazol-2-yl]thiomethyl-3-cephem-4carboxylic acid
(33) 7β-[2-(2-aminothiazol-4-yl)-2-(1-carboxy-1-cyclopropoxyimino) acetamido]-3-[5-(3,4-dihydroxyphenyl)-1,3, 4-thiadiazol-2-yl]thiomethyl-3-cephem-4carboxylic acid
(34) 7β-[2-(2-aminothiazol-4-yl)-2-(2-carboxymethylbenzyloxyimino) acetamido]-3-[5-(3,4-dihydroxyphenyl)-1,3, 4-thiadiazol-2-yl]thiomethyl-3-cephem-4carboxylic acid
(35) 7β-[2-(2-aminothiazol-4-yl)-2-(α-carboxybenzyloxyimino) acetamido]-3-[5-(3,4-dihydroxyphenyl)-1,3, 4-thiadiazol-2-yl]thiomethyl-3-cephem-4-carboxylic acid
(36) 7β-8-[2-2-aminothiazol-4-yl)-2-(α-carboxy-3,4dihydroxybenzyloxyimino) acetamido]-3-[5-(3,4-dihydroxyphenyl)-1,3, 4-thiadiazol-2-yl]thiomethyl-3-cephem-4-carboxylic acid
(37) 7β-[2-(2-aminothiazol-4-yl)-2-methoxyiminoacetamido]-3-[4-(3, 4-dihydroxyphenyl)-thiazol-2-yl]-thiomethyl-3-cephem-4-carboxylic acid
(38) 3-[4-(3,4-diacetoxyphenyl)thiazol-2-yl]thiomethyl-7β-[2-(2-aminothiazol-4-yl)-2-methoxyiminoacetamido]-3-cephem-4-carboxylic acid
(39) 7β-[2-(2-aminothiazol-4-yl)-2-isopropoxyiminoacetamido]-3-[4-(3, 4-dihydroxyphenyl)-thiazol-2-yl]-thiomethyl-3-cephem-4-carboxylic acid
(40) 7β-[2-allyloxyimino-2-(2-aminothiazol-4-yl)acetamido]-3-[4-(3, 4-dihydroxyphenyl)thiazol-2-yl]-thiomethyl-3-cephem-4-carboxylic acid
(41) 7β-[2-(2-aminothiazol-4-yl)-2-(carboxymethoxyimino)acetamido]-3-[4-(3, 4-dihydroxyphenyl)-thiazol-2-yl]thiomethyl-3-cephem-4-carboxylic acid
(42) 7β-[2-(2-aminothiazol-4-yl)-2-(1-carboxy-1-methylethoxyimino) acetamido]-3[4-(3,4)-dihydroxyphenyl]-thiazol-2-yl]thiomethyl-3-cephem-4-carboxylic acid
(43) 7β-[2-(2-aminothiazol-4-yl)-2-(1-carboxy-1-cyclopropoxyimino) acetamido]-3[4-(3,4-dihydroxyphenyl)-thiazol-2-yl]thiomethyl-3-cephem-4-carboxylic acid
(44) 7β-[2-(2-aminothiazol-4-yl)-2-benzyloxyminoacetamido]-3-[4-(3, 4-dihydroxyphenyl)-thiazol-2-yl]-thiomethyl-3-cephem-4-carboxylic acid
(45) 7β-[2-(2-aminothiazol-4-yl)-2-(3,4-dihydroxybenzyloxyimino) acetamido]-3-[4-(3,4-dihydroxyphenyl)thiazol-2-yl]thiomethyl-3-cephem-4-carboxylic acid
(46) 7β-8-[2-(2-aminothiazol-4-yl)-2-methoxyiminoacetamido]-3-[4-(3, 4-dihydroxyphenyl)-thiazol-2-yl]-thiomethyl-3-cephem-4-carboxylic acid
(47) 3-[4-(3,4-diacetoxyphenyl)thiazol-2-yl]thiomethyl-7β-[2-(2-aminothiazol-4-yl)-2-ethoxyiminoacetamido]-3-cephem-4-carboxylic acid
(48) 7β-[2-(2-aminothiazol-4-yl)-2-(1-carboxy-1-methylethoxyimino)acetamido]-3[5-(3, 4-dihydroxyphenyl)-4-carboxythiazol-2-yl]-thiomethyl-3-cephem-4-carboxylic acid
(49) 7β8-[2-(2-aminothiazol-4-yl)-2-( α-carboxybenzyloxyimino) acetamido]-3-[5-(3,4-dihydroxyphenyl)-4-carboxythiazol-2-yl]thiomethyl-3-cephem-4carboxylic acid
(50) 7β-[2-(2-aminothiazol-4-yl)-2-methoxyiminoacetamido]-3-[5-(3, 4-dihydroxyphenyl-4-carboxythiazol-2-yl]thiomethyl-3-cephem-4-carboxylic acid
(51) 7β-[2-(2-aminothiazol-4-yl)-2-ethoxyiminoacetamido]-3-[5-(3, 4-dihydroxyphenyl)-4-carboxythiazol-2-yl]-thiomethyl-3-cephem-4-carboxylic acid
(52) 7β-[2-(2-aminothiazol-4-yl)-2-cyclopentyloxyiminoacetamido]-3-[5-(3, 4-dihydroxyphenyl)-4-carboxythiazol-2-yl ]thiomethyl-3-cephem-4-carboxylic acid
(53) 7β-[2-allyloxyimino-2-(-2-aminothiazol-4-yl)-acetamido]-3-[5-(3, 4-dihydroxyphenyl)-4-carboxythiazol-2-yl ]thiomethyl-3-cephem-4-carboxylic acid
(54) 7β-[2-(2-aminothiazol-4-yl)-2-propargyloxyiminoacetamido]-3-[5-(3, 4-dihydroxyphenyl)-4-carboxythiazol-2-yl]thiomethyl-3-cephem-4-carboxylic acid
(55) 7β-[2-(2-aminothiazol-4-yl)-2-benzyloxyiminoacetamido]-3-[5-(3, 4-dihydroxyphenyl)-4-carboxythiazol-2-yl]thiomethyl-3-cephem-4-carboxylic acid
(56) 7β-2-(2-aminothiazol-4-yl)-2-methoxyiminoacetamido]-3-[4-(3, 4-dihydroxyphenyl)-5-carboxymethylthiazol-2-yl]thiomethyl-3-cephem-4carboxylic acid
(57) 7β-[2-(2-aminothiazol-4-yl)-2-(1-carboxy-1-methylethoxyimino) acetamido]-3-[4-(3,4-dihydroxyphenyl)5-carboxymethylthiazol-2-yl ]thiomethyl-3-cephem-4carboxylic acid
(58) 3-[4-(3,4-diacetoxyphenyl)-5-carboxymethylthiazol-2-yl]thiomethyl-7β-[2-(2-aminothiazol-4-yl)-2-(1-carboxy-1-methylethoxyimino) acetamido]-3-cephem-4-carboxylic acid
(59) 7β-[2-(2-aminothiazol-4-yl)-2-(1-carboxy-1-cyclopropoxyimino) acetamido]-3-[4-(3,4-dihydroxyphenyl)-5-carboxymethylthiazol-2-yl ]thiomethyl-3-cephem-4-carboxylic acid
60)3-[4-(3,4-diacetoxyphenyl)-5-carboxymethylthiazol-2yl]thiomethyl-7 β-[2-(2-aminothiazol-4-yl)-2-(1-carboxy-1-cyclopropoxyimino) acetamido]-3-cephem-4-carboxylic acid
(61) 3-[4-(3,4-diacetoxyphenyl)-5-carboxymethylthiazol-2-yl]thiomethyl-7β-[2-(2-aminothiazol-4-yl)-2-(α-carboxybenzyloxyimino) acetamido]-3-cephem-4-carboxlic acid
(62) 7β-[2-(2-aminothiazol-4-yl)-2-methoxyiminoacetamido]-3-[5-(3, 4-dihydroxyphenyl)oxazol-2-yl]-thiomethyl-3-cephem-4-carboxylic acid
(63) 7β-[2-(2-aminothiazol-4-yl)-2-ethoxyiminoacetamido]-3-[5-(3, 4-dihydroxyphenyl)oxazol-2-yl]thiomethyl-3-cephem-4-carboxylic acid
(64) 7β-[2-(2-aminothiazol-4-yl)-2-(1-carboxy-1-methylethoxyimino) acetamido]-3-[5-(3,4-dihydroxyphenyl)-oxazol-2-yl]thiomethyl-3-cephem-4-carboxylic acid

(65) 7β-{2-(2-aminothiazol-4-yl)-2-[(α-carboxy-3,4dihydroxybenzyl)oxyimino]acetamido}-3-[5-(3,4-dihydroxyphenyl) oxazol-2-yl]thiomethyl-3-cephem-4-carboxylic acid

(66) 7β-[2-(2-aminothiazol-4-yl)-2-(1-carboxy-1-cyclopropoxyimino) acetamido]-3-[5-(3,4-dihydroxyphenyl)-oxazol-2-yl]thiomethyl-3-cephem-4-carboxylic acid

(67) 3-[5-(3,4-diacetoxyphenyl)oxazol-2-yl]thiomethyl-7β-[2-(2-aminothiazol-4-yl)-2-ethoxyiminoacetamido]-3-cephem-4-carboxylic acid

(68) 7β-[2-(2-aminothiazol-4-yl)-2-methoxyiminoacetamido]-3-(5, 6-dihydroxybenzimidazol-2-yl)thiomethyl-3--cephem-4-carboxylic acid

(69) 7β-[2-(2-aminothiazol-4-yl)-2-methoxyiminoacetamido]-3-(5, 6-dihydroxy-2-methylbenzimidazol-2-yl)-thiomethyl-3-cephem-4-carboxylic acid

(70) 7β-[2-(2-aminothiazol-4-yl)-2-isopropoxyiminoacetamido]-3-(5, 6-dihydroxybenzimidazol-2-yl)thiomethyl-3-cephem-4-carboxylic acid

(71) 7β-[2-allyloxyimino-2-(2-aminothiazol-4-yl)acetamido]-3-(5, 6-dihydroxybenzoimidazol-2-yl)thiomethyl-3-cephem-4-carboxylic acid

(72) 7β-[2-(2-aminothiazol-4-yl)-2-(2-pyrrolidon-3-yl)-oxyiminoacetamido ]-3-(5,6-dihydroxybenzimidazol-2-yl)-thiomethyl-3-cephem-4-carboxylic acid

(73) 7β-[2-(2-aminothiazol-4-yl)-2-(1-carboxy-1-methylethoxyimino) acetamido]-3-(5,6-dihydroxybenzimidazol-2-yl) thiomethyl-3-cephem-4-carboxylic acid

(74) 7β-[2-(2-aminothiazol-4-yl)-2-(1-carboxy-1cyclobenzyloxyimino) acetamido]-3-(5,6-dihydroxybenzimidazol-2-yl) thiomethyl-3-cephem-4carboxylic acid

(75) 7β-[2-(2-aminothiazol-4-yl)-2-methoxyiminoacetamido]-3-(5, 6-dihydroxybenzoxazol-2-yl)thiomethyl-3-cephem-4-carboxylic acid, or

(76) 7β-[2-(2-aminothiazol-4-yl)-2-(1-carboxy-1-methylethoxyimino) acetamido]-3-(5,6-dihydroxybenzoxazol-2-yl) thiomethyl-3-cephem-4-carboxylic acid.

Now, the processes for the preparation of the compounds of the present invention will be described.

The compound of the formula I may be prepared by either one of the following processes A and B.

PROCESS A

The compound of the formula I of the present invention can be prepared by reacting a compound having the formula:

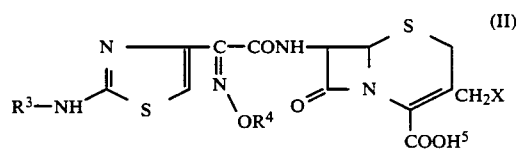
(II)

wherein $R^3$ is a hydrogen atom or an amino-protecting group, $R^4$ is a straight chain or branched chain lower alkyl, cyclic lower alkyl, lower alkenyl, lower alkynyl, aralkyl, phenyl or 2-pyrrolidon-3-yl group which may be substituted (provided that the substituent of $R^4$ is optionally protected), X is a leaving group, and $R^5$ is a hydrogen atom or a carboxyl-protecting group, or a salt thereof, with a compound having the formula:

HS—Q¹ (III)

wherein $Q^1$ is

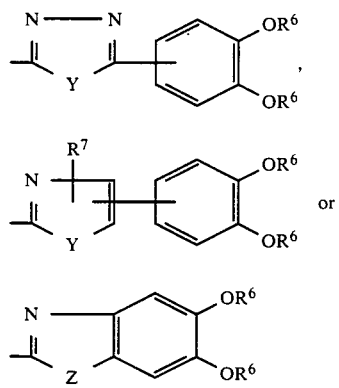

(wherein $R^6$ is a hydrogen atom or a hydroxyl-protecting group, $R^7$ is a hydrogen atom or a carboxyl group or a carboxymethyl group which is optionally protected, Y is a sulfur atom or an oxygen atom and Z is a sulfur atom, an oxygen atom or an imino group which may be substituted by a lower alkyl group), or a salt thereof, to form a compound having the formula:

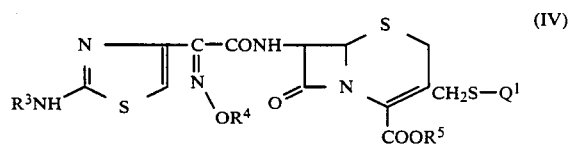
(IV)

wherein $R^3$, $R^4$, $R^5$ and $Q^1$ are as defined above, and optionally removing the protecting groups.

The substituent X in the formula II represents a leaving group. Specifically, there may be mentioned a halogen such as chlorine, bromine or iodine, an acetoxy, a carbamoyloxy, a trifluoromethane-sulfonyloxy and a p-toluenesulfonyloxy. Particularly preferred is a chlorine a bromine, an iodine or an acetoxy.

PROCESS B The compound of the formula I of the present invention can also be prepared by acylating a compound having the formula:

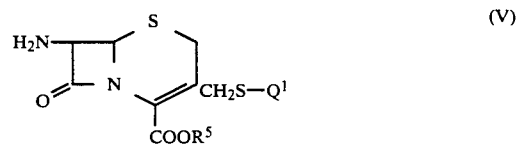
(V)

wherein $R^5$ is a hydrogen atom or a carboxyl-protecting group, and $Q^1$ is

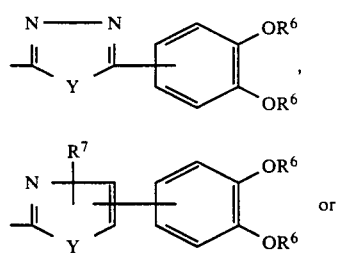

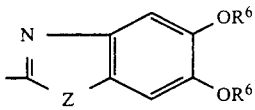

(wherein $R^6$ is a hydrogen atom or a hydroxyl-protecting group, $R^7$ is a hydrogen atom, a carboxyl group or a carboxymehtyl group which is optionally protected, Y is a sulfur atom or an oxygen atom and Z is a sulfur atom, an oxygen atom or an imino group which may be substituted by a lower alkyl group), or a salt thereof, with a carboxylic acid having the formula:

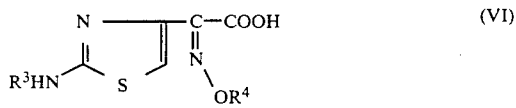

wherein $R^3$ is a hydrogen atom or an amino-protecting group, $R^4$ is a straight chain or branched chain lower alkyl, cyclic lower alkyl, lower alkenyl, lower alkynyl, aralkyl, phenyl or 2-pyrrolidon-3-yl group which may be substituted, (provided that the substituent of $R^4$ is optionally protected), or a reactive derivative thereof, to form a compound having the formula:

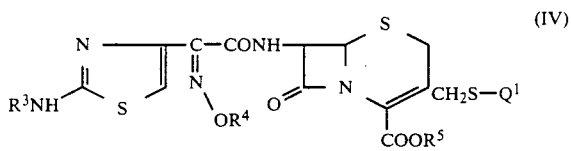

wherein $R^3$, $R^4$, $R^5$ and $Q^1$ are as defined above, and optionally removing the protecting groups.

Further, a compound of the present invention having an acetoxy group as $R^1$ can be prepared in accordance with above processes A and B by using a compound of the formula III or V wherein $R^6$ is an acetyl group. It can also be prepared by acetylating a compound of the formula IV having a hydrogen atom as $R^6$ and optionally removing the protecting groups, or by acetylating a compound of formula I having a hydrogen atom as $R^1$.

Now, processes A and B for the preparation of the compounds of the formula I of the present invention, will be described in detail.

PROCESS A

The reaction of the compound of the formula II with the mercapto derivative of the formula III, may be conducted in an organic solvent such as methylene chloride, chloroform, ethyl ether, ethyl acetate, butyl acetate, tetrahydrofuran, acetonitrile, N,N-dimethylformamide or dimethylsulfoxide, or in a mixture of such solvents. The mercapto derivative of the formula III may be employed in a form of a salt of a metal such as solium, potassium, calcium, magnesium or silver, or a salt of an organic amine such as triethylamine or ethyldiisopropylamine. Further, the mercapto derivative of the formula III may be employed in a form silylated with a silylating agent such as N,O-bis(trimethylsilyl)acetamide. The reaction is conducted by using from 1 to 2 mols of the mercapto derivative of the formula III relative to 1 mol of the compound of the formula II.

The reaction temperature and the reaction time are from 0 to 40° C. and from 0.5 to 5 hours, respectively.

The reaction of a compound of the formula II wherein X is an acetoxy group, with the mercapto derivative of the formula III, may be conducted in a solvent such as water, phosphate buffer solution, acetone, acetonitrile, methanol, ethanol, tetrahydrofuran, dioxane, N,N-dimethylformamide or dimethylsulfoxide, or in a mixture of such solvents The reaction is preferably conducted under a neutral condition at a reaction temperature of from room temperature to 90° C. for the reaction time of from 1 to 10 hours. The reaction is facilitated by conducting it in the presence of from 1 to 20 mols of an iodide such as sodium iodide, a thiocyanate such as sodium thiocyanate, or a quarternary ammonium salt such as trimethylbenzyl ammonium bromide, relative to 1 mol of the compound of the formula II. The compound of the formula I can be produced by optionatlly removing the protecting groups from the compound of the formula IV.

The reaction of a compound of the formula II with the mercapto derivative of the formula III may be conducted in a solvent such as acetic acid, acetone, acetonitrile, methanol, ethanol, tetrahydrofuran, N,N-dimethylformamide, dimethylsulfoxide, or in a mixture of such solvents, in the presence of 1 to 50 mols of an acid such as sulfuric acid, p-toluenesulfonic acid, methanesulfonic acid, trifluoromethanesulfonic acid, chlorosulfonic acid, boron trifluoride and boron trifluoride diethyl etherate in a solvent described above at a reaction temperature of from room temperature to 60° C. for the reaction time of from 1 to 10 hours.

As the protecting groups for the carboxyl, amino and hydroxyl groups in the above formulas, protecting groups which are commonly employed in the field of β-lactam synthesis, may suitably be selected for use. The introduction and removal of the protecting groups may be conducted by employing a suitable method depending upon the type of the protecting group selected, for instance, from those described in "Protective Groups in Organic Synthesis" written by T.W. Greene published in 1981 by Wiley Company and in Protective Groups in Organic Chemistry written by J.F.W. McOmie published in 1973 by Plenum Press.

As the carboxyl-protecting group, there may be mentioned t-butyl, 2,2,2-trichloroethyl, acetoxymethyl, propionyloxymethyl, pivaloyloxymethyl, 1-acetoxyethyl, 1-propionyloxyethyl, 1-(ethoxycarbonyloxy)ethyl, phthalidyl, benzyl, 4-methoxybenzyl, 3,4-dimethoxybenzyl, 4-nitrobenzyl, benzhydryl, bis(4-methoxyphenyl)methyl, (5-methyl-2-oxo-1,3-dioxol-4-yl)methyl, trimethylsilyl and t-butyldimethylsilyl. Particularly preferred are benzhydryl, t-butyl and silyl.

As the amino-protecting group, there may be mentioned, for example, trityl, formyl, chloroacetyl, trifluoroacetyl, t-butoxycarbonyl, trimethysilyl and t-butyldimethylsilyl.

As the hydroxyl-protecting group, there may be mentioned, for example, 2-methoxyethoxymethyl, methoxymethyl, methylthiomethyl, tetrahydropyranyl, phenacyl, isopropyl, t-butyl, benzyl, 4-nitrobenzyl, acetyl, 2,2,2-trichloroethoxycarbonyl, benzyloxycarbonyl, trimethylsilyl, t-butyldimethylsilyl, or a cyclic acetal such as methylene acetal, ethylene acetal or benzylidene acetal, an orthoester such as methoxymethylidene ethoxymethylidene, a cyclic ketal such as isopropylidene ketal or a cyclic carbonate, which is formed by the combination of protecting groups each other.

The method for the removal of the protecting groups will be described in detail. For instance, the removal of a protecting group such as trityl, formyl, t-butoxycarbonyl, benzhydryl, t-butyl or 2-methoxyethoxymethyl, may be conducted by means of an inorganic or organic acid such as hydrochloric acid, formic acid, trifluoroacetic acid, benzenesulfonic acid or p-toluenesulfonic acid. Trifluoroacetic acid is particularly preferred.

When trifluoroacetic acid is used as the acid, the reaction can be facilitated by an addition of anisole, thioanisole or phenol, and side reactions can be thereby suppressed.

The reaction may be conducted in a solvent which is inert to the reaction, such as water, methylene chloride, chloroform, ethylene chloride or benzene, or in a mixture of such solvents. The reaction temperature and time are suitably selected depending upon the chemical properties of the compound of the formula IV and the compound of the formula I of the present invention and the type of the protecting group to be removed. The reaction is preferably conducted under a condition ranging from an ice-cooling condition to a slightly heated condition.

The starting compound of the formula II for process A may be prepared in the following manner. The compound of the formula II can be prepared by reacting a 7β-amino-3-chloromethyl-3-cephem-4-carboxylic acid derivative (synthesized in accordance with e.g. Japanese Unexamined Patent Publications No. 76089/1975, No. 86187/1981 and the Journal of Antibiotics Vol. 38, p 1738 (1985)), 7β-aminocephalosporanic acid or its ester, with a carboxylic acid of the formula VI or its reactive derivative (such as its acid halide, mixed acid anhydride, activated ester, etc.).

A compound of the formula II wherein X is an iodine atom, can be prepared by reacting a compound of the formula II wherein X is a chlorine atom, with an iodide such as sodium iodide in a solvent such as acetone or N,N-dimethylformamide or in two-phase system of water and the organic solvent in the presence of an interphase transfer catalyst, under cooling with ice or at room temperature in accordance with a method disclosed in Japanese Unexamined Patent Publication No. 27679/1976 or Synthetic Communications Vol. 16, P. 1029-1035 (1986), or by reacting a compound of the formula II wherein X is an acetoxy group, with iodotrimethylsilane in a solvent such as methylene chloride, chloroform, diethyl ether, ethyl acetate, butyl acetate, tetrahydrofuran, acetonitrile, N,N-dimethylformamide, or dimethylsulfoxide, or in a mixture of such solvent in accordance with the method described in Tetrahedron Letters Vol. 22, p 3915 (1981). The product may be used for the subsequent reaction without or after isolation. The mercapto derivative having adjacent dihydroxy or diacetoxy groups of the formula III is a novel compound not disclosed in any literature. The compound can be produced by the following methods.

A 2-mercapto-5-(3,4-disubstituted phenyl)-1,3,4-oxadiazole derivative can be prepared by reacting a benzohydrazide derivative with carbon disulfide in ethanol in the presence of potassium hydroxide.

A 2-mercapto-5-(3,4-disubstituted phenyl)-1,3,4thiadiazole derivative can be prepared
i) by reacting 3,4-disubstituted thiobenzamide with hydrogen sulfide in pyridine in the presence of triethylamine; or
ii) by reacting potassium 3-(3,4-disubstituted benzoyl)-dithiocarbazate with concentrated sulfaric acid.

A 2-mercapto-4-(3,4-disubstituted phenyl)thiazole derivative can be prepared by reacting 2-chloro-3′,4′-dihydroxyacetophenone which is prepared in accordance with the method disclosed in Chemical Abstracts, 84-43639s (1976), with ammonium dithiocarbamate in methanol.

A 4-carboxy-5-(3,4-disubstituted phenyl)-2-mercaptothiazole derivative can be prepared by using piperonal as a starting material in accordance with a method disclosed in Organic Syntheses, Coll. Voll. II. p 11-12, 1-3 and 519-520. Namely, piperonal is converted to 3-(3,4-disubstituted phenyl)pyruvic acid, and then brominated to obtain 3-bromo-3-(3,4-disubstituted phenyl)pyruvic acid. Further, the compound was reacted with ammonium dithiocarbamate to produce the desired compound.

A 5-carboxymethyl-4-(3,4-disubstituted phenyl)-2-mercaptothiazole derivative can be produced by reacting veratrole with succinic anhydride in the presence of anhydrous aluminum chloride to obtain 3-(3,4-dimethoxybenzoyl)propionic acid, subjecting the propionic acid to demethylation with hydrobromic acid to obtain 3-(3,4-dihydroxybenzoyl)propionic acid, then, subjecting it to enol-lactonation in the presence of acetic anhydride and sodium acetate, reacting the resulting compound sequentially with N-bromosuccinimide and with diphenyldiazomethane to obtain 3-(3,4-diacetoxybenzoyl)-3-bromopropionate, and reacting the propionate with ammonium dithiocarbamate to obtain the desired product.

A 2-mercapto-5-(3,4-disubstituted phenyl)oxazole derivative can be produced by reacting 2-chloro-3′,4′-dihydroxyacetophenone prepared in accordance with the method disclosed in Chemical Abstract, 84-43639s (1976), with sodium azide to obtain an azide compound, conducting catalytic hydrogenation of the azide compound to obtain 2-amino-3′,4′-dihydroxyacetophenone, and reacting the acetophenone with carbon disulfide in ethanol in the presence of sodium ethoxide in accordance with the method disclosed in Chemical Abstracts, 67-43806t (1967).

A 2-mercaptobenzimidazole derivative can be produced by using veratrole as a starting material in accordance with the methods disclosed in Synthesis, p 1033 (1974) and in Org. Synth., Col. 1, Vol. 1, IV, p 56 (1963).

A 2-mercaptobenzoxazole derivative can be prepared by using veratraldehyde as a starting material in accordance with the methods disclosed in Journal of the Chemical Society Perkin Transactions 1, p 1353 (1974), Canadian Journal of Chemistry, Vol. 44, p 1879 (1966) and Journal of Pharmaceutical Science, Vol. 76, p 1002 (1956).

A 2-mercaptobenzthiazole derivative can be produced by conducting nitration and catalytic hydrogenation by using veratrole as a starting material, to obtain 3,4-dimethoxy-6-nitroaniline, followed by the convertion to a diazpnium salt, reacting the diazonium salt with potassium 0-ethyldithiocarbonate to obtain O-ethyl 3,4-dimethoxy-6-nitrophenyl dithiocarbonate, and by conducting a reductive ring closure reaction with stannous chloride in ethanol The 2-(2-aminothiazol-4-yl)-2-substituted oxyiminoacetic acid derivative of the formula VI, can be prepared by using a 2-(2-aminothiazol-4-yl)glyoxylic acid derivative or 2-(2-aminothiazol-4-yl)-2-hydroxyimino acetic acid derivative by a method disclosed in e.g. Chemical and Pharmaceutical Bulletin, Vol 25, P. 3115-3119

(1977) or Journal of the Japanese Chemical Society p 785-801 (1981).

PROCESS B

The compound of the formula IV may be prepared by reacting the compound of the formula V with the carboxylic acid of the formula VI or its reactive derivative (such as its acid halide, mixed anhydride or activated ester) in a solvent inert to the reaction such as water, acetone, dioxane, acetonitrile, tetrahydrofuran, methylene chloride, chloroform, ethylene chloride, benzene, ethyl acetate, N,N-dimethylformamide or dimethylsulfoxide, or in a mixture of such solvents.

The reaction is conducted by using from 1 to 1.5 mols of the carboxylic acid of the formula VI or its reactive derivative relative to 1 mol of the compound of the formula V, and the reaction temperature is from −40° to 40° C.

When an acid halide is used as the reactive derivative of the formula VI, the reaction is preferably conducted in the presence of an acid-absorbing agent such as triethylamine, N-methylmorphorine, N,N-dimethylaniline or pyridine.

The acid halide-forming reaction is carried out by using from 1 to 10 mols, preferably from 1 to 1.5 mols of the halogenating agent such as thionyl chloride, phosphorus trichloride, phosphorus tribromide, phosphorus pentachloride, phosphorus oxychloride, oxalylchloride or phosgene, at a reaction temperature of from −40° to 100° C., preferably from −20° to 20° C. for a reaction time of from 10 to 120 minutes.

The mixed acid anhydride-forming reaction is conducted by using from 1 to 1.2 mols of a chloroformate such as methyl chloroformate, ethyl chloroformate or isobutyl chloroformate in the presence of from 1 to 1.2 mols of an acid-absorbing agent such as triethylamine, N-methylmorphorine, N,N-dimethylaniline or pyridine, relative to 1 mol of the carboxylic acid of the formula VI. The reaction temperature is from −40° to 20° C., preferably from −20° to 5° C. The reaction time is from 10 to 60 minutes.

The active ester-forming reaction is conducted by using from 1 to 1.2 mols of a N-hydroxy compound (such as N-hydroxysuccinimide or 1-hydroxybenzotriazole) or a phenol compound (such as 4-nitrophenol, 2,4-dinitrophenol or 2,4,5,-trichlorophenol) and from 1 to 1.4 mols of N,N'-dicyclohexylcarbodiimide, relative to 1 mol of the carboxylic acid of the formula VI. The reaction temperature is from −10° to 50° C. The reaction time is from 0.5 to 2 hours.

When the carboxylic acid of the formula VI is used in the form of a free acid in the acylation reaction, the compound of the formula IV may be prepared in the presence of a condensation agent such as a carbodiimide such as N,N'-dicyclohexylcarbodiimide, or phosphorus oxychloride, an phosphorus oxychloride adduct of N,N-dimethylformamide. The preparation of the compound of the formula I of the present invention from the compound of the formula IV, is substantially the same as in process A.

The starting compound of the formula V in process B, may be prepared by a method disclosed in e.g. Cephalosporins and Penicillins, Academic Press, p 151-171, (1972) written by Flynn. For instance, a 7β-acylamino-3-halomethyl-3-cephem-4-carboxylic acid derivative (prepared in accordance with Japanese Unexamined Patent Publication No. 72590/1983 or No. 154588/1983), a 7β-acylaminocephalosporanic acid derivative or a 7β-aminocephalosporanic acid, is reacted with the mercapto derivative of the formula III to obtain a compound having the formula:

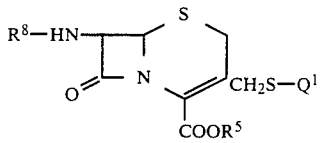

wherein $R^5$ and $Q^1$ are as defined above are $R^8$ is a hydrogen atom or an acyl group, optionally followed by deacylation.

The deacylation reaction is commonly known in this field. When $R^8$ in the compound of the above formula is, for example, a phenylacetyl, phenoxyacetyl or aminoadipyl group, the deacylation is conducted in accordance with a method disclosed in Japanese Examined Patent Publication No. 20319/1974 and Japanese Patent Application No. 91431/1986 by the present inventors. For instance, the $R^8$ group can be chemically removed by reacting the compound with phosphorus pentachloride or phosphorus oxychloride in a solvent such as benzene, toluene, ethyl acetate, methylene chloride or ethylene chloride, or in a mixture of such solvents in the presence of an acid-absorbing agent such as pyridine, triethylamine, sodium hydrogencarbonate or potassium hydrogencarbonate at a temperature of from −80° to 50° C., preferably from −65° to 0° C. for from 0.5 to 2 hours, followed by treatment with a lower alcohol such as methanol, ethanol or propanol, and then a hydrolysis.

The $R^8$ can also be enzymatically removed by the treatment with penicillin G acylase or fixed penicillin G acylase in water or in a mixture of water and an organic solvent such as acetone, acetonitrile, methanol, ethanol or tetrahydrofuran at a pH of from 7 to 8, preferably from 7.5 to 7.8. This enzymatic reaction is preferably conducted at a constant pH level by adding a base such as lithium hydroxide, sodium hydroxide, potassium hydroxide, triethylamine, tripropylamine or pyridine.

The in vitro antibacterial activities of the compounds of the present invention against various microorganisms, were measured by the following agar plate dilution method. One platinum loopfull of each test microorganism incubated overnight in Mueller Hinton broth, was inoculated to Mueller Hinton agar (inoculum size: $10^6$ CFU/ml). Such culture media containing various antibiotics in various concentrations were prepared. After incubation at 37° C. for 16 hours, the minimum inhibitory concentrations (MIC: μg/ml) were measured. As comparative compounds, cefotaxime, ceftazidime and the compounds having an unsubstituted, monohydroxysubstituted, monoacetoxy-substituted or dimethoxysubstituted phenyl substituted heterocyclic thiomethyl group at the 3-position of the cephem nuclear (compounds of REFERENCE EXAMPLES 1-24). The results are shown in the following Table A.

TABLE A

| Test microorganism | Minimum Inhibitory Concentration (MIC: μg/ml) |
|---|---|
| | Compound Compound Compound Compound Compound Compound Compound Compound |

TABLE A-continued

| Test microorganism | Minimum Inhibitory Concentration (MIC: μg/ml) | | | | | | | |
|---|---|---|---|---|---|---|---|---|
| | of Ex. 1 | of Ex. 4 | of Ex. 5 | of Ex. 6 | of Ex. 7 | of Ex. 8 | of Ex. 9 | of Ex. 10 |
| 1. S. aureus 209P NIHJ-JC1 | 1.56 | 3.12 | 0.78 | 1.56 | 1.56 | 0.78 | 0.78 | 12.5 |
| 2. E. coli NIHJ JC2 | 0.05 | 0.05 | 0.05 | 0.05 | 0.1 | 0.1 | 0.1 | 0.05 |
| *3. E. coli CSH2 (RK1) | <0.006 | <0.006 | 0.0125 | 0.0125 | <0.006 | <0.006 | 0.0125 | <0.006 |
| 4. K. pneumoniae PCI-602 | <0.006 | <0.006 | <0.006 | <0.006 | <0.006 | <0.006 | 0.0125 | <0.006 |
| *5. E. coli CSH(RE45) | 0.78 | 0.78 | 0.0125 | 0.78 | 1.56 | 0.78 | 0.0125 | 0.0125 |
| *6. K. oxytoca GN10650 | 0.39 | 0.39 | 0.78 | 0.39 | 0.1 | 3.12 | 6.25 | 0.1 |
| *7. K. pneumoniae No. 42 | 0.025 | 0.025 | 0.05 | 0.025 | 0.025 | 0.05 | 0.025 | 0.025 |
| 8. P. vulgaris HX-19 | <0.006 | <0.006 | <0.006 | <0.006 | <0.006 | <0.006 | <0.006 | <0.006 |
| *9. P. vulgaris No. 33 | 0.0125 | 0.0125 | 0.025 | 0.0125 | 0.0125 | 0.0125 | 0.025 | 0.025 |
| 10. S. marcescens IAM 1184 | <0.006 | <0.006 | 0.0125 | <0.006 | 0.025 | 0.0125 | 0.0125 | 0.0125 |
| 11. E. cloacae 963 | <0.006 | <0.006 | 0.0125 | <0.006 | 0.0125 | <0.006 | 0.0125 | 0.025 |
| *12. E. cloacae Nek 39 | 0.05 | 0.05 | 0.1 | 0.05 | 0.05 | 0.05 | 0.1 | 0.05 |
| *13. E. coli GN5482 | 0.39 | 0.39 | 0.39 | 0.39 | 0.39 | 0.39 | 0.39 | 0.39 |
| *14. M. morganii GN5407 | 0.0125 | 0.0125 | 0.025 | 0.0125 | 0.0125 | 0.0125 | 0.0125 | 0.025 |
| *15. S. marcescens No. 16-2 | 0.78 | 1.56 | 0.78 | 0.78 | 1.56 | 1.56 | 6.25 | 0.39 |
| 16. Ps. aeruginosa IF03445 | 0.78 | 0.78 | 0.39 | 0.2 | 0.39 | 0.2 | 1.56 | 0.39 |
| 17. Ps. aeruginosa AK 109 | 0.39 | 0.39 | 0.39 | 0.1 | 0.2 | 0.2 | 0.2 | 0.2 |
| 18. Ps. aeruginosa AKR17 | >100 | >100 | >100 | >100 | 50 | 100 | >100 | 12.5 |
| 19. Ps. cepacia 23 | 0.1 | 0.1 | <0.006 | 0.05 | <0.006 | 0.025 | 0.05 | <0.006 |
| 20. A. calcoaceticus No. 4 | 0.1 | 0.1 | 0.1 | 0.1 | 0.1 | 0.1 | 0.1 | 0.05 |

| | Compound of Ex. 11 | Compound of Ex. 12 | Compound of Ex. 13 | Compound of Ex. 14 | Compound of Ex. 15 | Compound of Ex. 16 |
|---|---|---|---|---|---|---|
| 1. S. aureus 209P NIHJ-JC1 | 25 | 12.5 | 0.39 | 1.56 | 12.5 | 1.56 |
| 2. E. coli NIHJ JC2 | 0.1 | 0.05 | 0.1 | 0.39 | 0.1 | 0.2 |
| *3. E. coli CSH2 (RK1) | <0.006 | <0.006 | <0.006 | 0.05 | <0.006 | 0.025 |
| 4. K. pneumoniae PCI-602 | <0.006 | <0.006 | <0.006 | <0.006 | <0.006 | <0.006 |
| *5. E. coli CSH(RE45) | 1.56 | <0.006 | 1.56 | 3.12 | 3.12 | 3.12 |
| *6. K. oxytoca GN10650 | 0.0125 | 0.025 | 0.39 | 6.25 | 0.0125 | 0.1 |
| *7. K. pneumoniae No. 42 | 0.025 | 0.025 | 0.05 | 0.39 | 0.05 | 0.2 |
| 8. P. vulgaris HX-19 | <0.006 | <0.006 | <0.006 | 0.05 | <0.006 | 0.05 |
| *9. P. vulgaris No. 33 | 0.025 | 0.025 | 0.025 | 0.2 | 0.0125 | 0.78 |
| 10. S. marcescens IAM 1184 | 0.0125 | 0.0125 | 0.0125 | 0.1 | 0.025 | 0.1 |
| 11. E. cloacae 963 | 0.025 | 0.05 | 0.0125 | 0.39 | 0.025 | 0.39 |
| *12. E. cloacae Nek 39 | 0.05 | 0.025 | 0.1 | 1.56 | 0.05 | 0.78 |
| *13. E. coli GN5482 | 0.39 | 0.2 | 0.39 | 3.12 | 1.56 | 0.78 |
| *14. M. morganii GN5407 | 0.05 | 0.025 | 0.025 | 0.1 | 0.05 | 0.2 |
| *15. S. marcescens No. 16-2 | 0.39 | 1.56 | 3.12 | 25 | 0.78 | 25 |
| 16. Ps. aeruginosa IF03445 | 0.39 | 0.39 | 0.39 | 12.5 | 0.78 | 6.25 |
| 17. Ps. aeruginosa AK 109 | 0.2 | 0.2 | 0.39 | 100 | 0.39 | 0.78 |
| 18. Ps. aeruginosa AKR17 | 1.56 | 3.12 | 50 | >100 | 0.78 | 3.12 |
| 19. Ps. cepacia 23 | <0.006 | <0.006 | 0.025 | 0.1 | <0.006 | <0.006 |
| 20. A. calcoaceticus No. 4 | 0.05 | 0.05 | 0.2 | 0.39 | 0.05 | 0.1 |

| | Compound of Ex. 22 | Compound of Ex. 23 | Compound of Example 24 | | Compound of Ex. 25 | Compound of Ex. 26 | Compound of Ex. 30 |
|---|---|---|---|---|---|---|---|
| | | | DA | DB | | | |
| 1. S. aureus 209P NIHJ-JC1 | 0.78 | 6.25 | 12.5 | 25 | 0.78 | 0.78 | 0.78 |
| 2. E. coli NIHJ JC2 | 0.39 | 0.2 | 0.2 | 0.39 | 0.2 | 0.1 | 0.2 |
| *3. E. coli CSH2 (RK1) | 0.0125 | <0.006 | <0.006 | 0.0125 | <0.006 | <0.006 | 0.0125 |
| 4. K. pneumoniae PCI-602 | <0.006 | <0.006 | <0.006 | <0.006 | <0.006 | <0.006 | <0.006 |
| *5. E. coli CSH(RE45) | <0.006 | <0.006 | <0.006 | 0.0125 | 0.025 | 0.0125 | 0.78 |
| *6. K. oxytoca GN10650 | 100 | 0.1 | 0.0125 | 0.025 | 0.78 | 0.78 | 1.56 |
| *7. K. pneumoniae No. 42 | 0.0125 | <0.006 | 0.0125 | 0.025 | 0.0125 | 0.0125 | <0.006 |
| 8. P. vulgaris HX-19 | <0.006 | <0.006 | <0.006 | 0.05 | <0.006 | <0.006 | <0.006 |
| *9. P. vulgaris No. 33 | 0.025 | 0.0125 | 0.0125 | 0.1 | 0.025 | 0.025 | 0.39 |
| 10. S. marcescens IAM 1184 | 0.05 | 0.025 | 0.025 | 0.05 | 0.0125 | 0.0125 | 0.0125 |
| 11. E. cloacae 963 | 0.025 | 0.025 | 0.05 | 0.1 | 0.025 | 0.025 | 0.05 |
| *12. E. cloacae Nek 39 | 0.05 | 0.1 | 0.025 | 0.05 | 0.39 | 0.1 | 0.1 |
| *13. E. coli GN5482 | 0.78 | 0.78 | 0.39 | 0.39 | 0.78 | 0.78 | 0.78 |
| *14. M. morganii GN5407 | 0.0125 | 0.025 | 0.025 | 0.2 | 0.025 | 0.025 | 0.05 |
| *15. S. marcescens No. 16-2 | 0.78 | 1.56 | 0.78 | 0.78 | 1.56 | 1.56 | 12.5 |
| 16. Ps. aeruginosa IF03445 | 1.56 | 0.39 | 0.78 | 1.56 | 0.78 | 0.78 | 0.39 |
| 17. Ps. aeruginosa AK 109 | 1.56 | 0.1 | 0.1 | 0.2 | 0.78 | 0.39 | 0.39 |
| 18. Ps. aeruginosa AKR17 | >100 | 12.5 | 0.78 | 0.78 | 100 | 50 | 25 |
| 19. Ps. cepacia 23 | 0.025 | <0.006 | <0.006 | <0.006 | <0.006 | 0.0125 | <0.006 |
| 20. A. calcoaceticus No. 4 | 0.2 | 0.1 | 0.05 | 0.05 | 0.2 | 0.2 | 0.2 |

| | Compound of Ex. 31 | Compound of Ex. 32 | Compound of Ex. 34 | Compound of Ex. 35 | Compound of Example 38 | | Compound of Ex. 39 | Compound of Ex. 40 |
|---|---|---|---|---|---|---|---|---|
| | | | | | DA | DB | | |
| 1. S. aureus 209P NIHJ-JC1 | 0.78 | 0.39 | 12.5 | 12.5 | 0.78 | 1.56 | 1.56 | 1.56 |
| 2. E. coli NIHJ JC2 | 0.1 | 0.39 | 0.1 | 0.2 | 0.2 | 0.78 | 0.1 | 0.2 |
| *3. E. coli CSH2 (RK1) | <0.006 | <0.006 | <0.006 | <0.006 | <0.006 | 0.025 | 0.0125 | 0.025 |
| 4. K. pneumoniae PCI-602 | <0.006 | <0.006 | 0.0125 | <0.006 | <0.006 | <0.006 | <0.006 | <0.006 |

TABLE A-continued

| Test microorganism | Minimum Inhibitory Concentration (MIC: μg/ml) | | | | | | | |
|---|---|---|---|---|---|---|---|---|
| *5. E. coli CSH(RE45) | 0.0125 | 1.56 | <0.006 | <0.006 | <0.006 | 0.0125 | 0.1 | 0.2 |
| *6. K. oxytoca GN10650 | 0.78 | 0.39 | 0.025 | 0.025 | 0.025 | 0.1 | 1.56 | 1.56 |
| *7. K. pneumoniae No. 42 | <0.006 | 0.0125 | 0.0125 | 0.0125 | 0.0125 | 0.1 | 0.2 | 0.2 |
| 8. P. vulgaris HX-19 | <0.006 | 0.0125 | <0.006 | <0.006 | 0.0125 | 0.025 | <0.006 | 0.0125 |
| *9. P. vulgaris No. 33 | 0.025 | 0.2 | 0.025 | 0.0125 | 0.025 | 0.1 | 0.05 | 0.1 |
| 10. S. marcescens IAM 1184 | 0.0125 | 0.025 | 0.025 | 0.025 | 0.025 | 0.1 | 0.05 | 0.1 |
| 11. E. cloacae 963 | 0.0125 | 0.1 | 0.1 | 0.05 | 0.05 | 0.2 | 0.025 | 0.05 |
| *12. E. cloacae Nek 39 | 0.2 | 0.2 | 0.1 | 0.05 | 0.1 | 0.39 | 0.39 | 0.39 |
| *13. E. coli GN5482 | 0.39 | 0.78 | 0.78 | 0.39 | 0.2 | 0.78 | 0.78 | 0.78 |
| *14. M. morganii GN5407 | 0.0125 | 0.1 | 0.05 | 0.05 | 0.05 | 0.2 | 0.05 | 0.1 |
| *15. S. marcescens No. 16-2 | 0.39 | 12.5 | 0.1 | 0.39 | 0.2 | 6.25 | 3.12 | 6.25 |
| 16. Ps. aeruginosa IFO3445 | 0.78 | 0.78 | 0.39 | 0.39 | 0.39 | 3.12 | 1.56 | 1.56 |
| 17. Ps. aeruginosa AK 109 | 0.2 | 0.39 | 0.1 | 0.2 | 0.2 | 0.78 | 3.12 | 3.12 |
| 18. Ps. aeruginosa AKR17 | 100 | >100 | 1.56 | 1.56 | 0.1 | 1.56 | >100 | <100 |
| 19. Ps. cepacia 23 | 0.0125 | <0.006 | <0.006 | <0.006 | <0.006 | <0.006 | 0.2 | — |
| 20. A. calcoaceticus No. 4 | 0.1 | 0.39 | 0.05 | 0.05 | 0.025 | 0.05 | 0.39 | 0.78 |

| | Compound of Ex. 41 | Compound of Ex. 42 | Compound of Ex. 43 | Compound of Ex. 44 | Compound of Ex. 45 | Compound of Ex. 46 | Compound of Ex. 48 |
|---|---|---|---|---|---|---|---|
| 1. S. aureus 209P NIHJ-JC1 | 1.56 | 0.78 | 12.5 | 12.5 | 6.25 | 0.78 | 3.12 |
| 2. E. coli NIHJ JC2 | 0.2 | 0.2 | 0.2 | 0.2 | 0.2 | 0.2 | 0.39 |
| *3. E. coli CSH2 (RK1) | 0.0125 | 0.025 | 0.025 | 0.025 | 0.0125 | 0.025 | 0.025 |
| 4. K. pneumoniae PCI-602 | <0.006 | <0.006 | <0.006 | <0.006 | <0.006 | <0.006 | <0.006 |
| *5. E. coli CSH(RE45) | <0.006 | 0.025 | 0.025 | 0.0125 | 0.05 | 0.78 | 0.05 |
| *6. K. oxytoca GN10650 | 0.39 | 3.12 | 0.39 | 0.025 | 0.1 | 3.12 | 1.56 |
| *7. K. pneumoniae No. 42 | 0.1 | 0.2 | 0.1 | 0.1 | 0.1 | 0.1 | 0.05 |
| 8. P. vulgaris HX-19 | 0.025 | 0.0125 | <0.006 | 0.0125 | <0.006 | 0.0125 | 0.0125 |
| *9. P. vulgaris No. 33 | 0.05 | 0.05 | 0.05 | 0.025 | 0.025 | 0.025 | 0.05 |
| 10. S. marcescens IAM 1184 | 0.05 | 0.05 | 0.05 | 0.05 | 0.05 | 0.1 | 0.1 |
| 11. E. cloacae 963 | 0.1 | 0.05 | 0.1 | 0.1 | 0.05 | 0.2 | 0.1 |
| *12. E. cloacae Nek 39 | 0.2 | 0.39 | 0.2 | 0.1 | 0.05 | 0.1 | 0.78 |
| *13. E. coli GN5482 | 0.78 | 0.78 | 0.39 | 0.39 | 0.39 | 0.78 | 1.56 |
| *14. M. morganii GN5407 | 0.05 | 0.05 | 0.05 | 0.05 | 0.05 | 0.1 | 0.1 |
| *15. S. marcescens No. 16-2 | 6.25 | 6.25 | 1.56 | 1.56 | 0.39 | 3.12 | 6.25 |
| 16. Ps. aeruginosa IFO3445 | 0.78 | 0.78 | 0.78 | 0.39 | 0.78 | 1.56 | 1.56 |
| 17. Ps. aeruginosa AK 109 | 0.39 | 0.78 | 0.78 | 0.39 | 0.78 | 3.12 | 0.39 |
| 18. Ps. aeruginosa AKR17 | 50 | 100 | 12.5 | 1.56 | 6.25 | 100 | 50 |
| 19. Ps. cepacia 23 | 0.05 | 0.1 | <0.006 | <0.006 | <0.006 | 0.2 | 0.1 |
| 20. A. calcoaceticus No. 4 | 0.39 | 0.39 | 0.2 | 0.2 | 0.1 | 0.78 | 0.39 |

| | Compound of Ex. 49 | Compound of Ex. 50 | Compound of Example 51 | | Compound of Ex. 52 | Compound of Ex. 53 |
|---|---|---|---|---|---|---|
| | | | DA | DB | | |
| 1. S. aureus 209P NIHJ-JC1 | 1.56 | 50 | 100 | 25 | 12.5 | 12.5 |
| 2. E. coli NIHJ JC2 | 0.39 | 0.39 | 3.12 | 0.39 | 0.39 | 0.78 |
| *3. E. coli CSH2 (RK1) | 0.025 | <0.006 | 0.05 | 0.0125 | 0.0125 | 0.0125 |
| 4. K. pneumoniae PCI-602 | <0.006 | <0.006 | 0.0125 | <0.006 | <0.006 | <0.006 |
| *5. E. coli CSH(RE45) | 0.05 | 0.0125 | 0.1 | 0.0125 | 0.05 | 0.025 |
| *6. K. oxytoca GN10650 | 6.25 | 0.025 | 0.1 | 0.025 | 6.25 | 3.12 |
| *7. K. pneumoniae No. 42 | 0.05 | 0.05 | 0.2 | 0.05 | 0.1 | 0.1 |
| 8. P. vulgaris HX-19 | 0.0125 | <0.006 | 0.2 | <0.006 | 0.0125 | 0.0125 |
| *9. P. vulgaris No. 33 | 0.05 | <0.006 | 0.39 | 0.0125 | 0.1 | 0.025 |
| 10. S. marcescens IAM 1184 | 0.1 | 0.025 | 0.1 | 0.05 | 0.1 | 0.05 |
| 11. E. cloacae 963 | 0.1 | 0.0125 | 0.2 | 0.05 | 0.1 | 0.1 |
| *12. E. cloacae Nek 39 | 0.78 | 0.025 | 0.1 | 0.05 | 0.78 | 0.39 |
| *13. E. coli GN5482 | 1.56 | 0.39 | 1.56 | 0.78 | 3.12 | 3.12 |
| *14. M. morganii GN5407 | 0.1 | 0.025 | 0.2 | 0.05 | 0.1 | 0.05 |
| *15. S. marcescens No. 16-2 | 3.12 | 0.78 | 1.56 | 0.78 | 12.5 | 6.25 |
| 16. Ps. aeruginosa IFO3445 | 0.78 | 0.39 | 1.56 | 0.39 | 6.25 | 3.12 |
| 17. Ps. aeruginosa AK 109 | 0.78 | 0.39 | 1.56 | 0.39 | 12.5 | 3.12 |
| 18. Ps. aeruginosa AKR17 | 100 | 1.56 | 1.56 | 0.39 | >100 | 50 |
| 19. Ps. cepacia 23 | 0.05 | <0.006 | <0.006 | <0.006 | 0.025 | 0.025 |
| 20. A. calcoaceticus No. 4 | 0.39 | 0.1 | 0.1 | 0.1 | 0.39 | 0.39 |

| | Compound of Ex. 54 | Compound of Ex. 55 | Compound of Ex. 56 | Compound of Ex. 57 | Compound of Ex. 58 |
|---|---|---|---|---|---|
| 1. S. aureus 209P NIHJ-JC1 | 3.12 | 6.25 | 6.25 | 3.12 | 12.5 |
| 2. E. coli NIHJ JC2 | 1.56 | 0.78 | 0.78 | 0.78 | 0.39 |
| *3. E. coli CSH2 (RK1) | 0.1 | 0.0125 | 0.0125 | 0.0125 | 0.0125 |
| 4. K. pneumoniae PCI-602 | <0.006 | <0.006 | <0.006 | <0.006 | <0.006 |
| *5. E. coli CSH(RE45) | 3.12 | 0.1 | 0.025 | 0.1 | 0.39 |
| *6. K. oxytoca GN10650 | 1.56 | 50 | 12.5 | 25 | 12.5 |
| *7. K. pneumoniae No. 42 | 0.1 | 0.1 | 0.1 | 0.1 | 0.1 |
| 8. P. vulgaris HX-19 | <0.006 | <0.006 | <0.006 | <0.006 | 0.0125 |
| *9. P. vulgaris No. 33 | 0.025 | 0.025 | 0.05 | 0.025 | 0.025 |
| 10. S. marcescens IAM 1184 | 0.05 | 0.1 | 0.05 | 0.1 | 0.1 |
| 11. E. cloacae 963 | 0.1 | 0.1 | 0.2 | 0.05 | 0.1 |
| *12. E. cloacae Nek 39 | 0.2 | 0.39 | 0.78 | 0.39 | 1.56 |

TABLE A-continued

| Test microorganism | Minimum Inhibitory Concentration (MIC: μg/ml) | | | | |
|---|---|---|---|---|---|
| *13. E. coli GN5482 | 1.56 | 3.12 | 3.12 | 3.12 | 3.12 |
| *14. M. morganii GN5407 | — | — | 0.05 | — | — |
| *15. S. marcescens No. 16-2 | 1.56 | 3.12 | 6.25 | 6.25 | 3.12 |
| 16. Ps. aeruginosa IF03445 | 1.56 | 3.12 | 3.12 | 3.12 | 25 |
| 17. Ps. aeruginosa AK 109 | 12.5 | 6.25 | 6.25 | 6.25 | >100 |
| 18. Ps. aeruginosa AKR17 | >100 | >100 | 100 | >100 | >100 |
| 19. Ps. cepacia 23 | <0.006 | 0.025 | <0.006 | <0.006 | 0.025 |
| 20. A. calcoaceticus No. 4 | 0.2 | 0.1 | 0.2 | 0.39 | 0.39 |

| | Compound of Example 59 | | Compound of Example 60 | | Compound of Example 61 | |
|---|---|---|---|---|---|---|
| | (I) | (II) | (I) | (II) | DA | DB |
| 1. S. aureus 209P NIHJ-JC1 | 100 | 50 | 50 | 25 | 25 | 50 |
| 2. E. coli NIHJ JC2 | 1.56 | 3.12 | 1.56 | 0.78 | 0.78 | 3.12 |
| *3. E. coli CSH2 (RK1) | 0.025 | 0.025 | 0.05 | 0.0125 | 0.0125 | 0.05 |
| 4. K. pneumoniae PCI-602 | 0.0125 | 0.025 | 0.025 | <0.006 | <0.006 | 0.025 |
| *5. E. coli CSH(RE45) | 0.05 | 0.05 | 3.12 | 3.12 | 3.12 | 12.5 |
| *6. K. oxytoca GN10650 | 0.1 | 0.2 | 0.39 | 0.1 | 0.05 | 0.2 |
| *7. K. pneumoniae No. 42 | 0.2 | 0.2 | 0.39 | 0.1 | 0.1 | 0.39 |
| 8. P. vulgaris HX-19 | 0.025 | 0.025 | 0.025 | <0.006 | <0.006 | 0.05 |
| *9. P. vulgaris No. 33 | 0.1 | 0.05 | 0.1 | 0.025 | 0.025 | 0.2 |
| 10. S. marcescens IAM 1184 | 0.2 | 0.2 | 0.2 | 0.05 | 0.05 | 0.39 |
| 11. E. cloacae 963 | 0.39 | 0.2 | 0.78 | 0.2 | 0.39 | 0.78 |
| *12. E. cloacae Nek 39 | 0.2 | 0.2 | 0.39 | 0.2 | 0.1 | 0.39 |
| *13. E. coli GN5482 | 1.56 | 1.56 | 3.12 | 0.78 | 0.39 | 1.56 |
| *14. M. morganii GN5407 | 0.1 | — | 0.39 | 0.1 | 0.05 | 0.39 |
| *15. S. marcescens No. 16-2 | 1.56 | 0.78 | 3.12 | 0.78 | 0.78 | 3.12 |
| 16. Ps. aeruginosa IF03445 | 1.56 | 1.56 | 1.56 | 0.78 | 0.39 | 3.12 |
| 17. Ps. aeruginosa AK 109 | 1.56 | 1.56 | 1.56 | 1.56 | 0.39 | 1.56 |
| 18. Ps. aeruginosa AKR17 | 1.56 | 1.56 | 3.12 | 3.12 | 0.39 | 0.78 |
| 19. Ps. cepacia 23 | <0.006 | <0.006 | 0.0125 | <0.006 | <0.006 | <0.006 |
| 20. A. calcoaceticus No. 4 | 0.2 | 0.2 | 0.78 | 0.1 | 0.1 | 0.39 |

| | Compound of Ex. 62 | Compound of Ex. 63 | Compound of Ex. 64 | Compound of Ex. 65 | Compound of Ex. 66 | Compound of Ex. 67 |
|---|---|---|---|---|---|---|
| 1. S. aureus 209P NIHJ-JC1 | 1.56 | 3.12 | 25 | 3.12 | 25 | 3.12 |
| 2. E. coli NIHJ JC2 | 0.2 | 0.39 | 0.78 | 1.56 | 0.78 | 0.39 |
| *3. E. coli CSH2 (RK1) | 0.025 | 0.0125 | 0.0125 | 0.05 | 0.0125 | 0.0125 |
| 4. K. pneumoniae PCI-602 | <0.006 | <0.006 | 0.0125 | <0.006 | <0.006 | <0.006 |
| *5. E. coli CSH(RE45) | 0.05 | 0.1 | 0.025 | 0.05 | 0.05 | 0.1 |
| *6. K. oxytoca GN10650 | 3.12 | 3.12 | 0.1 | 0.2 | 0.1 | 1.56 |
| *7. K. pneumoniae No. 42 | 0.025 | 0.1 | 0.05 | 0.2 | 0.1 | 0.1 |
| 8. P. vulgaris HX-19 | <0.006 | 0.0125 | 0.0125 | 0.1 | 0.0125 | 0.0125 |
| *9. P. vulgaris No. 33 | 0.025 | 0.025 | 0.025 | 0.1 | 0.025 | 0.025 |
| 10. S. marcescens IAM 1184 | 0.025 | 0.1 | 0.1 | 0.2 | 0.05 | 0.1 |
| 11. E. cloacae 963 | 0.05 | 0.2 | 0.39 | 0.78 | 0.2 | 0.1 |
| *12. E. cloacae Nek 39 | 0.78 | 0.39 | 0.2 | 0.78 | 0.1 | 0.39 |
| *13. E. coli GN5482 | 1.56 | 1.56 | 3.12 | 6.25 | 1.56 | 3.12 |
| *14. M. morganii GN5407 | 0.1 | 0.1 | 0.1 | 0.2 | 0.1 | 0.05 |
| *15. S. marcescens No. 16-2 | 6.25 | 6.25 | 1.56 | 12.5 | 3.12 | 6.25 |
| 16. Ps. aeruginosa IF03445 | 1.56 | 1.56 | 0.78 | 1.56 | 0.78 | 1.56 |
| 17. Ps. aeruginosa AK 109 | 3.12 | 1.56 | 0.39 | 0.39 | 0.39 | 1.56 |
| 18. Ps. aeruginosa AKR17 | >100 | 100 | 1.56 | 0.2 | 3.12 | 50 |
| 19. Ps. cepacia 23 | <0.006 | 0.1 | <0.006 | <0.006 | <0.006 | 0.05 |
| 20. A. calcoaceticus No. 4 | 0.2 | 0.78 | 0.2 | 0.05 | 0.1 | 0.39 |

| | Reference Example 1 | Reference Example 2 | Reference Example 3 | Reference Example 4 | Reference Example 5 | Reference Example 6 |
|---|---|---|---|---|---|---|
| 1. S. aureus 209P NIHJ-JC1 | 0.39 | 0.78 | 6.25 | 6.25 | 0.39 | 3.12 |
| 2. E. coli NIHJ JC2 | 0.78 | 0.78 | 3.12 | 3.12 | 0.39 | 3.12 |
| *3. E. coli CSH2 (RK1) | 0.39 | 0.78 | 1.56 | 0.78 | 0.2 | 3.12 |
| 4. K. pneumoniae PCI-602 | 0.0125 | 0.0125 | 0.1 | 0.1 | 0.0125 | 0.1 |
| *5. E. coli CSH(RE45) | 0.39 | 0.39 | 1.56 | 0.78 | 0.2 | 3.12 |
| *6. K. oxytoca GN10650 | 6.25 | 25 | 3.12 | 1.56 | 6.25 | 6.25 |
| *7. K. pneumoniae No. 42 | 1.56 | 1.56 | 3.12 | 1.56 | 0.78 | 6.25 |
| 8. P. vulgaris HX-19 | <0.006 | <0.006 | <0.006 | 0.1 | 0.0125 | <0.006 |
| *9. P. vulgaris No. 33 | 0.78 | 0.78 | 0.39 | 0.2 | 0.39 | 0.39 |
| 10. S. marcescens IAM 1184 | 1.56 | 0.78 | 1.56 | 0.78 | 0.78 | 1.56 |
| 11. E. cloacae 963 | 1.56 | 1.56 | 6.25 | 3.12 | 0.78 | 6.25 |
| *12. E. cloacae Nek 39 | 3.12 | 6.25 | 25 | 12.5 | 3.12 | 50 |
| *13. E. coli GN5482 | 0.78 | 0.78 | 3.12 | 1.56 | 0.39 | 3.12 |
| *14. M. morganii GN5407 | 0.78 | 0.78 | 1.56 | 0.78 | 0.78 | 6.25 |
| *15. S. marcescens No. 16-2 | 6.25 | 25 | 25 | 12.5 | 3.12 | 12.5 |
| 16. Ps. aeruginosa IF03445 | >100 | 100 | 50 | 25 | 50 | 50 |
| 17. Ps. aeruginosa AK 109 | 50 | 50 | 50 | 12.5 | 50 | 100 |
| 18. Ps. aeruginosa AKR17 | >100 | >100 | >100 | >100 | >100 | >100 |
| 19. Ps. cepacia 23 | 12.5 | 12.5 | — | — | 3.12 | 12.5 |

TABLE A-continued

| Test microorganism | Minimum Inhibitory Concentration (MIC: μg/ml) | | | | | |
|---|---|---|---|---|---|---|
| 20. A. calcoaceticus No. 4 | 100 | 50 | 100 | 25 | 3.12 | 6.25 |

| | Reference Example 7 | Reference Example 8 | Reference Example 9 | Reference Example 10 | Reference Example 11 | Reference Example 12 |
|---|---|---|---|---|---|---|
| 1. S. aureus 209P NIHJ-JC1 | 0.39 | 6.25 | 0.1 | 0.2 | 3.12 | 3.12 |
| 2. E. coli NIHJ JC2 | 0.39 | 3.12 | 0.78 | 0.78 | 3.12 | 3.12 |
| *3. E. coli CSH2 (RK1) | 0.2 | 0.78 | 0.39 | 0.39 | 1.56 | 1.56 |
| 4. K. pneumoniae PCI-602 | <0.006 | 0.1 | <0.006 | <0.006 | 0.1 | 0.05 |
| *5. E. coli CSH(RE45) | 0.2 | 0.78 | 0.78 | 0.78 | 1.56 | 1.56 |
| *6. K. oxytoca GN10650 | 3.12 | 6.25 | 3.12 | 3.12 | 3.12 | 1.56 |
| *7. K. pneumoniae No. 42 | 1.56 | 3.12 | 1.56 | 1.56 | 3.12 | 3.12 |
| 8. P. vulgaris HX-19 | <0.006 | <0.006 | <0.006 | <0.006 | <0.006 | <0.006 |
| *9. P. vulgaris No. 33 | 1.56 | 0.2 | 0.78 | 0.78 | 0.78 | 0.39 |
| 10. S. marcescens IAM 1184 | 0.39 | 0.78 | 0.39 | 0.78 | 1.56 | 0.78 |
| 11. E. cloacae 963 | 1.56 | 6.25 | 1.56 | 1.56 | 6.2 | 3.12 |
| *12. E. cloacae Nek 39 | 3.12 | 25 | 3.12 | 3.12 | 12.5 | 12.5 |
| *13. E. coli GN5482 | 0.78 | 3.12 | 0.39 | 0.39 | 1.56 | 1.56 |
| *14. M. morganii GN5407 | 0.78 | 1.56 | 0.78 | 0.78 | 1.56 | 1.56 |
| *15. S. marcescens No. 16-2 | 3.12 | 6.25 | 3.12 | 3.12 | 6.25 | 12.5 |
| 16. Ps. aeruginosa IF03445 | 25 | 25 | 25 | 6.25 | 12.5 | 50 |
| 17. Ps. aeruginosa AK 109 | 25 | 25 | 25 | 12.5 | 50 | 25 |
| 18. Ps. aeruginosa AKR17 | >100 | >100 | >100 | >100 | >100 | >100 |
| 19. Ps. cepacia 23 | 3.12 | 6.25 | 3.12 | 3.12 | 12.5 | 3.12 |
| 20. A. calcoaceticus No. 4 | 1.56 | 3.12 | 25 | 50 | >100 | 100 |

| | Reference Example 13 | Reference Example 14 | Reference Example 15 | Reference Example 16 | Reference Example 17 | Reference Example 18 |
|---|---|---|---|---|---|---|
| 1. S. aureus 209P NIHJ-JC1 | 0.39 | 50 | 3.12 | 50 | 3.12 | 3.12 |
| 2. E. coli NIHJ JC2 | 6.25 | 1.56 | 0.78 | 6.25 | 0.39 | 0.78 |
| *3. E. coli CSH2 (RK1) | 1.56 | 1.56 | 0.39 | 6.25 | 0.39 | 0.78 |
| 4. K. pneumoniae PCI-602 | 0.05 | 0.2 | 0.2 | 1.56 | 0.1 | 0.2 |
| *5. E. coli CSH(RE45) | 6.25 | 1.56 | 0.78 | 3.12 | 0.78 | 1.56 |
| *6. K. oxytoca GN10650 | 25 | 1.56 | 25 | 3.12 | 25 | 25 |
| *7. K. pneumoniae No. 42 | 6.25 | 1.56 | 0.78 | 3.12 | 0.78 | 0.78 |
| 8. P. vulgaris HX-19 | 0.05 | <0.006 | <0.006 | <0.006 | <0.006 | <0.006 |
| *9. P. vulgaris No. 33 | 3.12 | 0.025 | 0.2 | 0.2 | 0.1 | 0.1 |
| 10. S. marcescens IAM 1184 | 3.12 | 0.1 | 0.78 | 1.56 | 0.39 | 0.78 |
| 11. E. cloacae 963 | 12.5 | 1.56 | 0.39 | 6.25 | 0.39 | 0.78 |
| *12. E. cloacae Nek 39 | 25 | 12.5 | 12.5 | 25 | 12.5 | 12.5 |
| *13. E. coli GN5482 | 3.12 | 3.12 | 3.12 | 6.25 | 3.12 | 3.12 |
| *14. M. morganii GN5407 | 6.25 | 0.2 | 0.39 | 1.56 | 0.39 | 0.39 |
| *15. S. marcescens No. 16-2 | 50 | 25 | 50 | 50 | 100 | 100 |
| 16. Ps. aeruginosa IF03445 | >100 | 12.5 | 100 | 50 | 50 | 100 |
| 17. Ps. aeruginosa AK 109 | 100 | 12.5 | 100 | 50 | 50 | >100 |
| 18. Ps. aeruginosa AKR17 | >100 | >100 | >100 | >100 | >100 | >100 |
| 19. Ps. cepacia 23 | 12.5 | 0.78 | 6.25 | 6.25 | 6.25 | 12.5 |
| 20. A. calcoaceticus No. 4 | 100 | 50 | 100 | >100 | 100 | 100 |

| | Reference Example 19 | Reference Example 20 | Reference Example 21 | Reference Example 22 | Reference Example 23 | Reference Example 24 | ceftazidime | cefotaxime |
|---|---|---|---|---|---|---|---|---|
| 1. S. aureus 209P NIHJ-JC1 | 50 | 50 | 0.39 | 6.25 | 0.2 | 6.25 | 6.25 | 1.56 |
| 2. E. coli NIHJ JC2 | 3.12 | 3.12 | 1.56 | 12.5 | 1.56 | 12.5 | 0.1 | 0.05 |
| *3. E. coli CSH2 (RK1) | 1.56 | 3.12 | 0.78 | 3.12 | 0.78 | 3.12 | 0.1 | 0.0125 |
| 4. K. pneumoniae PCI-602 | 0.39 | 1.56 | 0.0125 | 0.1 | 0.0125 | 0.2 | 0.025 | <0.006 |
| *5. E. coli CSH(RE45) | 1.56 | 3.12 | 1.56 | 3.12 | 0.78 | 3.12 | 0.2 | 0.1 |
| *6. K. oxytoca GN10650 | 1.56 | 3.12 | 12.5 | 6.25 | 25 | 6.25 | 0.1 | 0.39 |
| *7. K. pneumoniae No. 42 | 1.56 | 3.12 | 3.12 | 12.5 | 3.12 | 12.5 | 0.39 | 0.05 |
| 8. P. vulgaris HX-19 | <0.006 | <0.006 | 0.0125 | <0.006 | <0.006 | <0.006 | 0.025 | <0.006 |
| *9. P. vulgaris No. 33 | 0.05 | 0.100 | 0.78 | 0.78 | 0.78 | 0.39 | 0.05 | 0.025 |
| 10. S. marcescens IAM 1184 | 0.78 | 1.56 | 0.78 | 3.12 | 0.78 | 3.12 | <0.006 | 0.0125 |
| 11. E. cloacae 963 | 3.12 | 6.25 | 3.12 | 12.5 | 3.12 | 12.5 | 0.1 | 0.05 |
| *12. E. cloacae Nek 39 | 6.25 | 25 | 6.25 | 25 | 6.25 | 25 | 1.56 | 1.56 |
| *13. E. coli GN5482 | 3.12 | 6.25 | 0.78 | 3.12 | 0.78 | 3.12 | 1.56 | 0.39 |
| *14. M. morganii GN5407 | 1.56 | 3.12 | 1.56 | 6.25 | 1.56 | 6.25 | 0.1 | 0.05 |
| *15. S. marcescens No. 16-2 | 25 | 100 | 6.25 | 25 | 25 | 25 | 1.56 | 6.25 |
| 16. Ps. aeruginosa IF03445 | 12.5 | 25 | 50 | 50 | 50 | 25 | 1.56 | 2.5 |
| 17. Ps. aeruginosa AK 109 | 6.25 | 25 | 50 | 50 | 50 | 25 | 0.78 | 12.5 |
| 18. Ps. aeruginosa AKR17 | 25 | >100 | >100 | >100 | >100 | >100 | >100 | >100 |
| 19. Ps. cepacia 23 | 0.2 | 6.25 | 0.78 | 12.5 | 3.12 | 6.25 | 0.78 | 6.25 |
| 20. A. calcoaceticus No. 4 | 6.25 | >100 | 12.5 | >100 | 50 | >100 | 6.25 | 25 |

β-Lactamase-producing strains
DA - Diastereomer A
DB - Diastereomer B

Thus the compounds of the present invention exhibit excellent antibacterial activities against sensitive and resistant Gram-negative bacteria particularly glucose non-fermentative Gram-negative rods, such as Pseudomonas aeruginosa, Pseudomonas cepacia, Pseudomonas Maltophilia, and Acinetobacter calcoaceticus.

Further, with respect to the compound of EXAMPLES 11, 34, 44, 59, 64 and 76, the β-lactamase inducibility was measured by *Enterobacter cloacae* GN 5797, whereby no substantial β-lactamase-inducing activity was observed. The assay method for induction of β-lactamase by β-latam antibiotics was as follows:

The test organism, *Enterobacter cloacae* GN 5797, was grown overnight in Mueller Hinton broth (Dlfco Laboratories, Detroit, Mich.) at 37° C. The culture was diluted 10-fold into 20 ml of the flesh medium and incubated with shaking at 37° C. After 2 hours of incubation, antibiotics were added to final concentrations of 50 μg/ml, 10 μg/ml and 1 μg/ml, and the incubation was continued. At 1 hour intervals after the addition of antibiotic, 3 ml of sample was taken, and immediately added with 0.1 ml of 50 mM sodium azide. The cells were harvested and washed with 50 mM phosphate buffer (ph 7.0). The cells were suspended in 5 ml of 50 mM phosphate buffer and disrupted with a sonicater in an ice-water bath. The broken cells were centrifuged at 16,500 G for 40 minutes at 4° C., and the resulting supernatant fluid was used as the crude enzyme. β-Lactamase activity was determined by a sopectrophotometric method (Antmicrob. Agents Chemother. 17, 355–358, 1980) with cephaloridine as substrate. The concentration of protein was determined by the method of Lowry (J. Biol. Chem. 193, 265–275, 1951). The compounds of the present invention exhibit excellent pharmacokinetics. As a representative example, the compound of EXAMPLE 50 was administered to mice by means of subcutaneous administration, and the concentration in the blood was measured. The measurement was conducted as follows:

Four week old ddY type male mice (weight: 19–22 g) were used in a group of 5 animals. The test compound was dissolved in physiological sodium chloride solution to obtain a formulation having a concentration of 2 g/ml. The formulation was subcutaneously administered to the mice in an amount of 0.1 ml/10 g of the weight. Upon expiry of each of the periods of 7.5, 15, 30, 60, 120 and 240 minutes after the administration, the blood was sampled from the heart of the mice by means of a syringe treated with heparin. The concentration in the blood upon expiry of each period is shown in the following Table. Ceftazidime was used as a comparative compound. Further, the antibacterial activities of the sample diluted by plasma to have an appropriate concentration were measured by means of the paper disk method against Morganella morgaini IFO 3843 as the examined bacterium.

TABLE B

| Test compound | Dose (mg/kg) | Concentration in blood |||||| 
|---|---|---|---|---|---|---|---|
| | | Concentrated in blood (μg/ml) Period after administration (min.) ||||||
| | | 7.5 | 15 | 30 | 60 | 120 | 240 |
| EXAMPLE 50 | 20 | 60.5 | 67 | 52.3 | 18.5 | 3.1 | 0,22 |
| Ceftazidime | 20 | 25.4 | 24.1 | 17.3 | 3.3 | 0.2 | — |

It is clear from the above Table that according to the compound of the present invention, a high concentration in the blood is promptly obtained as compared with ceftazidime.

Thus, the compounds of the formula I and non-toxic salts and physiologically hydrolyzable non-toxic esters thereof are useful as antibacterial agents.

The compounds of the present invention may be mixed with a carrier of solid or liquid excipient, and may be used in the form of a pharmaceutical formulation suitable for parenteral administration, oral administration or external administration. As the pharmaceutical formulations, there may be mentioned liquid formulations such as injection solutions, syrups and emulsions, solid formulations such as tablets, capsules and granules and formulations for external application such as ointments and suppositories. Further, these formulations may contain commonly employed additives such as assisting agents, stabilizers, wetting agents, emulsifying agents, absorption-promoting agents or surfactants. As such additives, distilled water for injection, a Ringer solution, glucose, sucrose syrup, gelatin, edible oil, coconut oil, ethylene glycol, sucrose, corn starch, magnesium stearate and talc, may be mentioned.

Further, the compounds of the present invention can be used as antibacterial agents for the treatment of human infect:ous diseases caused by Gram-negative bacteria including glucose non-fermentative Gram-negative rods such as Pseudomonas aeruginosa, Pseudomonas cepacia, Pseudomonas maltophilia and Acinetobacter calcoaceticus. The dose may vary depending upon the age, sex and condition of the patient, and is usually within a range of from 1 to 100 mg/kg per day. It is preferred to administer a daily dose of from 5 to 30 mg/kg in 2 to 4 times.

The compounds of the present invention are novel compounds undisclosed in literatures. They have strong antibacterial activities against sensitive and resistant Gram-positive bacteria and Gram-negative bacteria, particularly glucose non-fermentative Gram-negative rods including Pseudomonas aeruginosa, excellent stability against β-lactamase and low β-lactamase inducing activity, and thus they are effective as antibacterial agents.

Particularly, the compound of the present invention having a disubstituted phenyl substituted heterocyclic thiomethyl or disubstituted benzene ring-fused thiomethyl group which has an adjacent dihydroxyl or acetoxy group at the 3-position of the cephem nucleus, exhibit unexpected strong antibacterial activities against sensitive and resistant Gram-negative rods, as compared with the compounds wherein the phenyl nucleus or fused benzene nucleus is unsubstituted or monosubstituted (compounds of Reference Examples).

EXAMPLE 1

Preparation of sodium 7β-[2-(2-aminothiazol-4-yl)-2-methoxyiminoacetamido]-3-[5-(3, 4dihydroxyphenyl)-1,3,4-oxadiazol-2-yl]thiomethyl-3-cephem-4-carboxylate (syn-isomer)

(A) 1.0g (1.1 mmol) of benzhydryl 3-iodomethyl-7β-[2-methoxyimino-2-(2-tritylaminothiazol-4-yl)acetamido]-3-cephem-4-carboxylate (syn-isomer) was dissolved in 10 ml of N,N-dimethylformamide, and 0.34g (1.1 mmol) of 2-mercapto-5-[3,4-di(2-methoxyethoxymethoxy)phenyl]-1,3,4oxadiazole was added thereto. The mixture was stirred at room temperature for 2 hours. The solvent was distilled off under-reduced pressure, and the residue thus obtained was purified by silica gel column chromatography (Wakogel C-300). The fraction (ethyl acetate:hexane=3:1) containing the desired compound was concentrated to obtain 0.73g (yield: 61%) of benzhydryl 3-{5-[3,4-di(2-methoxyethoxymethoxy)phenyl]-1,3,4-oxadiazol-2-yl}-thiomethyl-7β-[2-methoxyimino-2-(2-tritylaminothiazol-4- yl)acetamido]-3-cephem-4-carboxylate (syn-isomer) as a foamy substance.

NMR(DMSO-$d_6$)δ: 3.23(6H,s), 3.50(6H,m), 3.80(4H,m), 4.30(2H,m), 5.23(1H,d,J=5Hz), 5.25(4H,m), 5,82(1H,dd,J=5 and 7Hz), 6.80(1H,s), 6.88(1H,s), 7.00-7 90(28H,m), 9.00(1H,br s), 9.62(1H,br d,J=7Hz).

(B) 0.73 g (0.65 mmol) of the compound obtained in the above reaction (A) was dissolved in a solution comprising 3,6 methylene chloride and 0.7 ml of anisole, and 3.6 ml of trifluoroacetic acid was dropwise added thereto at 0° C. The mixture was stirred at room temperature for 1 hour. The solvent was distilled off under reduced pressure, and diethyl ether was added to the residue under cooling with ice. The resulting precipitates were collected by filtration and suspended in water. The suspension was adjusted to pH6.5 with a saturated sodium hydrogencarbonate aqueous solution, and insoluble substances were filtered off. The filtrate was subjected to ODS silica gel column chromatography (LC Sorb RP-18, manufactured by Kemco Co.). The fraction (10% methanol aqueous solution) containing the desired compound was concentrated under reduced pressure, and then freeze-dried to obtain 156 mg (yield: 40%) of the above identified compound.

MP: 175° C. (decomposed)

IR(KBr)cm$^{-1}$: 3420, 1762, 1602

NMR(DMSO-$d_6$)δ: 3.53(2H,m), 3.83(3H,s), 4.37(2H,m), 5.00(1H,d,J=5Hz), 5.58(1H,m), 6.72(1H,s), 6.74(1H,d,J=7Hz), 7.18(1H,br d,J=7Hz), 7.22(1H,br s)

EXAMPLE 2

Preparation of sodium 7β-[2-(2-aminothiazol-4-yl)-2-methoxyiminoacetamido]-3-[5-(3, 4-dihydroxyphenyl)-1,3,4-oxadiazol-2-yl]thiomethyl-3-cephem-4-carboxylate (syn-isomer)

1.25 g (2.50 mmol) of 7β-[2-(2-aminothiazol-4-yl)-2-methoxyiminoacetamido]cephalosporanic acid formate (syn-isomer) and 0.63 g (3.00 mmol) of 5-(3,4-dihydroxyphenyl)-2-mercapto-1,3, 4-oxadiazole were suspended in 25 ml of water and adjusted to pH6.5 with sodium hydrogencarbonate. To the solution, 25 ml of acetone was added and stirred at a temperature of from 65° to 70° C. for 4 hours. The reaction solution was concentrated under reduced pressure, and the concentrated aqueous solution was purified by ODS column chromatography (LC Sorb RP-18, manufactured by Kemco Co.). The fraction (40% methanol aqueous solution) containing the desired compound was concentrated to obtain 119 mg (yield: 7.6%) of the above identified compound. The IR and NMR absorption spectra of the compound were entirely the same as those of the compound of EXAMPLE 1.

EXAMPLE 3

Sodium 7β-[2-(2-aminothiazol-4-yl)-2-methoxyiminoacetamido]-3-[5-(3, 4-dihydroxyphenyl)-1,3,4-oxadiazol-2-yl]thiomethyl-3-cephem-4-carboxylate (syn-isomer)

(A) a) 1.48 g (3.5 mmol) of 7β-amino-3-[5-(3,4-dihydroxyphenyl)-1,3,4-oxadiazol-2-yl) thiomethyl-3-cephem-4-carboxylic acid was suspended in 12 ml of methylene color: e, and 3.46 ml (14 mmol) of N,O-bis (trimethylsilyl)acetamide was added thereto. The mixture was refluxed for 45 minutes, and then cooled to −10° C.

b) 0.42 ml (4.5 mmol) of phosphorus oxychloride and 0.35 ml (4.5 mmol) of N,N-dimethylformamide were added to 1.3 ml of ethyl acetate at room temperature, and the mixture was stirred for 30 minutes. Then, 10 ml of methylene chloride was added thereto and cooled to 5° C. To the solution, 1.77 g (4 mmol) of 2-methoxyimino-2-(2-tritylaminothiazol-4-yl)acetic acid (syn-isomer)was added and stirred at 5° C. for 20 minutes. This solution was added to the solution prepared in the above reaction a) at once and stirred at the same temperature for 1 hour. The reaction solution was poured into 20 ml of cold water, and the oraganic layer was separated. The organic layer was washed with a saturated sodium chloride aqueous solution, then dried over anhydrous magnesium sulfate and concentrated under reduced pressure. To the oily residue ethyl ether was added and stirred for 30 minutes under cooling with ice to obtain 2.88 g (yield: 97%) of 3-[5-(3,4-dihydroxyphenyl)-1,3,4-oxadiazol-2-yl]thiomethyl-7β-[2-methoxyimino-2-(2-tritylaminothiazol-4-yl)acetamido]-3-cephem-4-carboxylic acid (syn-isomer) as a powdary substance.

IR(KBr)cm$^{-1}$: 3400, 1790, 1680, 1600, 1580

NMR(DMSO-$d_6$)δ: 3.70(2H,ABq), 3.94(3H,s), 4.35(2H,ABq), 5.15(1H,d,J=4.5Hz), 5.73(1H,dd,J=4.5 and 9Hz), 6.87(1H,s), 7.04(1H,d,J=10Hz), 7.15-7.70(17H,m), 9.68(1H,d,J=9Hz), 10.40(1H,br s), 11.85(3H,br s)

(B) To 1.48 g (1.75 mmol) of the compound obtained in the above reaction (A), 9 ml of a 99% formic acid and 0.71 ml of concentrated hydrochloric acid were added and stirred at the same temperature for 2.5 hours (gummy insoluble substances changed gradually to a yellow suspension). Insoluble substances were collected by filtration and washed with 1 ml of a 99% formic acid. The filtrate was added to 150 ml of diisopropyl ether and stirred at room temperature for 30 minutes. The resulting precipitates were collected by filtration and washed twice with 20 ml of diisopropyl ether to obtain 0.9 g (yield: 80%) of 7β-[2-(2-aminothiazol-4-yl)-2-methoxyiminoacetamido]-3[5-(3,4-dihydroxyphenyl)-1,3,4-oxadiazol-2-yl]-thiomethyl-3-cephem-4-carboxylic acid hydrochloride (syn-isomer)

IR(KBr)cm$^{-1}$: 3400, 1780, 1720, 1680, 1630

NMR(DMSO-$d_6$)δ: 3.73(2H,ABq), 3.97(3H,s), 4,35(2H,ABq), 5.17(1H,d,J=4.5Hz), 5.77(1H,dd,J=4.5 and 9.0Hz), 6.93(1H,d,J=9.0Hz), 6.97(1H,s), 7.10-7.40(2H,m), 9.80(6H,br s)

(C) 670 mg (1.04 mmol) of the compound obtained in the above reaction (B) was suspended in 27 ml of water and adjusted to pH7 with a saturated sodium hydrogencarbonate, followed by filtration The filtrate was adjusted to pH3 with 6N hydrochloric acid under cooling with ice and stirred for one hour The precipitates were collected by filtration and washed twice with 6 ml of water. The precipitates were dried under reduced pressure to obtain 510 mg (yield 81%) of 7β-[2-(2-aminothiazol-4-yl)-2-methoxyiminoacetamido]-3-[5-(3, 4-dihydroxyphenyl)-1,3,4-oxadiazol-2-yl]thiomethyl-3--cephem--carboxylic acid (syn-isomer) as white powders MP: 175°-180° C. (decomposed)

IR(KBr)cm$^{-1}$: 3400, 1770, 1670, 1620

NMR(DMSO-$d_6$)δ: 3.73(2H,ABq), 3.86(3H,s), 4.34(2H,ABq), 5.15(1H,d,J=4.5Hz), 5.78(1H,dd,J=4.5 and 9.0Hz), 6.75(1H,s), 6.90(1H,d,J=9 0Hz), 7.20-7.50(2H,m), 9.20-10 00(2H,br s)

(D) 121 mg (0.2 mmol) of the compound obtained by the above reaction (C) was suspended in 1.21 ml of water, and 25.2 mg (0.3 mmol) of sodium hydrogencarbonate was added thereto, followed by filtration. The filtrate was allowed to stand at room temperature for 1 hour, and the precipitates were collected by filtration. The precipites were washed with 0.5 ml of water and dried under reduced pressure to obtain 40 mg (yield: 32%) of the above identified compound as white powders The IR and NMR absorption spectra of the compound are entirely the same as those of the compound of EXAMPLE 1.

EXAMPLE 4

Preparation of sodium 3-[5-(3,4-diacetoxyphenyl)-1,3,4-oxadiazol-2-yl]thiomethyl-7β-[2-(2-thiazol-4-yl)-2-methoxyiminoacetamido]-3-cephem-4carboxylate (syn-isomer)

(A) 1.0 g (1.1 mmol) of benzhydryl 3-iodomethyl-7β-methoxyimino-2-( 2-tritylaminothiazol-4-yl)acetamido]-3-cephem-4-carboxylate (syn-isomer) was dissolved in 10 ml of N,N-dimethylformamide, and 0.34 g (1.1 mmol) of 5-(3,4-dihydroxyphenyl)-2-mercapto-1,3,4-oxadiazole was added thereto. The mixture was stirred at room temperature for 2 hours. The solvent was distilled off under reduced pressure, and to the residue 2.5 ml of acetic anhydride and 2.5 ml of pyridine were added and dissolved. The mixture was allowed to stand at room temperature for 1 hour, and the solvent was distilled off again. The residue thus obtained was purified by silica gel column chromatography (Wakogel C-300), and the fraction (ethyl acetate:hexane=1:1) containing the desired compound was concentrated to obtain 0.74 g (yield: 63%) of benzhydryl 3-[5-(3,4-diacetoxyphenyl)-1,3,4-oxadiazol-2-yl]thiomethyl-7β-[2-methoxyimino-(2-tritylaminothiazol-4-yl) acetamido]-3-cephem-4carboxylate (syn-isomer) as a foamy substance.

NMR(DMSO-d$_6$)δ: 2.36(6H,s), 3.80(2H,m), 3.86(3H,s), 4.10-4.60(2H,m), 5.22(1H,d,J=5Hz), 5.80(1H,m), 6.77(1H,s), 6.90(1H,s),

EXAMPLE 5

Preparation of sodium 7β-[2-(2-aminothiazol-4-yl)-2-ethoxyiminoacetamido]-3-[5-(3, 4-dihydroxyphenyl)-1,3,4-oxadiazol-2-yl]thiomethyl-3-cephem-4-carboxylate (syn-isomer)

The same operation as in EXAMPLE 1 was conducted by using 1.0 g (1.1 mmol) of 7β-[2-ethoxyimino-2-(2-tritylaminothiazol-4-yl) acetamido]-3-iodomethyl-3-cephem-4-carboxylate (syn-isomer) and 0.34 g (1.1 mmol) of 2-mercapto-5-[3,4-di(2-methoxyethoxymethoxy)phenyl]-1,3,4-oxadiazole, whereby 95 mg (yield: 13.7%) of the above identified compounds was obtained.

MP: 165° C. (decomposed)
IR(KBr)cm$^{-1}$: 3400, 1764, 1670, 1610
NMR(DMSO-d$_6$)δ: 1.25(3H,t,J=8Hz), 3.20-3.90(2H,m), 4.10(2H,q,J=8Hz), 5.00(1H,d,J=5Hz), 5.62(1H,m), 6.72(1H,s), 6.85(1H,d,J=8Hz), 7.20(1H,br d,J=8Hz), 7.28(1H,br s)

EXAMPLE 6

Preparation of sodium 3-[5-(3,4-diacetoxyphenyl)-1,3,4-oxadiazol-2-yl]thiomethyl-7β-[2-(2-aminothiazol-4-yl)-2-ethoxyiminoacetamido ]-3-cephem-4-carboxylate (syn-isomer)

The same operation as in EXAMPLE 4 was conducted by using 2.0 g (2.11 mmol) of benzhydryl 7β-[2-ethoxyimino-2-(2-tritylaiminothiazol-4-yl) acetamido]-3-iodomethyl-3-cephem-4-carboxylate (syn-isomer) and 0.89 g 7.10–7.70(28H,m), 8.80(1H,br s), 9.60(1H,.-br d,J=8Hz)

(B) 0.74 g (0.67 mmol) of the compound obtained by the above reaction (A) was dissolved in a solution comprising 4.0 ml of methylene chloride and 0.8 ml of anisole, and 4.0 ml of trifluoroacetic acid was dropwise added at 0° C. The mixture was stirred at room temperature for 1 hour. The solvent was distilled off under reduced pressure, and diethyl ether was added to the residue under cooling with ice. The resulting precipitates were collected by filtration and suspended in water. The suspension was adjusted to pH6.5 with a saturated sodium hydrogencarbonate aqueous solution, and insoluble substances were filtered off. The filtrate was subjected to ODS silica gel column chromatography (LC-Sorb RP-18, manufactured by Kemco Co.). The fraction (40% methanol aqueous solution) containing the desired compound was concentrated under reduced pressure, and then freeze-dried to obtain 142 mg (yield: 30%) of the above identified compound.

MP: 170° C. (decomposed)
IR(KBr)cm$^{-1}$: 3450, 1772, 1620
NMR(DMSO-d$_6$)δ: 2.33(6H,s), 3.56(2H,m), 3.83(3H,s), 4.40(2H,m), 5.00(1H,d,J=5Hz), 5.60(1H,dd,J=5 and 8Hz), 6.72(1H,s), 7.50(1H,d,J=8Hz), 7.89(1H,br s), 7.90(1H,br d,J=8Hz), 9,50(1H,br d,J=8Hz) (4.22 mmol) of 5-(3,4-dihydroxyphenyl)-2-mercapto-1,3,4-oxadiazol whereby 291 mg yield; 21.4%) of the above identified compound was obtained.

MP: 175° C. (decomposed)
IR(KBr)cm$^{-1}$: 3430, 1772, 1620
NMR(DMSO-d$_6$)δ: 1.23(3H,t,J=8Hz), 2,33(6H,s), 3.60(2H,m), 4.12(2H,q,J=8Hz), 4.43(2H,m), 5.04(1H,d,J=5Hz), 5.60(1H,dd,J=5 and 8Hz), 6.70(1H,s), 7.20(2H,br s), 7.50(1H,d,J=14Hz), 7.88(1H,s), 7,89(1H,br d,J=14Hz), 9.44(1H,br d,J=8Hz)

EXAMPLE 7

Preparation of sodium 7β-[2-(2-aminothiazol-4-yl)-2-isopropoxyiminoacetamido]-3-[5-(3, 4-dihydroxyphenyl)-1,3,4-oxadiazol-2-yl]thiomethyl-3-cephem-4-carboxylate (syn-isomer)

The same operation as in EXAMPLE 1 was conducted by using 1.0 g (1.0 mmol) of benzhydryl 3-iodomethyl-7β-[2-isopropoxyimino-2-(2-tritylaminothiazol-acetamido]-3-cephem-4-carboxylate (syn-isomer) and 0.40 g (1.2 mmol) of 2-mercapto-5-[3,4-di(2-methoxyethoxymethoxy)phenyl]-1,3,4-oxadiazole, whereby 56 mg (yield: 8.2%) of the above identified compound was obtained.

MP: 195° C. (decomposed)
IR(KBr)cm$^{-1}$: 3430, 1762, 1615

NMR(DMSO-d$_6$)δ: 1.22(6H,d,J=6Hz), 3.53(2H,m), 4.15–4.50(3H,m), 5.01(1H,d,J=5Hz), 5.69(1H,s), 6.92(1H,d,J=8Hz), 7.20–7.40(3H,m)

EXAMPLE 8

Preparation of sodium 7β-[2-allyloxyimino-2-(2-aminothiazol-4-yl)acetamido]-3-[5-(3,4-dihydroxyphenyl)-1,3,4-oxadiazol-2-yl]thiomethyl-3-cephem-4carboxylate (syn-isomer)

The same operation as in EXAMPLE 1 was conducted by using 1.0 g (1.0 mmol) of benzhydryl 7β-[2-allyloxyimino-2-(2-tritylaminothiazol-4-yl)acetamido]-3-iodomethyl-3-cephem-4-carboxylate and 0.40 g (1.2 mmol) of 2-mercapto-5-[3,4-di(2-methoxyethoxymethoxy)phenyl]-1,3,4-oxadiazole, whereby 150 mg (yield: 18.2%) of the above identified compounds was obtained.

MP: 180° C.

IR(KBr)cm$^{-1}$: 3420, 1765, 1660, 1600

NMR(DMSO-d$_6$)δ: 3.54(2H,m), 4,38(2H,m), 4.60(2H,br d,J=5Hz), 5.00(1H,d,J=5Hz), 5.05–5.50(2H,m), 5.60(1H,d,J=5Hz), 5.70–6.10(1H,m), 6.72(1H,s), 6.83(1H,d,J=9Hz), 7.22(1H,d,J=9Hz), 7.29(1H,s)

EXAMPLE 9

Preparaton of sodium 7β-[2-(2-aminothiazol-4-yl)-2-(2-propynyloxyimino)acetamido]-3-[5-(3,4-dihydroxyphenyl)-1,3,4-oxadiazol-2-yl]thiomethyl-3-cephem-4carboxylate (syn-isomer)

The same operation as in EXAMPLE 1 was conducted by using 1.0 g (1.0 mmol) of benzhydryl 3-iodomethyl-7β-[2-(2-propynyloxyimino)-2-(2-tritylaminothiazol-4-yl)acetamido]-3-cephem-4-carboxylate (syn-isomer) and 0.4 g (1.2 mmol) of 2-mercapto-5-[3,4-di(2-methoxyethoxymethoxy)phenyl]-1,3,4-oxadiazole, whereby 113 mg (yield: 16.6%) of the above identified compound was obtained.

MP: 155° C. (decomposed)

IR(KBr)cm$^{-1}$: 3440, 1765, 1675, 1615

NMR(DMSO-d$_6$)δ: 2.50(1H,br s), 3.50(2H,m), 4.36(2H,m), 4.67(2H,br s), 5.00(1H,d,J=5Hz), 5.60(1H,m), 6.73(1H,s), 6.92(1H,d,J=7Hz), 7.24(1H,br d,J=7Hz), 7.35(1H,br s), 9.58(1H,br d,J=8Hz)

EXAMPLE 10

Preparation of disodium 78-[2-(2-aminothiazol-4-yl)-2-carboxylatemethoxyiminoacetamido]-3-[5-(3,4-dihydroxyphenyl)-1,3,4-oxadiazol-2-yl]thiomethyl-3-cephem-4-carboxylate (syn-isomer)

The same operation as in EXAMPLE 1 was conducted by using 1.0 g (0.88 mmol) of benzhydryl 7β-[2-benzhydryloxycarbonylmethoxyimino-2-(2-tritylaminothiazol-4yl)acetamido]-3-iodomethyl-3-cephem-4-carboxylate (syn-isomer) and 0.28 g (0.88 mmol) of 2-mercapto-5-[3,4di(2-methoxyethoxymethoxy)phenyl]-1,3,4-oxadiazole, whereby 172 mg (yield: 29.9%) of the above identified compound was obtained.

MP: 180° C. (decomposed)

KBr)cm$^{-1}$: 3420, 1762, 1602

NMR(DMSO-d$_6$)δ: 3.55(2H,m), 3.90-4.60(3H,m), 5.02(1H,d,J=5Hz), 5.65(1H,m), 6.85(1H,s), 6.86(1H,d,J=7Hz), 7.30(3H,m)

EXAMPLE 11

Preparation of disodium 7β-[2-(2-aminothiazol-4-yl)-(1-carboxylate-1-methylethoxyimino)acetamido]-3-[5(3,4-dihydroxyphenyl)-1,3,4-oxadiazol-2-yl]thiomethyl-3-cephem-4-carboxylate (syn-isomer)

The same operation as in EXAMPLE 1 was conducted by using 1.2 g (1.0 mmol) of benzhydryl 7β-[2-(1-benzhydryloxycarbonyl-1-methylethoxyimino )-2-(2-tritylaminothiazol-4-yl) acetamido]-3-iodomethyl-3-cephem-4-carboxylate (syn-isomer) and 0.33 g (1.1 mmol) of 2-mercapto-5 [3,4-di(2-methoxyethoxymethoxy)phenyl]-1,3,4-oxadiazole, whereby 238 mg (yield: 34.4%) of the above identified compound was obtained.

MP: 185° C. (decomposed)

IR(KBr)cm$^{-1}$: 3420, 1770, 1600

NMR(DMSO-d$_6$)δ: 1.39(3H,br s), 1.47(3H,br s), 3.54(2H,m), 4.08(1H,br d,J=12Hz), 4.50(1H,br d,J=12Hz), 5.08(1H,d,J=6Hz), 5.70(1H,m), 6.69(1H,s), 6.77(1H,d,J=7Hz), 7.20(1H,br d,J=7Hz), 7.27(1H,br s)

EXAMPLE 12

Preparation of disodium 7β-[2-(2-aminothiazol-4-yl)-2-(1-carboxylate-1-cyclopropoxyimino)acetamido]-3-[5-(3,4-dihydroxvphenyl)-1,3,4-oxadiazol-2-vl]thiomethyl-3-cephem-4-carboxylate (syn-isomer)

The same operation as in EXAMPLE 1 was conducted by using 1.0 g (0.96 mmol) of benzhydryl 7β-[2-(1-tertbutoxycarbonyl-1-cyclopropoxyimino)-2-(2-tritylaminothiazol-4-yl) acetamidol]-3-iodomethyl-3-cephem-4-carboxylate (syn-isomer) and 0.30 g (1.0 mmol) of 2-mercapto-5-[3, 4-di(2-methoxyethoxymethoxy)phenyl]-1,3,4-oxadiazole, whereby 146 mg (yield: 21.7%) of the above identified compound was obtained.

MP: 155° C. (decomposed)

IR(KBr)cm$^{-1}$: 3420, 1765, 1600

NMR(DMSO-d$_6$)δ: 1.16(4H,m), 3.58(2H,m), 4.18(1H,d,J=12Hz), 4.45(1H,d,J=12Hz), 5.05(1H,d,J=4Hz), 5.65(1H,m), 6.75(1H,d,J=10Hz), 6.83(1H,s), 7.22(3H,m)

EXAMPLE 13

Preparation of sodium 7β-[2-(2-aminothiazol-4-yl)-2-benzyloxyiminoacetamido]-3-[5-(3, 4-dihydroxyphenvl)-1,3,4-oxadiazol-2-yl]thiomethyl-3-cephem-4-carboxylate (syn-isomer)

The same operation as in EXAMPLE 1 was conducted by using 0.65 g (0.67 mmol) of benzhydryl 7β-[2-benzyloxyimino-2-( 2-tritylaminothiazol-4-yl)acetamido]-3-chloromethyl-3-cephem-4-carboxylate (syn-isomer) and 0.41 g (1.34-mmol) of 2-mercapto-5-[3,.4-di(2-methoxyethoxymethoxy) phenyl]-1,3,4-oxadiazole, whereby 30 mg (yield: 12.4%) of the above identified compound was obtained.

MP: 170° C. (decomposed)

IR(KBr)cm$^{-1}$: 3400, 1765, 1605

NMR(DMSO-d$_6$)δ: 3.40(1H,br d,J=18Hz), 3.65(1H,br d,J=18Hz), 4.39(2H,m), 5.00(1H,d,J=6Hz), 5.13(2H,br s), 5.68(1H,m), 6.74(1H,s), 6.90(1H,d,J=8Hz), 7.33(7H,m)

EXAMPLE 14

Preparation of sodium 7β-[2-(2-aminothiazol-4-yl)-2-(3,4-dihydroxybenzyloxyimino) acetamido]-3-[5-(3,4-dihydroxyphenyl)-1,3, 4-oxadiazol-2-yl]thiomethyl-3-cephem-4-carboxylate (syn-isomer)

The same operation as in EXAMPLE 1 was conducted by using 1.0 g (0.82 mmol) of benzhydryl 3-iodomethyl-7β-{2-[3,4-di(2-methoxyethoxymethoxy)-benzyloxyimino]-2-(2-tritylaminothiazol-4-yl) acetamido)-3-cephem-4-carboxylate (syn-isomer) and 0.25 g (1.1 mmol) of 5-(3, 4-dihydroxyphenyl)-2-mercapto-1,3,4-oxadiazole, whereby 345 mg (yield: 52%) of the above identified compound was obtained.

MP: 170° C. (decomposed)
IR(KBr)cm⁻¹: 3430, 1761, 1605
NMR(DMSO-d₆)δ: 3.60(2H,m), 4.39(2H,m), 5.03(3H,m), 5.65(1H,m), 6.70(1H,s), 6.75(3H,m), 7.20(3H,m), 7.42(1H,d,J=9Hz)

EXAMPLE 15

Preparation of disodium 7δ-[2-(2-aminothiazol-4-yl)-2-(α-carboxylatebenzyloxyimino) acetamido]-3-[5-(3,4-dihydroxyphenyl)-1,3,4-oxadiazol-2-yl]thiomethyl-3-cephem-4-carboxylate (syn-isomer)

(A) 730 mg (1 mmol) of 2-(α-benzhydryloxycarbonylbenzyloxyimino)-2-( 2-tritylaminothiazol-4-yl)acetic acid was dissolved in 10 ml of methylene chloride. To the solution 415 mg of benzhydryl 7β-amino-3-chloromethyl-3-cephem-4-carboxylate was added and cooled to 0° C. To the solution 0.57 ml (4.5 mmol) of N,N-dimethylaniline was added, and then 0.11 ml (1.2 mmol) of phosphorus oxychloride was dropwise added thereto. The mixture was stirred for 1 hour. The reaction solution was washed sequentially with 1N hydrochloric acid, a saturated sodium hydorgen carbonate aqueous solution and a saturated sodium chloride aqueous solution, and the organic layer was dried over anhydrous sodium sulfate. The solvent was distilled off under reduced pressure and ethyl ether was added to the residue to obtain 1.12 g of benzhydryl 3-chloromethyl-7β-[2-(α-benzhydryloxycarbonyl-benzyloxyimino )-2-tritylaminothiazol-4-yl)acetamido]-3-cephem-4-carboxylate (syn-isomer), which was used for the next reaction without purification.

(B) 500 mg (0.44 mmol) of the compound obtained in the above reaction (A) was dissolved in 5 ml of N,N-dimethylformamide, and 333 mg (2.22 mmol) of sodium iodide was added thereto. The mixture was stirred for 50 minutes. To the solution 172 xg (0.44 mmol) of 2-mercapto-5-[3,4-di(2-methoxyethoxymethoxy) phenyl]-1,3,4-oxadiazole was added and stirred for 2 hours. 30 ml of ethyl acetate was added to the reaction solutiom, and washed sequentially with water and a saturated sodium chloride aqueous solution and dried over anhydrous sodium sulfate. The solvent was distilled off under reduced pressure to obtain 420 mg of benzhydryl 7β-{2-[α-benzhydryloxycarbonyl-3, 4-di(2-methoxyethoxymethoxy)benzyloxyimino]-2-(2-tritylaminothiazol-4-yl) acetamido}-3-{5-[3,4-di(2methoxyethoxymethoxy) phenyl]-1,3,4-oxadiazol-2-yl}thiomethyl-3-cephem-4-carboxylate (syn-isomer), which was used for the next reaction without purification.

(C) The same operation as in EXAMPLE 1 (B) was conducted by using 400 xg (0.27 mmol) of the compound obtained in the above reaction (B), whereby 115 mg (yield: 55%) of the above identified compound.

MP: 170° C. (decomposed)
IR(KBr)cm⁻¹: 3300, 1760, 1600, 1390
NMR(D₂O)δ: 3.60(2H,br s), 4.35(2H,br s), 4.98(0.5H,d,J=4.5Hz), 5.06(0.5H,d,J=4.5Hz), 5.36(0.5H,s), 5.40(0.5H,s), 5.51(0.5H,d,J=4.5Hz), 5.72(0.5H,d,J=4.5Hz), 6.76(0.5H,s), 7.10-7.30(5H,m), 7.45-7.65(3H,m)

EXAMPLE 16

Preparation of disodium 7δ-[2-(2-aminothiazol-4-yl)-carboxylate-3, 4-dihvdroxybenzyloxyimino)acetamido]-3-[5-(3, 4-dihydroxyphenyl)-1,3,4-oxadiazol-2-yl]thiomethyl-3-cephem.-4-carboxylate (syn-isomer)

The same operation as in EXAMPLE 15 was conducted by using 4.87 g (5.19 mmol) of 2-[α-benzhydryloxycarbonyl-3, 4-di(2-methoxyethoxymethoxy)-benzyloxyimino]-2-(2-tritylaminothiazol-4-yl) acetic acid (syn-isomer) and 2.34 g (5.64 mmol) of benzhydryl 7δ-amino-3-chloromethyl-3-cephem-4-carboxylate, whereby 184 mg of the above identified compound was obtained.

MP: 170° C.
IR(KBr)cm⁻¹: 3420, 1762, 1600
NMR(DMSO-d₆)δ: 3.60(2H,m), 4.40(2H,m), 4.95(0.5H,d,J=5.0Hz), 5.06(0.5H,d,J=5.0Hz), 5.15(0.5H,s), 5.21(0.5H,s), 5.51(0.5H,d,J=5.0Hz), 5.57(0.5H,d,J=5.0Hz), 6.50-7.00(5H,m), 7.25(2H,m)

EXAMPLE 17

Preparation of 7β-[2-(2-aminothiazol-4-yl)-2-(4hydroxybenzyloxyimino) acetamido]-3-[5-(3,4-dihydroxyphenyl)-1,3, 4-oxadiazol-2-yl]thiomethyl-3-cephem-4carboxylic acid (syn-isomer)

The same operation as in EXAMPLE 1 was conducted by using 2.04 g (2 mmol) of benzhydryl 3-chloromethyl-7β-{2-[4-(2-methoxyethoxymethoxy)-benzyloxyimino]-2-(2-tritylaminothiazol-4-yl) acetamido}-3-cephem-4-carboxylate (syn-isomer) and 773 mg (2 mmol) of 2-mercapto-5-[3,4-di(2-methoxyethoxymethoxy) phenyl]-1,3,4-oxadiazole, whereby 530 g (yield: 38.0%) of the above identified compound was obtained.

MP: 170° C.
IR(KBr)cm⁻¹: 1770, 1620, 1520, 1385, 1360, 1285, 1250, 1180
NMR(DMSO-d₆)δ: 3.70(2H,br s), 4.25(1H,d,J=14Hz), 4.45(1H,d,J=14Hz), 5.00(2H,s), 5.13(1H,d,J=5Hz), 5.77(1H,dd,J=5 and 8Hz), 6.70(1H,s), 6.72(2H,d,J=8Hz), 6.88(1H,d,J=8Hz), 7.28(1H,d,J=8Hz), 7.38(2H,d,J=8Hz), 7.40(1H,s), 9.60(1H,d,J=8Hz)

EXAMPLE 18

Preparation of disodium 7δ-[2-(2-aminothiazol-4-yl)-2-( 3-carboxylate-4-hydroxybenzyloxyimino)acetamido]-3-[5-(3, 4-dihydroxyphenyl)-1,3,4-oxadiazol-2-yl]-thiomethyl-3-cephem-4-carboxylate (syn-isomer)

The same operation as in EXAMPLE 1 was conducted by using 1.23 g (1 mmol) of 7β-(2-[3-benzhydryloxycarbonyl-4-(2-methoxyethoxymethoxy) benzyloxyimino]-2-(2-tritylaminothiazol-4-yl) acetamido)-3-chloromethyl-3-cephem-4-carboxylate (syn-isomer) and 386 mg (1 mmol) of 2-mercapto-5-[3,4-di(2-methoxyethoxymethoxy)phenyl]-1,3, 4-oxadiazole, whereby 230 mg (yield: 29.3%) of the above identified compound was obtained.

MP: 180° C. (decomposed)
IR(KBr)cm⁻¹: 1770, 1620, 1540, 1380, 1360, 1290
NMR(DMSO-d₆)δ: 3.40(1H,d,J=18Hz), 3.68(1H,d,J=18Hz), 4.40(2H,br s), 4.98(2H,s), 5.00(1H,d,J=5Hz), 5.60(1H,d,J=5Hz),
6.60(1H,d,J=8Hz), 6.83(1H,d,J=8Hz),
7.20(1H,d,J=8Hz), 7.22(1H,d,J=8Hz), 7.30(1H,s),
7.70(1H,s)

EXAMPLE 19

Preparation of disodium 7β-[2-(2-aminothiazol-4-yl)-2-(4-carboxylatebenzyloxyimino) acetamido]-3-[5-(3,4-dihydroxyphenyl)-1,3,4-oxadiazol-2-yl]thiomethyl-3-cephem-4-carboxylate (syn-isomer)

The same operation as in EXAMPLE 1 was conducted by using 550 mg (0.46mmol) of benzhydryl 7β-[2-(4-benzhydryloxycarbonylbenzyloxyimino)-2-( 2-tritylaminothiazol-4-yl)-acetamido]-3-iodomethyl-3-cephem-4-carboxylate (syn-isomer) and 176 mg (0.46 mmol) of 2-mercapto-5-[3,4-di(2-methoxyethoxymethoxy) phenyl]-1,3,4-oxadiazole, whereby 54 mg (yield: 16%) of the above identified compound.
MP: 165° C. (decomposed)
IR(KBr)cm$^{-1}$: 1765, 1600, 1540, 1390
NMR(DMSO-d$_6$)δ: 3.35(1H,d,J=18Hz), 3.63(1H,d,J=18Hz), 4.30(2H,br s), 4.98(1H,d,J=5Hz), 5.12(2H,s), 5.60(1H,d,J=5Hz), 6.70(1H,s), 6.77(1H,d,J=8Hz), 7.20(1H,d,J=8Hz), 7.25(1H,s), 7.27(2H,d,J=8Hz), 7.80(2H,d,J=8Hz)

EXAMPLE 20

Preparation of disodium 7δ-[2-(2-aminothiazol-4-yl)-2-( 3-carboxylatebenzyloxyimino)acetamido]-3-[5-(3, 4-dihydroxyphenyl)-1,3,4-oxadiazol-2-yl ]-thiomethyl-5-cephem-4-carboxylate (syn-isomer)

(A) a) 465 mg (1.1 mmol) of 7β-amino-3-[5-(3,4-dihydroxyphenyl)-1,3, 4-oxadiazol-2-yl]thiomethyl-3-cephem-4-carboxylic-acid was suspended in 5 ml of methylene chloride, and 1.08 ml (4.4 mmol) of N,O-bis(trimethylsilyl)acetamide was added thereto. The mixture was dissolved by refluxing for 1 hour, and cooled to −15° C. To the solution 0.95 ml (7.5 mmol) of N,N-dimethylaniline was added and kept at the same temperature.
b) 10 ml of a methylene chloride solution containing 229 mg (1.1 mmol) of phosphorus pentachloride was cooled to −10° C., and 730 mg (1 mmol) of 2-(3-benzhydryloxy-carbonylbenzyloxyimino )-2-(2-tritylaminothiazol-4-yl)acetic acid (syn-isomer) was added thereto. The mixture was stirred at −5° C. for 30 minutes. This methylene chloride solution was dropwise added to the solution prepared in the above reaction a), and stirred at a temperature of from −10° to 0° C. for 3 hours. The reaction solution was concentrated under reduced pressure, and ethyl acetate and water were added to the residue. Insoluble substances were filtered off, and then the filtrate was subjected to liquid separation. The etheyl acetate layer was washed sequentially with water and a saturated sodium chloride aqueous solution, dehydrated over anhydrous sodium sulfate, and then concentrated. The residue was separated and purified by silica gel flash cloumn chromatography (Wakogel C-300, elution with a 20% acetone methylene chloride) to obtain 870 mg (yield: 76.7%) of 78-[2-(3-benzhydryloxycarbonylbenzyloxyimino)-2-( 2-tritylaminothiazol-4-yl)acetamido]-3-[5-(3, 4-dihydroxyphenyl)-1,3,4-oxadiazol-2-yl]thiomethyl-3-cephem-4-carboxylic acid (syn-isomer) as a foamy substance.

(B) To 870 mg of the compound obtained in the above reaction (A), 8 ml of methylene chloride and 0.8 ml of anisole were added and cooled with ice. 8 ml of trifluoroacetic acid which was preliminary cooled with ice was added thereto, and the mixture was stirred at room temperature for 2 hours. 80 ml of ethyl ether was added to the reaction soluiton, and the precipitates were collected by filtration. The precipitates were suspended in 100 ml of water and adjusted to pH7.2 with a saturated sodium hydrogencarbonate aqueous solution. The suspension was subjected to reversed phase chromatography (LC Sorb RP-18, 100 ml) after washing with water 400 ml, eluting with 5–10% methanol aqueous solution, and the fraction containing the desired compound was freeze-dried to obtain 250 mg (yield: 42.3%) of the above identified compound.
MP: 170° C. (decomposed)
IR(KBr)cm$^{-1}$: 1770, 1660, 1610, 1560, 1480, 1390, 1360, 1280
NMR(DMSO-d$_6$)δ: 3.45(1H,d,J=18Hz), 3.72(1H,d,J=18Hz), 4,35(2H,br s), 5.00(1H,d,J=5Hz), 5.15(2H,s), 5.64(1H,d,J=5Hz), 6.58(1H,d,J=8Hz), 6.72(1H,s), 7.10-7.40(4H,m), 7.70-7.90(2H,m)

EXAMPLE 21

Preparation of disodium 7β-[2-(2-(aminothiazol-4-yl)-2-(4-carboxylatemethylbenzyloxyimino) acetamido]-3-[5-(3,4-dihydroxyphenyl)-1,3,4-oxadiazol-2-yl]thiomethyl-3-cephem-4-carboxylate (syn-isomer)

The same operation as in EXAMPLE 20 was conducted by using 372 mg (0.5 mmol) of 2-(4-benzhydryloxycarbonyl-methylbenzyloxyimino )-2-(2-tirtylaminothiazol-4-yl)acetic acid (syn-isomer) and 211 mg (0.5 mmol) of 7β-amino-3-[5(3,4-dihydroxyphenyl-1, 3,4-oxadiazol-2-yl]thiomethyl-3-cephem-4-carboxylic acid, whereby 67 mg (yield: 17.1%) of the above identified compound was obtained.
MP: 170° C. (decomposed)
IR(KBr)cm$^{-1}$: 1770, 1620, 1540, 1480, 1390, 1360, 1290
NMR(DMSO-d$_6$)δ: 3.26(2H,s), 3.40(1H,d,J=18Hz), 3.70(1H,d,J=18Hz), 4.35(2H,br s), 5.00(1H,d,J=5Hz), 5.06(2H,s), 5.60(1H,d,J=5Hz), 6.68(1H,s), 6.72(1H,d,J=8Hz), 7.00-7.30(6H,m)

EXAMPLE 22

Preparation of sodium 7β-[2-(2-aminothiazol-4-yl)2phenoxyiminoacetamido]-3-[5-(3, 4-dihydroxyphenyl)-1,3,4-oxadiazol-2-yl]thiomethyl-3-cephem-4-carboxylate (syn-isomer)

The same operation as in EXAMPLE 1 was conducted by using 350. mg (0.5 mmol) of benzhydryl 3-chloromethyl-7β-[2-phenoxyimino-2-(2-tritylaiminothiazol-4-yl)acetamido]-3-cephem-4-carboxylate (syn-isomer) and 105 mg (0.5 mmol) of 5-(3,4-dihydroxyphenyl)-2-mercapto-1,3,4-oxadiazole, whereby 42 mg (yield: 26.8%) of the above identified compound.
MP: 160° C. (decomposed)
IR(KBr)1cm$^{-1}$: 1765, 1640, 1520, 1380
NMR(D$_2$O/DMSO-d$_6$)δ: 3.60(2H,ABq), 4.70(2H,m), 5.20(2H,d,J=4.5Hz), 5.76(1H,d,J=4.5Hz), 7.08(1H,s), 7.20–7.40(8H,m)

EXAMPLE 23

Preparation of disodium
7β-(2-(2-aminothiazol-4-yl)-2-[2-(carboxylatemethyl)-benzyloxyimino]acetamido}-3-[5-3, 4,-dihydroxyphenyl)-1,3,4-oxadiazol-2-yl]thiomethyl-3-cephem-4-carboxylate (syn-isomer)

The same operation as in EXAMPLE 20 was conducted by using 744 mg (1.0 mmol) of 2-[2-(benzhydryloxycarbonylmethyl) benzyloxyimino]-2-(2-tritylaminothiazol-4-yl)acetic acid (syn-isomer) and 422 mg (1.0 mmol) of 7β-amino-3 [5-(3, 4-di-hydroxyphenyl)-1,3,4-oxadiazol-2-yl]thiomethyl-3-cephem-4-carboxylic acid, whereby 234 mg (yield: 30%) of the above identified compound was obtained.

MP: 170° C. (decomposed)
IR(KBr)cm$^{-1}$: 1770, 1660, 1600, 1540, 1480, 1380, 1280
NMR(DMSO-d$_6$)δ: 3.40(2H,s), 3.50(2H,br s), 4.30(2H,br s), 5.00(1H,d,J=5Hz), 5.27(2H,s), 5.60(1H,d,J=5Hz), 6.70(1H,s), 6 73(1H,d,J=8Hz), 7.00-7.30(5H,m)

EXAMPLE 24

Preparation of disodium
78-[2-(2-aminothiazol-4-yl)-2-(α-carboxylatebenzyloxyimino) acetamido]-3-[5-(3,4-dihydroxyphenyl)-1,3,4-oxadiazol-2-yl]-thiomethyl-3-cephem-4-carboxylate (diastereomer A and B, synisomer)

The same operation as in EXAMPLE 20 was conducted by using 9.8 g (23.2 mmol) of 7β-amino-3-[5-(3,4-dihydroxyphenyl)-1,3, 4-oxadiazol-2-yl]thiomethyl-3-cephem-4carboxylic acid obtained in REFERENCE EXAMPLE 21 given hereinafter and 18.6 g (25.5 mmol) of 2-(α-benzhydryloxycarbonylbenzyloxyimino)-2-( 2-tritylaminothiazol-4-yl)acetic acid (syn-isomer). By ODS column chromatography, diastereomer A was eluted with a 5% methanol aqueous solution and diastereomer B was eluted with a 10% methanol aqueous solution. The fraction containing the respective desired compounds was concentrated and freeze-dried to obtain 620 g (yield: 3.5%) of diastereomer A and 400 mg (yield: 2.2 %) of diastereomer B.

High-performance liquid chromatography analysis
Column: ODS (YMC-PACK A-302) 4.6×150 mm
Mobile phase: 45% MeOH-0.01M Phosphate buffer (PH 3.0)
Flow rate: 1.2 ml/min
Detection: UV 280 nm
Diastereomer A: 5.9 minutes
Diastereomer B: 8.3 minutes
Diastereomer A
MP: 195° C. (decomposed)
IR(KBr)cm$^{-1}$: 1770, 1615, 1535, 1395
NMR(D$_2$O/DSS)δ: 3.40(2H,ABq), 4.08(2H,ABq), 5.07(1H,d,J=4.5Hz), 5.55(1H,s), 5.68(1H,d,J=4.5Hz), 6.95(1H,s), 7.10-7.60(8H,m)
Diastereomer B
MP: 180° C. (decomposed)
IR(KBr)cm$^{-1}$: 1765, 1610, 1535, 1400
NMR(D$_2$O/DSS)δ: 3.30(2H,ABq), 4.15(2H,br s), 5.00(1H,d,J=4.5Hz), 5.54(1H,s), 5.63(1H,d,J=4.5Hz), 6.90(1H,s), 7.10-7.60(8H,m)

EXAMPLE 25

Preparation of sodium 7β-[2-(2-aminothiazol-4-yl)-2-methoxviminoacetamido]-3-[5-(3, 4-dihydroxyphenyl)-1,3,4-thiadiazol-2-yl]thiomethyl-3-cephem-4-carboxylate (syn-isomer)

A trifluoroacetate obtained by the same operation as in EXAMPLE 1 by using 1.0 g (1.07 mmol) of benzhydryl 3-iodomethyl-7β-[2-methoxyimino-2-(2-tritylaminothiazol-4-yl) acetamido]-3-cephem-4-carboxylate (syn-isomer) and 0.43 g (1.07 mmol) of 2-mercapto-5-[3,4-di(2-methoxyethoxymethoxy)phenyl]-1,3,4-thiadiazole, was suspended in water and adjusted to pH6.5 with a saturated sodium hydrogencarbonate aqueous solution. Then, the suspension was subjected to ODS column chromatography (LC Sorb RP-18, manufactured by Kemco Co.) and eluted with a 20% methanol aqueous solution. The fraction containing the desired compound was concentrated and freeze-dried to obtain 168 mg (yield: 24.3%) of the above identified compound.

MP: 195° C. (decomposed)
IR(KBr)cm$^{-1}$: 3400, 1765, 1600, 1535
NMR(DMSO-d$_6$)δ: 3.55(2H,m), 3.87(3H,s), 4.50(2H,m), 5.03(1H,d,J=5Hz), 5.60(1H,m), 6.75(2H,m), 7.08(1H,m), 7.23(1H,br s)

EXAMPLE 26

Preparation of sodium 7β-[2-(2-aminothiazol-4-yl)-2-methoxyiminoacetamido]-3[5-(3,4-diacetoxyphenyl)-1,3, 4-thiadiazol-2-yl]thiomethyl-3-cechem-4-carboxylate (syn-isomer)

(A) 1.0 g (1.09 mmol) of benzhydryl 3-iodomethyl-7β-[2-metoxyimino-2-( 2-tritylaminothiazol-4-yl)acetamido]-3-cephem-4-carboxylate (syn-isomer) was dissolved in 10.0 ml of N,N-dimethylformamide, and 0.30 g (1.33 mmol) of 5-(3,4-dihydroxyphenyl)-2-mercapto-1,3,4-thiadiazole was added thereto. The mixture was stirred at room temperature for 2 hours. To the reaction solution 1.0 ml of acetic anhydride and 0.8 ml of pyridine were added and stirred at room temperature for 1 hour. The solvent was distilled. off under reduced pressure, and the residue was purified by silica gel cloumn chromatography (Wakogel C-300 ethyl acetate:hexane =3:1) to obtain 0.73 g (yield: 60%) of benzhydryl 3-[5-(3,4-diacetoxyphenyl)-1,3, 4-thiadiazol-2-yl]thiomethyl-7β-[2-methoxyimino-2-(2-tritylaminothiazol-4-yl) acetamido]-3-cephem-4-carboxylate as a foamy substance.

NMR(DMSO-d$_6$)δ: 2.32(6H,s), 3.80(2H,m), 3.82(3H,s), 4.10-4.70(2H,m), 5.20(1H,d,J=5Hz), 5,72(1H,m), 6.72(1H,s), 6.90(1H,s), 7.00-7.60(26H,m), 7.76(1H,m), 7.80(1H,s), 8.75(1H,m), 9.55(1H,m)

(B) 724 mg (0.66 mmol) of the compound obtained in the above reaction (A) was dissolved in 3.5 ml of methylene chloride and 0.7 ml of anisole, and 3.5 ml of trifluoroacetic acid was added under cooling with ice. The mixture was stirred for 1 hour. The solvent was distilled off under reduced pressure, and ethyl ether was added to the residue. The precipitates were collected by filtration and suspended in water. After adjusted pH6.5 with a saturated sodium hydrogencarbonate, the suspension was subjected to ODS column chromatography (LC Sorb RP-18,-manufactured by Kemco Co.) and eluted with a 40% methanol aqueous solution. The fraction containing the desired compound was concentrated and freeze-dried to obtain 191 mg (yield: 40%) of the above identified compound.

MP: 180° C. (decomposed)
IR(KBr)cm$^{-1}$: 3430, 1770, 1680, 1615

NMR(DMSO-d$_6$)δ: 2.35(6H,s), 3.60(2H,m), 3.90(3H,s), 4.40–4.80(2H,m), 5.08(1H,d,J=5Hz), 5.66(1H,dd,J=5 and 8Hz), 6.76(1H,s), 7.46(1H,d,J=9Hz), 7.82(1H,m), 7.88(1H,br s), 9.54(1H,d,J=8Hz)

EXAMPLE 27

Preparation of sodium 7β-[2-(2-aminothiazol-4-yl)-2-ethoxyiminoacetamido]-3-[5-(3, 4-dihydroxyphenyl-1,3,4-thiadiazol-2-yl-thiomethyl-3-cephem-4-carboxylate (syn-isomer)

A trifluoroacetate obtained by the same operation as in EXAMPLE 1 by using 800 mg (0.86 mmol) of benzhydryl 3-iodomethyl-7β-[2-ethoxyimino-2-(2-tritylaminothiazol-4-yl) acetamido]-3-cephem-4-carboxylate (syn-isomer) and 0.50 g (1.24 mmol) of 5-[3,4-di(2-methoxyethoxymethoxy)phenyl]-2-mercapto-1,3,4-thiadiazole, was suspended in water and adjusted to pH6.5 with a saturated sodium hydrogencarbonate aqueous solution. The suspension was subjected to ODS column chromatography (LC Sorb RP-18, manufactured by Kemco Co.) and eluted with a 30% methanol aqueous solution. The fraction containing the desired compound was concentrated and freeze-dried to obtain 61 mg (yield: 10.8%) of the above identified compound.

MP: 195° C. (decomposed)

IR(KBr)cm$^{-1}$: 3420, 1760, 1660, 1610

NMR(DMSO-d$_6$)δ: 1.23(3H,q,J=6Hz), 3.55(2H,m), 4.13(2H,q,J=6Hz), 4.46(2H,m), 5.05(1H,d,J=5Hz), 5.62(1H,m), 6.70(1H,m), 6.72(1H,s), 7.08(1H,m), 7.20(1H,br s)

EXAMPLE 28

Preparation of sodium 7β-[2-(2-aminothiazol-4-yl)2-ethoxyiminoacetamido]-3-[5-(3, 4-diacetoxyphenyl)-1,3,4-thiadiazol-2-yl]thiomethyl-3-cephem-4-carboxylate (syn-isomer)

The trifluoroacetate obtained by the same operation as in EXAMPLE 26 by using 800 mg (0.86 mmol) of benzhydryl 3-iodomethyl-7β-[2-ethoxyimino-2-(2-tritylaminothiazol-4-yl) acetamido]-3-cephem-4-carboxylate (syn-isomer) and 300 mg (1.33 mmol) of 2-mercapto-5-(3,4-dihydroxyphenyl)-1,3, 4-thiadiazole, was suspended in water and adjusted to pH6.5 with a saturated sodium hydrogencarbonate. The suspension was subjected to ODS column chromatography (LC Sorb RP-18, manufactured by Kemco Co.) and eluted with a 40% methanol aqueous solution. The fraction containing the desired compound was concentrated and freeze-dried to obtain 106 mg (yield: 16.6%) of the above identified compound.

MP: 180° C. (decomposed)

IR(KBr)cm$^{-1}$: 3430, 1775, 1675, 1620, 1540

NMR(DMSO-d$_6$)δ: 1.22(3H,t,J=6Hz), 2.32(6H,s), 3.50(2H,m), 4.12(2H,q,J=6Hz), 4.20–4.70(2H,m), 5.06(1H,d,J=5Hz), 5.65(1H,m), 6.72(1H,s), 7.46(1H,d,J=5Hz), 7.82(1H,m), 7.87(1H,br s), 9.48(1H,m)

EXAMPLE 29

Preparation of sodium 7β-[2-(2-aminothiazol-4-yl)-2-isopropoxyiminoacetamido]-3-[5-(3,4-dihydroxyphenyl)-1,3,4-thiadiazol-2-yl]thiomethyl-3-cephem-4-carboxylate (syn-isomer)

A trifluoroacetate obtained by the same operation as in EXAMPLE 1 by using 800 mg (0.83 mmol) of benzhydryl 3-iodomethyl-7β-[2-isopropoxyimino-2-(2-tritylamino-thizaol-4-yl) acetamido]-3-cephem-4-carboxylate (synisomer) and 200 mg (1.07 mmol) of 5-(3,4-dihydroxy-phenyl)-2-mercapto-1,3,4-thiadiazole, was suspended in water and adjusted to pH6.5 with a saturated sodium hydrogencarbonate. The suspension was subjected to ODS column chromatography (LC Sorb RP-18, manufactured by Kemco Co.) and eluted with a 20% methanol aqueous solution. The fraction containing the desired product was concentrated and freeze-dried to obtain 39 mg (yield: 6.75%) of the above identified compound.

MP: 185° C. (decomposed)

IR(KBr)cm$^{-1}$: 3400, 1760, 1600, 1530

NMR(DMSO-d$_6$)δ: 1.20(6H,t,J=6Hz), 3.52(2H,m), 4.10–4.70(3H,m), 5.08(1H,d,J=5Hz), 5.60(1H,m), 6.70(1H,s), 6.75–7.26(2H,m), 7.32(1H,br s)

EXAMPLE 30

Preparation of sodium 78-[2-allyloxyimino-2-(2-aminothiazol-4-yl) acetamido]-3-[5-(3,4-dihydroxyphenyl)-1, 3,4-thiadiazol-2-yl]thiomethyl-3-cephem-4-carboxylate (syn-isomer)

The same operation as in EXAMPLE 1 was conducted by using 800 mg (0.83 mmol) of benzhydryl 7β-[2-allyloxy-imino-2-( 2-tritylaminothiazol-4-yl)acetamido]-3-iodomethyl-3-cephem-4-carboxylate and 340 mg (0.83 mmol) of 2-mercapto-5-[3,4-di(2-methoxyethoxymethoxy)phenyl]-1,3,4thiadiazole, whereby 120 mg (yield: 21.6%) of the above identified compound was obtained.

MP: 190° C. (decomposed)

IR(KBr)cm$^{-1}$: 3430, 1760, 1660, 1600, 1530

NMR(DMSO-d$_6$)δ: 3.55(2H,m), 4.30-4.70(2H,m), 5.10(1H,d,J=5Hz), 5.25(1H,br s), 5.43(1H,br s), 5.64(1H,d,J=5Hz), 5.80–6.20(1H,m), 6.60–7.20(2H,m), 6.74(1H,s), 7.26(1H,br s)

EXAMPLE 31

Preparation of sodium 7β-[2-(2-aminothiazol-4-yl)-2-proparqyloxyiminoacetamido ]-3-[5-(3,4-dihvdroxyphenyl)-1,3, 4-thiadiazol-2-yl ]thiomethyl-3-cephem-4-carboxylate (syn-isomer)

The same operation as in EXAMPLE 1 was conducted by using 800 mg (0.84 mmol) of benzhydryl 3-iodomethyl-7β-[2-propargyloxyimino-2-(2-tritylaminothiazol-4-yl)acetamido]-3-cephem-4-carboxylate (syn-isomer) and 200 mg (0.88 mmol) of 5-(3,4-dihydroxyphenyl)-2-mercapto-1,3,4-thiadiazole, whereby 114 mg (yield: 20.2%) of the above identified: compound was obtained.

MP: 165° C. (decomposed)

IR(KBr)cm$^{-1}$: 3430, 1760, 1600

NMR(DMSO-d$_6$)δ: 3.43(1H,br s), 3.60(2H,m), 4.50(2H,m), 4.75(2H,br s), 5.06(1H,d,J=5Hz), 5.60(1H,d,J=5Hz), 6.60–7.20(1H,m), 6.78(1H,s), 7.22(1H,br s)

EXAMPLE 32

Preparation of 7β-[2-(2-aminothiazol-4-yl)-2-benzyloxviminoacetamido]-3-[5-(3, 4-dihydroxvphenvl)-1,3,4-thiadiazol-2-yl]thiomethyl-3-cephem-4-carboxylic acid trifluoroacetate (syn-isomer)

(A) The same operation as in EXAMPLE 1 was conducted by using 800 mg (0.79 mmol) of 7β-[2-benzyloxyimino-2-(2-tritylaminothiazol-4yl) acetamido]3-iodomethyl-3-cephem-4-carboxylate (syn-isomer) and 318 mg (0.79 mmol) of 2-mercapto-5-[3,4-di(2-methoxyethoxymethoxy)phenyl]-1,3, 4-thiadiazole, whereby 278 mg (yield: 27%) of benzhydryl 7β-[2-benzyloxyimino-2-(2-tritylaminothizaol-4-yl)-acetamido]-3-{5-[3,4-di(2-methoxyethoxymethoxy)phenyl]-1,3, 4-thiadiazol-2-yl}thiomethyl-3-cephem-4carboxylate (syn-isomer) was obtained as a foamy substance;

NMR(DMSO-d$_6$)δ: 3.23(6H,s), 3.50(4H,m), 3.78(6H,m), 4.10–4.60(2H,m), 5.21(1H,d,J=5Hz), 5.22(2H,br s), 5.32(4H,br s), 5.82(1H,m), 6.74(1H,s), 6.91(1H,s), 7.00-7.60(33H,m), 8.77(1H,br s), 9.65(1H,br d,J=8Hz)

(B) 278 mg (0.22 mmol) of the compound obtained in the above reaction (A) was dissolved 1.5 ml of methylene chloride and 0.3 ml of anisole, and 1.5 ml of trifluoroacetic acid was added thereto under cooling with ice. The solvent was distilled off under reduced pressure, and ethyl ether was added to the residue. The precipitate was collected by filtration to obtain 148 mg (yield: 98%) of the above identified compound.

MP: 170° C. (decomposed)
IR(KBr)cm$^{-1}$: 3380, 1775, 1675, 1530
NMR(DMSO-d$_6$)δ: 3.72(2H,m), 4.26(2H,br d,J=12Hz), 4.68(1H,d,J=12Hz), 5.16(1H,d,J=5Hz), 5.22(2H,br s), 5.74(1H,m), 6.80-7.50(9H,m), 9.72(1H,m)

EXAMPLE 33

Preparation of 7β-[2-(2-aminothiazol-4-yl)-2-(3,4-dihydroxvbenzyloxyimino) acetamido]-3-[5-(3,5-dihydroxyphenyl)-1,3, 4-thiadiazol-2-yl]thiomethvl-3-cephem-4-carboxylic acid trifluoroacetate The same operation as in EXAMPLE 32 was conducted by using 800 mg (0.65 mmol) of benzhydryl 3-iodomethyl-7β-({2-[3,4-di(2-methoxyethoxymethoxy)benzyloxyimino]-2-(2-tritylaminothiazol-4-yl) acetamido}-3-cephem-4-carboxylate (syn-isomer) and 148 mg (0.35 mmol) of 5-(3,4-dihydroxyphenyl)-2-mercapto-1,3, 4-thiadiazol, whereby 214 mg (yield: 96%) of the above identified compound (synisomer) as obtained.

MP: 165° C. (decomposed)
IR(KBr)cm$^{-1}$: 3400, 1770, 1675, 1525
NMR(DMSO-d$_6$)δ: 3.75(2H,m), 4.28(1H,br d,J=12Hz), 4.60(1H,br d,J=12Hz), 5.00(2H,br s), 5.18(1H,d,J=5Hz), 5.80(1H,m), 6.60-7.40(7H,m), 9.70(1H,m)

EXAMPLE 34

Preparation of disodium 7β-[2-(2-aminothiazol-4-yl-2-(1-carboxylate-1-methylethoxyimino) acetamido]-3-[5-(3,4-dihvdroxyphenyl)-1,3, 4-thiadiazol-2-vl]thiomethyl-3-cephem-4-carboxylate (syn-isomer)

A fluoroacetate obtained by the same operation as in EXAMPLE 1 by using 1.0 g (0.85 mmol) of benzhydryl 7β-[2-(1-benzhydryloxycarbonyl-1-methylethoxyimino)-2-(2-tritylaminothiazol-4-yl) acetamido]-3-iodomethyl-3-cephem-4-carboxylate (syn-isomer) and 0.34 mg (0.84 mmol) of 2-mercapto-5-[3,4-di(2-methoxyethoxymethoxy)phenyl]-1,3, 4-thiadiazole, was suspended in water and adjusted to pH6.5 with a saturated sodium hydrogencarbonate aqueous solution. The suspension was subjected to ODS column chromatograpy (LC Sorb RP-18, manufactured by Kemco Co.) and eluted with a 10% methanol aqueous solution. The fraction containing the desired compound was concentrated and freeze-dried to obtain 148 mg (yield: 41.1%) of the above identified compound.

MP: 185° C. (decomposed)
IR(KBr)cm$^{-1}$: 3430, 1760, 1590
NMR(DMSO-d$_6$)δ: 1.44(3H,br s), 1.50(3H,br s), 3.53(2H,m), 4.42(2H,m), 5.06(1H,d,J=5Hz), 5.70(1H,m), 6.72(1H,m), 6.75(1H,s), 7.15(1H,m), 7.20(1H,br s)

EXAMPLE 35

Preparation of disodium 7β-[2-(2-aminothiazol-4-yl)-2-(1-carboxylate-1-cyclooropoxyimino)acetamido]-3-[5-(3, 4-dihydroxyphenyl)-1,3,4-thiadiazol-2-yl]thiomethyl-3-cephem-4-carboxylate (syn-isomer)

The same operation as in EXAMPLE 1 was conducted by using 1.0 g (0.96 mmol) of benzhydryl 7β-[2-(1-tert-butoxycarbonyl-1-cyclopropoxyimino)-2-(2-tritylaminothiazol-4-yl)acetamido]-3-iodomethyl-3-cephem-4-carboxylate (syn-isomer) and 0.38 g (0.94 mmol) of 2-mercapto-5-[3,4-di (2-methoxyethoxymethoxy)phenyl]-1,3,4-thiadiazole, whereby 130 mg (yield: 29.4%) of the above identified compound was obtained.

MP: 170° C. (decomposed)
IR(KBr)cm$^{-1}$: 3420, 1760, 1595
NMR(DMSO-d$_6$)δ: 0.90-1.40(4H,m), 3.20-3.80(2H,m), 4.42(2H,m,), 5.05(1H,d,J=5Hz), 5.66(1H,m), 6.73(1H,d,J=9Hz), 6.85(1H,s), 7.13(1H,m), 7.23(1H,br s)

EXAMPLE 36

Preparation of disodium 7β-(2-(2-aminothiazol-4-yl)-2-[(2-carboxylatemethylbenzyl) oxyimino]acetamido}-3-[5-(3, 4-dihydroxyphenyl)-1,3,4-thiadiazol-2-yl]thiomethyl-3-cephem-4-carboxylate (syn-isomer)

The trifluoroacetate obtained by the same operation as in EXAMPE 1 by using 1.23 g (1.0 mmol) of benzhydryl 7β-{2-[(2-benzhydryloxycarbonylmethylbenzyl)oxyimino]-2-(2-tritylaminothiazol-4-yl) acetamido)-3-iodomethyl-3-cephem-4-carboxylater (syn-isomer) and 270 mg (1.2 mmol) of 5-(3,4-dihydroxyphenyl)-2-mercapto-1,3,4-thiadiazole, was suspended in water and adjusted to pH6.5 with a saturated sodium hydrogencarbonate aqueous solution. The suspension was subjected to ODS column chromatography (LC Sorb RP 18, manufactured by Kemco Co.) and eluted with a 10% methanol aqueous solution.

The fraction was concentrated and free-dried to obtain 145 mg (yield: 18%) of the above identified compound.

MP: 185° C. (decomposed)
IR(KB$_r$)cm$^{-1}$: 1770, 1590, 1530, 1380, 1280, 1190
NMR(D$_2$O)δ: 3.20(1H,d,J=15Hz), 3.60(2H,s), 3.67(1H,d,J=15Hz), 5.02(1H,d,J=5Hz), 5.30(2H,s), 5.65(1H,d,J=5Hz), 6.93(1H,s), 7.10-7.40(7H,m)

EXAMPLE 37

Preparation of disodium 7β-{2-(2-aminothiazol-4-yl)-2-[(α-carboxylatebenzyl)oxyimino]acetamido}-3-[5-(3,4-dihydroxyphenyl)-1,3,4-thiadiazol-2-yl]thiomethyl-3-cephem-4-carboxylate (diastereomer A and B, syn-isomer)

(A) The same operation as in EXAMPLE 1 was conducted by using 800 mg (0.64 mmol) of benzhydryl 7β-{2-[(α-benzhydryloxycarbonylbenzyl)oxyimino]-2-(2-tritylaminothiazol4-yl)acetamido]}-3-iodomethyl-3-cephem-4-carboxylate (syn-isomer) and 0.32 g (0.80 mmol) of 2-mercapto-5-[3,4di (2-methoxyethoxymethoxy)phenyl]-1,3,4-thiadiazole, whereby benzhydryl 7β-(2-[(α-benzhydryloxycarbonyl benzyl)oxyimino]-2-(2-tritylaminothiazol-4-yl)acetamido}-3-{5-[3,4-di (2-methoxyethoxymethoxy)phenyl]-1,3,4-thiadiazol-2-yl}thiomethyl-3-cephem-4-carboxylate (synisomer) was obtained as a crude product.

NMR(DMSO-d$_6$)δ: 3,25(6H,s), 3.50(4H,m), 3.80(6H,m), 4.10-4.80(2H,m), 5.00-6.00(7H,m), 6.80-7.70(36H,m)

(B) The crude product obtained in the above reaction (A) was dissolved in 5.0 ml of methylene chloride and 1.0 ml of anisole under cooling with ice, and 5.0 ml of trifluoroacetic acid was added thereto. The mixture was stirred for 1 hour. The solvent was distilled off under reduced pressure, and ethyl ether was added to the residue. The precipitates were collected by filtration and suspended in water. After adjusted to pH6.5 with a saturated sodium- hydrogencarbonate, the suspension was subjected to ODS column chromatography (LC Sorb RP-18, manufactured by Kemco Co.). Diastereomer A was eluted with a 5% methanol aqueous solution and diastereomer B was eluted with a 10% methanol aqueous solution. The fractions containing the desired compounds were concentrated and freeze-dried to obtain 100 mg (yield: of diastereomer A and 98 mg (yield: 19%) of diastereomer B.

High-performance liquid chromatography analysis
Column: ODS (YMC-PACK AM-312) 6×150 mm
Mobile phase: 60% MeOH-0.01M Phosphate buffer (PH 3.0)
Flow rate: 1 ml/min
Detection: UV 254 nm
 Diastereomer A: 3.3 minutes
 Diastereomer B: 3.6 minutes
Diastereomer A
MP: 190° C. (decomposed)
IR(KBr)cm$^{-1}$: 3420, 1760, 1600, 1530
NMR(DMSO-d$_6$)δ: 3.52(2H,m), 4.10-4.80(2H,m), 5.06(1H,d,J=5Hz), 5.36(1H,s), 5.42(1H,m), 6.50(1H,m), 6.82(1H,s), 6.90-7.70(7H,m)
Diastereomer B
MP: 190° C. (decomposed)
IR(KBr)cm$^{-1}$: 3400, 1760, 1600, 1530
NMR(DMSO-d$_6$)δ: 3.40(2H,m), 4.10-4.70(2H,m), 4.98(1H,d,J=5Hz), 5.42(1H,s), 5.45(1H,m), 6.70(1H,m), 6.90(1H,s), 7.00-7.70(7H,m)

EXAMPLE 38

Preparation of disodium 7β-{2-(2-aminothiazol-4-yl)-2-(α-carboxylate-3,4-dihydroxybenzyloxyimino)acetamido]-3-[5-(3,4-dihydroxyphenyl)-1,3,4-thiadiazol-2-yl]thiomethyl-3-cephem-4-carboxylate (diastereomer A and diastereomer B, syn-isomer)

A suspension obtained by the same operation as in EXAMPLE 37 by using 800 mg (0.56 mmol) of benzhydryl 7β-{(2-[α-benzhydryloxycarbonyl-3,4-di(2-methoxyethoxymethoxy)benzyloxyimino]-2-(2-tritylaminothiazol-4-yl)-acetamido}-3-iodomethyl-3-cephem-4-carboxylate (synisomer) and 224 mg (0.56 mmol) of 2-mercapto-5-[3,4-di (2-methoxyethoxymethoxy)phenyl]-1,3,4-thiadiazole, was subjected to ODS column chromatograpy (LC Sorb RP-18, manufactured by Kemco Co.) and eluted with a 5% methanol aqueous solution. The fraction was concentrated and freeze-dried to obtain 46 mg (yield: 10.1%) of diastereomer A and 40 mg (yield: 8.8%) of diastereomer B.

High-performance liquid chromatography analysis
Column ODS (YMC-PACK AM-312) 6 x 150 mm
Mobile phase: 40% MeOH-0.01M Phosphate buffer (PH 3.0)
Flow rate: 1 ml/min
Detection: UV 254 nm
 Diastereomer A: 8.2 minutes
 Diastereomer B: 10.2 minutes
Diastereomer A
MP: 175° C. (decomposed)
IR(KBr)cm$^{-1}$: 3430, 1765, 1600, 1540
NMR(DMSO-d$_6$)δ: 3.55(2H,m), 4.50(2H,m), 5.15(2H,m), 5.70(1H,m), 6.50-7.30(7H,m)
Diastereomer B
MP: 180° C. (decomposed)
IR(KBr)cm$^{-1}$: 3420, 1765, 1600, 1540
NMR(DMSO-d$_6$)δ: 3.50(2H,m), 4.40(2H,m), 5.00(1H,m), 5.22(1H,m), 5.50(1H,m), 6.60-7.30(7H,m),

EXAMPLE 39

Preparation of sodium 7β-[2-(2-aminothiazol-4-yl)-2-methoxviminoacetamido]-3-[4-(3,4-dihydroxyphenvl)-thiazol-2-yl]thiomethyl-3-cephem-4-carboxylate (syn-isomer)

A fluoroacetate obtained by the same operation as in EXAMPLE 1 by using 1.0 g (1.1 mmol) of benzhydryl 3-iodomethyl-7β-[2-methoxyimino-2-(2-tritylaiminothiazol-4-yl) acetamido]-3-cephem-4-carboxylate (synisomer) and 0.23 g (1.1 mmol) of 4-(3,4-dihydroxyphenyl)-2-mercaptothiazole, was suspended in water and adjusted to pH6.5 with a saturated sodium hydrogencarbonate aqueous solution. Insoluble substances were filtered off. The filtrate was subjected to ODS reversed phase column chromatography (LC Sorb RP-18, manufactured by Kemco Co.). The fraction (30% methanol aqueous solution) containing the desired product was concentrated under reduced pressure and freeze-dried to obtain 160 mg (yield: 24%) of the above identified compound.

MP 185° C. (decomposed)

IR(KBR)cm$^{-1}$: 3400, 1762, 1602

NMR(DMSO-d$_6$)δ: 3.50(2H,m), 3.86(3H,s), 4.36(1H,d,J=12Hz), 4.58(1H,d,J=12Hz), 5.00(1H,d,J=5Hz), 5.58(1H,dd,J=5 and 8Hz), 6.74(1H,s), 6.80(1H,d,J=8Hz), 7.17(1H,br s), 7.18(1H,dd,J=2 and 8Hz), 7.39(1H,d,J=2Hz), 7.63(1H,s), 9.50(1H,br d,J=8Hz)

EXAMPLE 40

Preparation of sodium 3-[4-(3,4-diacetoxyphenyl)-thiazol-2-yl]thiomethyl-7β-[2-(2-aminothiazol-4-yl)-2-methoxyviminoacetamido]-3-cephem-4-carboxvlate (syn-isomer)

The same operation as in EXAMPLE 4 was conducted by using 1.0 g (1.1 mmol) of benzhydryl 3-iodomethyl-7β-[2-methoxyimino-2-(2-tritylaminothiazol-4-yl)acetamido]-3-cephem-4-carboxylate (syn-isomer) and 0.23 g (1.1 mmol) of 4-(3,4-dihydroxyphenyl)-2-mercaptothiazole, whereby 225 g (yield: 28.1%) of the above identified compound.

MP: 170° C. (decomposed)

IR(KBr)cm : 3440, 1765, 1620

NMR(DMSO-d$_6$)δ: 2.30(6H,s), 3.50(2H,m), 3.85(3H,s), 4.38(1H,d,J=12Hz), 4.60(1H,d,J=12Hz), 5.00(1H,d,J=5Hz), 5.60(1H,dd,J=5 and 8Hz), 6.72(1H,s), 7.20(2H,br s), 7.32(1H,d,J=8Hz), 7.80(1H,br s), 7.82(1H,br d,J=8Hz), 8.02(1H,s), 9.50(1H,br d,J=8Hz)

EXAMPLE 41

Preparation of sodium 7β-[2-(2-aminothiazol-4-yl)-2-isooropoxyiminoacetamido]-3-[4-(3,4-dihydroxyphenyl)-thiazol-2-yl]thiomethyl-3-cechem-4-carboxylate (synisomer)

The same operation as in EXAMPLE 1 was conducted by using 1.0 g (1.1 mmol) of benzhydryl 3-iodomethyl-7β-[2-isopropoxyimino-2-(2-tritylaminothiazol -4-yl)acetamido]3-cephem-4-carboxylate (syn-isomer) and 0.5 g (2.2 mmol) of 4-(3,4-dihydroxyphenyl)-2-mercaptothiazole, whereby 161 g (yield: 22.8%) of the above identified compound was obtained.

MP: 185° C. (decomposed)

IR(KBr)cm$^{-1}$: 3430, 1762, 1605

NMR(DMSO-d$_6$)δ: 1.23(6H,d,J=6Hz), 3.55(2H,m), 4.32(1H,m), 4.42(1H,d,J=15Hz), 4.60(1H,d,J=15Hz), 5.05(1H,d,J=5Hz), 5.65(1H,dd,J=5 and 8Hz), 6.73(1H,s), 6.82(1H,d,J=8Hz), 7.23(1H,br d,J=8Hz), 7.40(1H,br s), 7.62(1H,s), 9.43(1H,br d,J=8Hz)

EXAMPLE 42

Preparation of sodium 78-[2-allyloxyimino-2-(2-aminothiazol-4-yl) acetamido]-3-[4-(3,4-dihydroxyphenyl)-thiazol-2-yl]thiomethyl-3-cephem-4-carboxylate (synisomer)

The, same operation as in EXAMPLE 1 was conducted by using 1.0 g (1.1 mmol) of benzhydryl 3-iodomethyl-7β-[2-allyloxyimino-2-(2-tritylaminothiazol-4-yl)acetamido]-3-cephem-4-carboxylate (syn-isomer) and 0.5 g (2.2 mmol) of 4-(3,4-dihydroxyphenyl)-2-mercaptothiazole, whereby 182 g (yield: 26.9%) of the above identifed compound was obtained.

MP: 175° C. (decomposed)

IR(KBr)cm$^{-1}$: 3420, 1760, 1600

NMR(DMSO-d$_6$)δ: 3.56(2H,m), 4.50(2H,m), 4.62(2H,br d,J=5Hz), 5.03(1H,d,J=5Hz), 5.23(1H,m), 5.30(1H,br d,J=24Hz), 5.63(1H,m), 5.80–6.30(1H,m), 6.75(1H,s), 6.80(1H,d,J=8Hz), 7.20(1H,dd,J=2 and 8Hz), 7.36(1H,d,J=2Hz), 7.62(1H,s), 9.54(1H,m)

EXAMPLE 43

Preparation of disodium 7β-[2-(2-aminothiazol-4-yl)-2-carboxylatemethoxyiminocacetamido]-3-[4-(3,4-dihydroxyphenyl)thiazol-2-yl]thiomethvl-3-cephem-4-carboxylate (syn-isomer)

The same operation as in EXAMPLE 1 was conducted by using 1.0 g (0.88 mmol) of benzhydryl 7β-[2-benzhydryl-oxycarbonylmethoxyimino-2-(2-tritylaminothiazol-4-yl)acetamido]-3-iodomethyl-3-cephem-4-carboxylate and 0.23 g (1.1 mmol) of 4-(3,4-dihydroxyphenyl)-2-mercaptothiazole, whereby 149.mg (yield: 24.9%) of the above identified compound.

MP: 175° C. (decomposed)

IR(KBr)cm$^{-1}$: 3430, 1762, 1602

NMR(DMSO-d$_6$)δ: 3.52(2H,m), 4.30(2H,m), 4.48(2H,m), 5.02(1H,d,J=5Hz), 5.62(1H,m), 6.74(1H,d,J=8Hz), 6.82(1H,s), 7.10(1H,br d,J=8Hz), 7.31(1H,br s), 7.58(1H,s)

EXAMPLE 44

Preparation of disodium 7β-[2-(2-aminothiazol-4-yl)-2-(1-carboxylate-1-methylethoxyimino) acetamido]-3-[4-(3,4-dihydroxyphenyl) thiazol-2-yl]thiomethyl-3-cephem-4-carboxylate (syn-isomer)

The same operation as in EXAMPLE 1 was conducted by using 1.2 g (1.0 mmol) of benzhydryl 7β-[2-(1-benzhydryl-oxycarbonyl-1-methylethoxyimino)-2-(2-tritylaminothiazol-4-yl) acetamido]-3-iodomethyl-3-cephem-4-carboxylate (synisomer) and 0.23 g (1.1 mmol) of 4-(3,4-dihydroxyphenyl)-2-mercaptothiazole, whereby 170 mg (yield: 24.4%) of the above identified compound.

MP: 180°) C. (decomposed)

IR(KKBr)cm$^{-1}$: 3420, 1762, 1590

NMR(DMSO-d$_6$)δ: 3.73(2H,m), 4.25(1H,d,J=13Hz), 4.50(1H,d,J=13Hz), 5.18(1H,d,J=5Hz), 5.82(1H,dd,J=5 and 8Hz), 6.78(1H,d,J=9Hz), 6.82(1H,s), 7.22(1H,br d,J=9Hz), 7.32(1H,br s), 7.70(1H,s), 9.45(1H,br d,J=8Hz)

EXAMPLE 45

Preparation of disodium 7β-[2-(2-aminothiazol-4-yl)-2-(1-carboxvlate-1-cyclopropoxyimino) acetamido]-3-[4-(3,4-dihvdroxvphenyl) thiazol-2-yl]thiomethyl-3-cephem-4-carboxylate (syn-isomer)

The same operation as in EXAMPLE 1 was conducted by using 1.0 g (0.96 mmol) of benzhydryl 7β-[2-(1-t-butoxy-carbonyl-1-cyclopropoxyimino)-2-(2-tritylaminothiazol-4yl)acetamido]-3-iodomethyl-3-cephem-4-carboxylate (synisomer) and 0.23 g (1.1 mmol) of 4-(3,4-dihydroxyphenyl)-2-mercaptothiazole, whereby 60 mg (yield: 8.55%) of the above identified compound.

MP 170° C. (decomposed)

IR(KBr)cm$^{-1}$: 3420, 1762, 1595

NMR(DMSO-d$_6$)δ: 1.15(4H,m), 3.42(1H,d,J=18Hz), 3.66(1H,d,J=18Hz), 4.40(1H,d,J=12Hz), 4.62(1H,d,J=12Hz), 5.02(1H,d,J=5Hz), 5.60(1H,m), 6.80(1H,d,J=8Hz), 6.85(1H,s), 7.16(1H,br d,J=8Hz), 7.36(1H,br s), 7.61(1H,s)

EXAMPLE 46

Preparation of sodium 7β-[2-(2-aminothiazol-4-yl)-benzyloxyiminoacetamido]-3-[4-(3,4-dihydroxyphenyl)-thiazol-2-yl]thiomethyl-3-cephem-4-carboxylate (synisomer)

The same operation as in EXAMPLE 1 was conducted by using 1.0 g (1.0 mmol) benzhydryl 7β-[2-benzyloxyimino-2-(2-tritylaminothiazol-4-yl) acetamido]-3-iodomethyl-3-cephem-4-carboxylate (syn-isomer) and 0.37 g (1.5 mmol) of 4-(3,4-dihydroxyphenyl)2-mercaptothiazole, whereby mg (yield: 9.3%) of the above identified compound.
MP: 180° C. (decomposed)
IR(KBr)cm$^{-1}$: 3420, 1760, 1610
NMR(DMSO-d$_6$)δ: 3.45(1H,d,J=18Hz), 3.67(1H,d,J=18Hz), 4.52(2H,m), 5.05(1H,d,J=5Hz), 5.18(2H,br s), 5.66(1H,d,J=5Hz), 6.77(1H,s), 6.85(1H,d,J=8Hz), 7.10–7.50(8H,m), 7.76(1H,s)

EXAMPLE 47

Preparation of sodium 7β-[2-(2-aminothiazol-4-yl)-2-(3,4-dihydroxybenzyloxyimino) actamido]-3-[4-(3,4-dihydroxyphenyl) thiazol-2-yl]thiomethyl-3-cephem-4-carboxylate (syn-isomer)

The same operation as in EXAMPLE 1 was conducted by using 1.0 g (0.82 mmol) of benzhydryl 3-iodomethyl-7β-{2[3,4-di (2-methoxyethoxymethoxy)-benzyloxyimino]-2-(2-tritylaminothiazol-4-yl) acetamido}-3-cephem-4-carboxylate (syn-isomer) and 0.3 g (1.3 mmol) of 4-(3,4-dihydroxyphenyl)-2-mercaptothiazole, whereby 285 mg (yield: 45.9%) of the above identified compound was obtained.
MP: 160° C. (decomposed)
IR(KBr)cm$^{-1}$: 3430, 1762, 1610
NMR(DESO-d$_6$)δ: 3.55(2H,m), 4.52(2H,m), 5.00(1H.d,J=5Hz), 5.04(2H,br s), 5.60(1H,m), 6.70(1H,s), 6.75(3H,m), 7.18(1H,br d,J=8Hz), 7.36(2H,m), 7.59(1H,s), 9.32(1H,br d,J=8Hz)

EXAMPLE 48

Preparation of sodium 7β-[2-(2-aminothiazol-4-yl)-2-ethoxyiminoacetamido]-3-[4-(3, 4-dihydroxyphenyl)-thiazol-2-yl]thiomethyl-3-cephem-4-carboxylate (syn-isomer)

A filtrate obtained by the same operation as in EXAMPLE 1 by using 516 mg (0.547 mmol) of benzhydryl 7 β[2-ethoxyimino-2-(2-tritylaminothiazol-4-yl)acetamido]-3-iodomethyl-3-cephem-4-carboxylate (syn-isomer) and 123 mg (0.507 mmol) of 4-(3,4-dihydroxyphenyl)-2mercaptothiazole, was subjected to ODS reversed phase column chromatography (LC Sorb RP-18, manufactured by Kemco Co.1: and eluted with a 30% methanol aqueous solution. The fraction containing the desired compound was concentrated under reduced pressure and freeze-dried to obtain 133 mg (yield: 34.9%) of the above identified compound.
MP: 200° C. (decomposed)
IR(KBr)cm$^{-1}$: 3430, 1765, 1605, 1530
NMR(DMSO-d$_6$)δ: 1.12(3H,t,J=7Hz), 3.60(2H,m), 4.08(2H,q,J=7Hz), 4.30(1H,br d,J=12Hz), 4.53(1H,br d,J=12Hz), 4.98(1H,d,J=5Hz), 5.58(1H,dd,J=5 and 8Hz), 6.68(1H,s), 6.75(1H,d,J=9Hz), 7.12(1H,dd,J=2 and 9Hz), 7.32(1H,d,J=2Hz), 7.57(1H,s), 9.42(1H,br d,J=8Hz)

EXAMPLE 49

Preparation of sodium 3-[4-(3,4-diacetoxyphenyl)-thiazol-2-yl]thiomethyl-7β-[2-(2-aminothiazol-4-yl)-2-ethoxyiminoacetamido]-3-cephem-4-carboxylate (synisomer)

A filtrate obtained by the same operation as in EXAMPLE 4 by using 10.6 g (11.2 mmol) of benzhydryl 7β-[2-ethoxyimino-2-(2-tritylaminothiazol-4-yl)acetamido]-3-iodomethyl-3-cephem-4-carboxylate (syn-isomer), 3.5 g (15.5 mmol) of 4-(3,4-dihydroxyphenyl)-2-mercaptothiazole, 10.6 ml (0.11 mmol) of acetic anhydride and 9.1 ml (0.11 mmol) of pyridine, was subjected to ODS reversed phase column chromatography (LC-Sorb RP-18, manufactured by Kemco Co.) and eluted with a 30% methanol aqueous solution. The fraction containing the desired product was concentrated under reduced pressure and freeze-fried to obtain 2.83 g (yield: 33.9%) of the above identified compound.
MP: 190° C. (decomposed)
IR(KBr)cm$^{-1}$: 3430, 1765, 1605, 1530
NMR(DMSO-d$_6$)δ: 1.21(3H,t,J=7Hz), 2.30(6H,s), 3.30-3.80(2H,m), 4.10(2H,q,J=7Hz), 4.40(1H,br d,J=12Hz), 4.64(1H,br d,J=12Hz), 5.01(1H,d,J=5Hz), 5.60(1H,dd,J=5 and 8Hz), 6.70(1H,s), 7.18(2H,br s), 7.32(1H,d,J=9Hz), 7.80(1H,s), 7.82(1H,d,J=9Hz), 8.02(1H,s), 9.45(1H,br d,J=8Hz)

EXAMPLE 50

Preparation of trisodium 7β-[2-(2-aminothizaol-4-yl)-2-(1-carboxylate-1-methylethoxyimino) acetamido]-3-[4-carboxylate-5-(3,4-dihydroxyphenyl) thiazol-2-yl]-thiomethyl-3-cephem-4-carboxylate (syn-isomer)

(A) 11.9 g (11 mmol) of benzhydryl 7β-[2-(1-benzhydryl-oxycarbonyl-1-methylethoxyimino)-2-( 2-tritylaminothiazol-4-yl)acetamido]-3-chloromethyl-3-cephem-4-carboxylate (syn-isomer) was dissolved in 90 ml of N,N-dimethylformamide, and 8.3 g (55 mmol) of sodium iodide was added thereto. The mixture was stirred for 1 hour. To the reaction solution 3.0 g (11.1 mmol) of 4-carboxy-5-(3,4-dihydroxyphenyl)-2-mercaptothiazole and 1.55 ml (11.1 mmol) of triethylamine were added and stirred at the same temperature for 45 minutes. The solvent was distilled off under reduced pressure, and to the residue 500 ml of ethyl acetate and 150 ml of water were added. The solution was adjusted to pH1.5 with 2N hydrochloric acid. The organic layer was washed sequentially with 150 ml of 5% sodium thiosulfate aqueous solution and 150 ml of a saturated sodium hydrochloride aqueous solution, dried over anhydrous magnesium sulfate and concentrated under reduced pressure. The residue was subjected to silica gel column chromatography (Wakogel C-300, elution with a 2% methanol chloroform) to obtain 12.2 g (yield: 84%) of benzhydryl 7β-[2-(1-benzhydryloxycarbonyl-1-methylethoxyimino)-2-( 2-tritylaminothiazol-4-yl)-acetamido]-3-[4-carboxy-5-(3, 4-dihydroxyphenyl)-thiazol-2-yl]thiomethyl-3-cephem-4-carboxylate (syn-isomer).
IR(KBr)cm$^{-1}$: 1790, 1730, 1690, 1530, 1500, 1280, 1180, 1160

NMR(DMSO-d$_6$)δ: 1.52(6H,s), 3.75(2H,br s), 4.25(2H,ABq), 5.21(1H,d,J=4.5Hz), 5.80(1H,dd,J=4.5 and 9.0Hz), 6.67(1H,s), 6.75(1H,s), 6.77(2H,s), 6.90(1H,s), 6.93(1H,s), 7.30(35H,s), 8.77(1H,br s), 9.15(1H,br s), 9.33(1H,br s), 9.38(1H,d,J=9.0Hz)

(B) 12.1 g (9.22 mmol) of the compound obtained in the above reaction (A) was dissolved in 50 ml of methylene chloride and 10 ml of anisole, and 50 ml of trifluoroacetate was dropwise added thereto in 25 minutes under cooling with ice. The mixture was stirred at room temperature for 2 hours. The reaction solution was concentrated under reduced pressure, and 200 ml of diisopropyl ether was added to the oily residue. Insoluble substances were collected by filtration, and the insoluble substances were dissolved in 36.3 ml of formic acid Then 8.1 ml of concentrated hydrochloric acid was added thereto. The mixture was stirred at room temperature for 1 hour, and 500 ml of diisopropyl ether was added thereto and stirred for 15 minutes. The precipitates were collected by filtration, washed with 50 ml of diisopropyl ether, and dried under reduced pressure to obtain 6.23 g (yield: 87%) of a hydrochloride of the above identified compound as a powdary substance.

IR(KBr)cm$^{-1}$: 1770, 1720, 1680, 1630, 1530, 1370, 1280, 1170

NMR(DMSO-d$_6$)δ: 1.53(6H,s), 3.75(2H,ABq), 4.34(2H,ABq), 5.22(1H,d,J=4.5Hz), 5.87(1H,dd,J=4.5 and 9.0Hz), 6.77(2H,s), 6.90(1H,s), 7.00(1H,s), 8.20(5H,br s), 9.62(1H,d,J=9.0Hz)

(C) 6.0 g (7.76 mmol) of the hydrochloride obtained in the above reaction (B) was suspended in 80 ml of water and adjusted to pH7.3 with a saturated sodium hydrogen carbonate under cooling with ice. Insoluble substances were filtered off, and the filtrate was subjected to reversed phase column chromatography (LC-Sorb RP-18, manufactured by Kemco Co., 360 ml, elution with water). The fraction containing the desired product was concentrated and freeze-dried to obtain 3.94 g (yield: 61%) of the above identified compound.

MP: 260° C. (decomposed)

IR(KBr)cm$^{-1}$: 1760, 1670, 1590, 1530, 1400, 1360

NMR(D$_2$O)δ: 1.50(6H,s), 3.60(2H,ABq), 4.19(2H,ABq), 5.17(1H,d,J=4.5Hz), 5.77(1H,d,J=4.5Hz), 6 91(2H,s), 6.97(1H,s), 6.99(1H,s)

EXAMPLE 51

Preparation of trisodium 78-[2-(2-aminothiazol-4-yl)-2-(o-carboxylatebenzyloxyimino) acetamido]-3-[4-carboxylate-5-(3,4-dihydroxyphenyl) thiazol-2-yl]-thiomethyl-3-cephem-4-carboxylate (diastereomer A and B, syn-isomer)

The same operation as in EXAMPLE 50 was conducted by using 1.58 g (1.4 mmol) of benzhydryl 7β-[2-(α-benzhydryloxycarbonylbenzyloxyimino)-2-( 2-tritylaminothiazol-4-yl)acetamido]-3-chloromethyl-3-cephem-4-carboxylate (syn-isomer), 1.05 g (7 mmol) of sodium iodide, 414 mg (1.57 mmol) of 4-carboxy-5-(3,4-dihydroxyphenyl)-2mercaptothiazole and 0.215 ml (1.54 mmol) of trietylamine, whereby 240 mg (yield: 21.1%) of diastereomer A and 210 mg (yield: 18.6%) of diastereomer B were obtained.

Diastereomer A
MP: 270° C. (decomposed)
IR(KBr)cm$^{-1}$: 1760, 1660, 1590, 1530, 1400, 1380
NMR(D$_2$O)δ: 3.31(2H,ABq), 4.12(2H,ABq), 5.02(1H,d,J=4.5Hz), 5.54(1H,s), 5.66(1H,d,J=4.5Hz), 6.90(2H,s), 6.99(2H,s), 7.38(5H,m)

Diastereomer B
MP: 270° C. (decomposed)
IR(KBr)cm$^{-1}$: 1760, 1660, 1590, 1530, 1400, 1380
NMR(D$_2$O)δ: 3.27(2H,ABq), 4.13(2H,ABq), 4.99(1H,d,J=4.5Hz), 5.54(1H,s), 5.62(1H,d,J=4.5Hz), 6.90(2H,s), 6.97(2H,s), 7.38(5H,m)

EXAMPLE 52

Preparation of disodium 7β-[2-(2-aminothiazol-4-yl)-2-methoxyiminoacetamido-3-[4-carboxylate-5-(3,4-dihydroxyphenyl) thiazol-2-yl]thiomethyl-3-cephem-4-carboxylate (syn-isomer)

A hydrochloride obtained by the same operation as in EXAMPLE 50 by using 1.26 g (1.5 mmol) of benzhydryl 3-chloromethyl-7β-[2-methoxyimino-2-(2-tritylaminothiazol-4-yl) acetamido]-3-cephem-4-carboxylate (synisomer), 1.12 g (7.5 mmol) of sodium iodide, 444 mg (1.65 mmol) of 4-carboxy-5-(3,4-dihydroxyphenyl)-2-mercaptothiazole and 0.23 ml (1.65 mmol) of triethylamine, was neutralized with a saturated sodium hydrogencarbonate aqueous solution and subjected to reversed phase column chromatography (LC-Sorb RP-18, manufactured by Kemco Co. 180 ml, elution with a 5% methanol aqueous solution) to obtain 320 mg (yield: 20.6%) of the above identified compound.

MP: 220-230° C. (decomposed)
IR(KBr)cm$^{-1}$: 1765, 1660, 1600, 1540, 1405, 1390
NMR(D$_2$O)δ: 3.57(2H,ABq), 3.97(3H,s), 4.17(2H,ABq), 5.13(1H,d,J=4.5Hz), 5.73(1H,d,J=4.5Hz), 6.88(2H,s), 6.98(2H,s)

EXAMPLE 53

Preparation of disodium 7β-[2-(2-aminothiazol-4-yl)-2-ethoxyiminoacetamido]-3-[4-carboxylate-5-(3,4-dihydroxyphenyl)thiazol-2-yl]thiomethyl-3-cephem-4-carboxylate (syn-isomer)

A hydrochloride obtained by the same reaction as in EXAMPLE 50 by using 1.42 g (1.5 mmol) of benzhydryl 7β-[2-ethoxyimino-2-(2-tritylaminothiazol-4-yl) acetamido]-3-iodomethyl-3-cephem-4-carboxylate (syn-isomer), 444 mg (1.65 mmol) of 4-carboxy-5-(3,4-dihydroxyphenyl)-2-mercaptothiazole and 0.23 ml (1.65 mmol) of triethylamine, was neutralized with a saturated sodium hydrogencarbonate aqueous solution and subjected to reversed phase column chromatography (LC Sorb RP-18, 180 ml, elution with a 5% methanol aqueous solution, to obtain 320 mg (yield: 36.9%) of the above identified compound.

MP: 270° C. (decomposed)
IR(KBr)cm$^{-1}$: 1760, 1660, 1600, 1530, 1410, 1380
NMR(D$_2$O)δ: 1.28(3H,t,J=7.0Hz), 3.58(2H,ABq), 4.11(2H,ABq), 4.25(2H,q,J=7.0Hz), 5.13(1H,d,J=4,5Hz), 5.72(1H,d,J=4.5Hz), 6.85(2H,s), 6.95(2H,s)

EXAMPLE 54

Preparation of disodium
78-[2-(2-aminothiazol-4-yl)-2-cyclopentyloxyiminoacetamido]-3-[4-carboxylate-5-(3,4-dihydroxyphenyl)
thiazol-2-yl]thiomethyl-3-cephem-4-carboxylate
(syn-isomer)

A hydrochloride obtained by the same operation as in EXAMPLE 50 by using 890 mg (1 mmol) of benzhydryl 3-chloromethyl-78-[2-cyclopentyloxyimino-2-(2-tritylaminothiazol-4-yl) acetamido]-3-cephem-4-carboxylate, 750 mg (5 mmol) of sodium iodide, 300 mg (1.1 mmol) of 4-carboxy-5-(3,4-dihydroxyphenyl)-2-mercaptothiazole and 0.15 ml (1.1 mmol) of triethylamine, was neutralized with a saturated sodium hydrogencarbonate aqueous solution and subjected to reversed phase column chromatography (LC Sorb RP-18, 180 ml, elution with a 5% methanol aqueous solution) to obtain 150 mg (yield: 21.5%) of the above identified compound.

MP: 165°–170° C. (decomposed)

IR(KBr)cm$^{-1}$: 1760, 1650, 1600, 1530, 1400, 1380

NMR(D$_2$O)δ: 1.40–2.00(8H,m), 3.55(2H,ABq), 4.16(2H, ABq), 4.80(1H,br s), 5.14(1H,d,J=4.5Hz), 5.72(1H,d,J=4.5Hz), 6.86(2H,s), 6.92(1H,s), 6.96(1H,s)

EXAMPLE 55

Preparation of disodium 78-[2-allyloxyimino-2-(2-aminothiazol-4-yl) acetamido]-3-[4-carboxylate-5-(3,4-dihydroxyphenyl) thiazol-2-yl]thiomethyl-3-cephem-4-carboxylate (syn-isomer)

A hydrochloride obtained by the same operation as EXAMPLE 50 by using 1.30 g (1.5 mmol) of benzhydryl 7β-[2-allyloxyimino-2-(2-tritylaminothiazol-4-yl)acetamido ]-3-chloromethyl-1-3-cephem-4-carboxylate (syn-isomer), 1.13 g (7.5 mmol) of sodium iodide, 444 mg (1.65 mmol) of 4-carboxy-5-(3,4-dihydroxyphenyl)-2-mercaptothiazole and 0.23 ml (1.65 mmol) of triethylamine, was neutralized with a saturated sodium hydrogencarbonate aqueous solution and subjected reversed phase column chromatography (LC Sorb RP-18, 180 ml, elution with a 5% methanol aqueous solution) to obtain 160 mg (yield: 14.5%) of the above identified compound.

MP: 270° C.

IR(KBr)cm$^{-1}$: 1760, 1660, 1595, 1530, 1405, 1380

NMR(D$_2$O)δ: 3.57(2H,ABq), 4.07(2H,ABq), 5.17(1H,d,J=4.5Hz), 5.10–5.50(5H,m), 5.76(1H,d,J=4.5Hz), 6.90(1H,s), 7.00(1H,s)

EXAMPLE 56

Preparation of disodium
78-[2-(2-aminothiazol-4-yl)-2-proparqyloxyiminoacetamido]-3-[4-carboxylate-5-(3,4-dihydroxyphenyl)
thiazol-2-yl]thiomethyl-3-cephem-4-carboxylate
(syn-isomer) A hydrochloride obtained by the same operation as in EXAMPLE 50 by using 1.30 g (1.5 mmol) of benzhydryl 3-chloromethyl-7β-[2-propargyloxyimino-2-(2-tritylaminothiazol-4-yl) acetamido]-3-cephem-4-carboxylate (syn-isomer), 1.13 g (7.5 mmol) of sodium iodide, 444 mg (1.65 mmol) of 4-carboxy-5-(3,4-dihydroxyphenyl)-2-mercaptothiazole and 0.23 ml (1.65 mmol) of triethylamine, was neutralized with a saturated sodium hydrogencarbonate aqueous solution and subjected to reversed phase column chromatography (LC-Sorb RP-18, manufactured by Kemco Co., 180 ml, elution with a 5% methanol aqueous solution) to obtain 410 mg (yield: 40.0%) of the above identified compound.

MP: 270° C.

IR(KBr)cm$^{-1}$: 1760, 1660, 1600, 1530, 1410, 1380

NMR(D$_2$O)δ: 2.97(1H,br s), 3.55(2H,ABq), 4.17(2H,ABq), 4.81(2H,s), 5.16(1H,d,J=4.5Hz), 5.74(1H,d,J=4.5Hz), 6.88(2H,s), 6.98(1H,s), 7.03(1H,s)

EXAMPLE 57

Preparation of disodium
7β-82-(2-aminothiazol-4-yl)-2-benzyloxyiminoacetamido]-3-[4-carboxylate-5-(3,4-dihydroxyphenyl)thiazol-2-yl]thiomethyl-3-cephem-4-carboxylate
(syn-isomer)

A hydrochloride obtained by the same operation as in EXAMPLE 50 by using 1.37 g (1.5 mmol) of benzhydryl 7 β[2-benzyloxyimono-2-(2-tritylaminothiazol-4yl-)acetamido]-3-chloromethyl-3-cephem-4-carboxylate (synisomer), 1.13 g (7.5 mmol) of sodium iodide, 444 mg (1.65 mmol) of 4-carboxy-5-(3,4-dihydroxyphenyl)-2-mercaptothiazole and 0.23 ml (1.65 mmol) of triethylamine, was neutralized with a saturated sodium hydrogencarbonate aqueous solution and subjected to reversed phase column chromatography (LC Sorb RP-18, manufactured by Kemco Co., 180 ml, elution with a 5% methanol aqueous solution) to obtain 140 mg (yield: 10.2%) of the above identified compound.

MP: 270° C.

IR(KBr)cm$^{-1}$: 1660, 1595, 1530, 1405, 1380

NMR(D$_2$O/DMSO-d$_6$)δ: 3.34(2H,ABq), 4.13(2H,ABq), 5.03(1H,d,J=4.5Hz), 5.19(2H,s), 5 67(1H,d,J=4.5Hz), 5.86(2H,s), 5.92(1H,s), 5.99(1H,s), 7.34(5H,m)

EXAMPLE 58

Preparation of disodium
7β-[2-(2-aminothiazol-4-yl)-2-methoxyiminoacetamido]-3-[4-(3,
4-dihydroxyphenyl)-5-carboxylatemethylthiazol-2-yl]thiomethyl-3-cephem-4-carboxylate (syn-isomer)

A trifluoroacetate obtained by the same operation as in EXAMPLE 1 by using 524 mg (0.56 mmol) of benzhydryl 3-iodomethyl-7β-[2-methoxyimino-2-(2-tritylaminothiazol-4-yl) acetamido]-3-cephem-4-carboxylate (synisomer) and 300 mg (0.56 mmol) of 4-(3,4-diacetoxyphenyl)-5-benzhydryloxycarbonylmethyl-2- mercaptothiazole obtained in REFERENCE EXAMPLE 32 given hereinafter, was dissolved in a saturated sodium hydrogencarbonate aqueous solution and washed with ethyl acetate. The water layer was subjected to reversed phase column chromatography (LC-Sorb RP-18, manufactured by Kemco Co.) and eluted with a 10% methanol aqueous solution. The fraction containing the desired compound was concentrated and freeze-dried to obtain 86 mg (yield: 21.1%) of the above identified compound.

MP: 185–190° C. (decomposed)
IR(KBr)cm$^{-1}$: 3420, 1760, 1600, 1530, 1390
NMR(DMSO-d$_6$)δ: 3.52(4H,m), 3.82(3H,s), 4.26(1H,d,J=12.0HZ), 4.55(1H,d,J=12.0Hz), 5.00(1H,d,J=5.0Hz), 5.62(1H,d,J=5.0Hz), 6.76(1H,s), 6.78(1H,d,J=20.0Hz), 6.98(1H,dd,J=3.0 and 20.0Hz), 7.24(1H,d,J=3.0Hz)

EXAMPLE 59

Preparation of trisodium 7β-[2-(2-aminothiazol-4-yl)-2-(1-carboxylate-1-methylethoxyimino) acetamido]-3-[4-(3,4-dihydroxyphenyl)-5-carboxylatemethylthiazol-2yl]thiomethyl-3-cephem-4-carboxylate (I) and trisodium 7β-[2-(2-aminothiazol-4-yl)-2-(1-carboxylate-1-methylethoxyimino) acetamido]-3-[4-(3,4-diacetoxyphenyl)-5-carboxylatemethylthiazol-2-yl]-thiomethyl-3-cephem-4-carboxylate (II) (syn-isomer)

(A) 1.0 g (0.85 mmol) of benzhydryl 7β-[2-(1-benzhydryloxycarbonyl-1-methylethoxyimino)-2-(2-tritylaminothiazol-4-yl)acetamido]-3-iodomethyl-3-cephem-4carboxylate (syn-isomer) was dissolved in 10 ml of N,N-dimethylformamide, and 0.45g (0.84 mmol) of 4-(3,4-diacetoxyphenyl)-5-benzhydryloxycarbonylmethyl-2-mercaptothiazole was added. The mixture was stirred at room temperature for 1 hour. The solvent was distilled off under reduced pressure, the residue was purified by silica gel column chromatography (Wakogel C-300, ethyl acetate:hexane=1:3). The fraction containing the desired product was concentrated to obtain 692 mg (yield: 51%) of benzhydryl 3-[4-(3,4-diacetoxyphenyl)-5-benzhydryloxycarbonylmethylthiazol-2-yl]thiomethyl-7δ-[2-(1-benzhydryloxycarbonyl-1-methylethoxyimino)-2-(2-trityl aminothiazol-4-yl)acetamido]-3-cephem-4-carboxylate (syn-isomer) as a foamy substance.

NMR(DMSO-d$_6$)δ: 1.52(6H,br s), 2.30(6H,s), 3.78(2H,m), 4.10–4.40(4H,m), 5.25(1H,d,J=5.0Hz), 5.90(1H,m), 6.70–7.80(49H,m),
8.90(1H,br s), 9.48(1H,br d,J=8.0Hz)

(B) 692 mg (0.44 mmol) of the compound obtained in the above reaction (A) was dissolved in 3.0 ml of methylene chloride and 0.7 ml of anisole, and 3.0 ml of trifluoroacetic acid was added thereto under cooling with ice. The mixture was stirred for 1 hour. The solvent was distilled off under reduced pressure, and to the residue ethyl ether was added. The precipitates were collected by filtration and suspended in water. The suspension was adjusted to pH6.5 with a saturated sodium hydrogencarbonate aqueous solution and subjected to reversed phase column chromatography (LC Sorb RP-18, manufactured by Kemco Co.) and the fraction containing the desired produced was collected by elution with water followed by freeze-drying, whereby 136 mg (yield: 38%) of the above identified compound (I). By further elution with a 5% methanol aqueous solution, 89 mg (yield: 22%) of the above identified compound (II) was obtained.

Compound (I)
MP: 175–180° C. (decomposed)
IR(KBrcm$^{-1}$: 3400, 1760, 1585, 1535, 1400
NMR(DMSO-d$_6$)δ: 1.40(3H,br s), 1.46(3H,br s), 4.20(1H,d,J=12.0Hz), 4.54(1H,d,J=12.0Hz), 5.02(1H,d,J=5.0Hz), 5.68(1H,m), 6.76(1H,s), 6.80(1H,d,J=7.0Hz), 6.96(1H,br d,J=7.0Hz), 7.13(1H,br s)

Compound (II)
MP: 195°–200° C. (decomposed)
IR(KBr)cm$^{-1}$: 3420, 1760,1660,1595, 1535, 1370
NMR(DMSO-d$_6$)δ: 1.40(3H,br s), 1.45(3H,br s), 2.28(6H,s), 4.18(1H,m), 4.70(1H,m), 5.00(1H,m), 6.70(1H,s), 7.10-7.70(3H,m)

EXAMPLE 60

Preparation of trisodium 7β-[2-(2-aminothiazol-4-yl)-2-(1-carboxylate-1-cyclopropoxyimino) acetamido]-3-[4-(3,4-dihydroxyphenyl)-5-carboxylatemethylthiazol-2-yl]thiomethyl-3-cephem-4-carboxylate (I) and trisodium 3-[4-(3,4-diacetoxyphenyl)-5-carboxylate-methylthiazol-2-yl]thiomethyl-7δ-[2-(2-aminothiazol-4-yl)-2-(1-carboxylate-1-cyclopropoxyimino) acetamido]-3-cephem-4-carboxylate (II) (syn-isomer)

A trifluoroacetate obtained by the same operation as in EXAMPLE 59 by using 1.0 g (0.96 mmol) of benzhydryl 7β-[2 (1-tert-butoxycarbonyl-1-cyclopropoxyimino)-2-(2-tritylaminothiazol-4-yl) acetamido]-3-iodomethyl-3-cephem-4-carboxylate (syn-isomer) and 0.51 g (0.96 mmol) of 4-(3,4-diacetoxyphenyl)-5-benzhydryloxycarbonyl-2-mercaptothiazole, was suspended in water and adjusted to pH6.5 with a saturated sodium hydrogencarbonate aqueous solution. The suspension was subjected to reversed phase column chromatography (LC-Sorb RP-18, manufactured by Kemco Co.) and the fraction containing the desired product was collected by elution with water followed by freeze-drying, whereby 61 mg (yield: 7.8%) of the above identified compound (I). By further elution with a 5% methanol aqueous solution 173 mg (yield: 20%) of above identified compound (II) was obtained.

Compound (I)
MP: 165–170° C. (decomposed)
IR(KBr)cm$^{-1}$: 3420, 1760, 1600, 1535, 1400
NMR(DMSO-d$_6$)δ: 1.05(2H,m), 1.16(2H,m), 5.00(1H,m), 6.80(1H,s)

Compound (II)
MP: 165°–170° C. (decomposed)
IR(KBr)cm$^{-1}$: 3420, 1760, 1590, 1535, 1410
NMR(DMSO-d$_6$)δ: 1.06(2H,m), 1.22(2H,m), 2.28(6H,s), 4.20(1H,m), 4.60(1H,m), 4.98(1H,d,J=5.0Hz), 5.55(1H,d,J=5.0Hz), 6.80(1H,s), 7.25(1H,d,J=9.0Hz), 7.55(1H,br s), 7.58(1H,m)

EXAMPLE 61

Preparation of trisodium 3-[4-(3,4-diacetoxyphenyl-5-carboxylatemethylthiazol-2-yl]thiomethyl-7β-[2-(2-aminothiazol-4-yl]-2-(α-carboxylatebenzyloxyimino)-acetamido]-3-cephem-4-carboxylate (diastereomer A and B, syn-isomer)

A trifluoroacetate obtained by the same operation as in EXAMPLE[59] by using 1.0 g (0.82 mmol) of benzhydryl 7β-[2-(α-benzhydryloxycarbonylbenzyl oxyimino)-2-( 2-tritylaminothiazol-4-yl)acetamido]-3-iodomethyl-3-cephem-4-carboxylate (syn-isomer) and 0.44 g (0.82 mol) of 4-(3, 4-diacetoxyphenyl)-5-benzhydryloxycarbonylmethyl-2mercaptothiazole, was suspended in water and adjusted to pH6.5 with a saturated sodium hydrogencarbonate aqueous solution. The suspension was subjected to reversed phase column chromatography (LC-Sorb RP-18, manufacture by Kemco Co.) and eluted with a 5% methanol aqueous solution to separate diastereomer A and B. The respective fractions were collected, concentrated and freeze-dried to obtain 103 g (yield: 13%) of diastereomer A and 164 mg (yield: 21%) of diastereomer B.

High-performance liquid chromatography analysis
Column: ODS (YMC-PACK A-312) 6×150 mm
Mobile phase: 60% MeOH-0.01M Phosphate buffer (PH 3.0)
Flow rate: 1.0 ml/min
Detection: UV 254 nm
Diastereomer A: 12 minutes
Diastereomer B: 13 minutes
Diastereomer A
MP: 185–190° C. (decomposed)
IR(KBr)cm$^{31\ 1}$: 3420, 1760, 1600, 1535, 1380
IR(KBr)cm$^{-1}$: 3420, 1760, 1600
NMR(DMSO-d$_6$)δ: 3.28(6H,s), 4.15(1H,m), 4.65(1H,m), 5.00(1H,d,J=5.0Hz), 5.30(1H,s), 5.70(1H,m), 6.76(1H,s), 7.00–7.70(8H,m)
Diastereomer B
MP: 185–190° C. (decomposed)
IR(KBr)cm$^{-1}$: 3400, 1760, 1600, 1530, 1380
NMR(DMSO-d$_6$)δ: 2.28(6H,s), 4.10–4.80(2H,m), 5.00(1H,m), 5.38(2H,m), 6.88(1H,s), 7.00–7.70(8H,m)

EXAMPLE 62

Preparation of sodium 7β-[2-(2-aminothiazol-4-yl)-2-methoxyiminoacetamido]-3-[5-(3, 4-dihydroxyphenyl)-oxazol-2-yl]thiomethyl-3-cephem-4-carboxylate (synisomer)

A trifluoroacetate obtained by the same operation as in EXAMPLE 1 by using 1.0 g (1.11 mmol) of benzhydryl 3-iodomethyl-7β-[2-methoxyimino-2-(2-tritylaminothiazol-4-yl) acetamido]-3-cephem-4-carboxylate (syn-isomer) and 0.260 g (1.2 mmol) of 5-(3,4-dihydroxyphenyl)-2-mercaptooxazole obtained in REFERENCE EXAMPLE 30 given hereinafter, was suspended in water and adjusted to pH6.5 by a saturated sodium hydrogencarbonate aqueous solution. Insoluble substances were filtered off and the filtrate was subjected to reversed phase column chromatography (LC-Sorb RP-18, manufactured by Kemco Co.). The fraction (elution with a 20% methanol aqueous solution) containing the desired compound was collected, concentrated and freeze-dried to obtain 180 mg (yield: 26.6%) of the above identified compound.
MP: 185° C. (decomposed)
IR(KBR)cm$^{-1}$: 1760, 1660, 1520, 1390, 1360, 1280, 1030
NMR(DOSO-d$_6$/D$_2$O)δ: 3.20–3.60(2H,m), 3.983(3H,s), 4.33(2H,br s), 5.00(1H,d,J=4.5Hz), 5.60(1H,d,j=4.5Hz), 6.77(1H,s), 6.80–7.15(3H,m), 7.35(1H,s)

EXAMPLE 63

Preparation of sodium 7β-[2-(2-aminothiazol-4-yl)-2-ethoxyiminoacetamido]-3-[5-(3, 4-dihydroxyphenyl)-oxazol-2-yl]thiomethyl-3-cephem-4-carboxylate (synisomer)

A trifluoroacetate obtained by the same operation as in EXAMPLE 1 by using 1.0 g (1.06 mmol) of benzhydryl 7β-[2-ethoxyimino-2-(2-tritylaminothiazol-4-yl)acetamido]-3-iodomethyl-3-cephem-4-carboxylate (syn-isomer) and 0.260 g (1.2 mmol) of 5-(3,4-dihydroxyphenyl)-2mercaptooxazole, was suspended in water and adjusted to pH6.5 with a saturated sodium hydrogencarbonate aqueous solution. Insoluble substances were filtered off and the filtrate was subjected to reversed phase column chromatography (LC-Sorb RP-18, manufactured by Kemco Co.). The fraction (elution with a 20% methanol aqueous solution) containing the desired compound was collected, concentrated and freeze-dried to obtain 70 mg (yield: 10.2%) of the above identified compound.
MP: 185° C. (decomposed)
IR(KBr)cm$^{-1}$: 1760, 1620, 1520, 1390, 1040
NMR(DMSO-d$_6$/D$_2$O)δ: 1.23(3H,t,J=6.0Hz), 3.25-3.70(2H,m), 4.13(2H,q,J=6.0Hz), 4.33(2H,br s), 5.00(1H,d,J=4.5Hz), 5.62(1H,d,J=4.5Hz), 6.75(1H,s), 6.80–7.10(3H,m), 7.35(1H,s)

EXAMPLE 64

Preparation of disodium 7β-[2-(2-aminothiazol-4-yl)-2-(1-carboxylate-1-methylethoxyimino) acetamido]-3-[5-(3,4-dihydroxyphenyl) oxazol-2-yl]thiomethyl-3-cephem-4-carboxylate (syn-isomer)

A trifluoroacetate obtained by the same reaction as in EXAMPLE 1 by using 1.0 g (1.06 mmol) of benzhydryl 7β-[2-(1-benzhydryloxycarbonyl-1-methylethoxyimino)-2-(2-tritylaminothiazol-4-yl) acetamido]-3-iodomethyl-3-cephem-4-carboxylate (syn-isomer) and 0.215 g (1.0 mmol) of 5-(3,4-dihydroxyphenyl)-2-mercaptooxazole, was suspended in water and adjusted to pH6.5 with a saturated sodium hydrogencarbonate aqueous solution. Insoluble substances were filtered off and the filtrate was subjected to reversed phase column chromatography (LC-Sorb RP-18, manufactured by Kemco Co.). The fraction (elution with a 7.5% methanol aqueous solution) containing the desired product was collected, concentrated and freeze-dried to obtain 100 mg (yield: 16.3%) of the above identified compound.
MP: 180° C. (decomposed)
IR(KBr)cm$^{-1}$: 1760, 1600, 1530, 1400, 1360, 1280
NMR(DMSO-d$_6$/D$_2$O)δ: 1.42(3H,s), 1.47(3H,s), 3.00–3.70(2H,m), 4.30(2H,m), 5.20(1H,d,J=4.5Hz), 5.65(1H,d,J=4.5Hz), 6.75(1H,s), 6.80–7.15(3H,m), 7.33(1H,s)

EXAMPLE 65

Preparation of disodium
7β-(2-(2-aminothiazol-4-yl)-2-[(α-carboxylate-3,4-dihydroxybenzyl)oxyiminol]-acetamido}-3-[5-(3, 4-dihydroxyphenyl)oxazoi-2-yl]-thiomethyl-3-cephem-4-carboxylate (syn-isomer)

(A) 1.0 g (0.75 mmol) of 7β-{(2-[α-benzhydryloxycarbonyl-3,4-di (2-methoxyethoxymethoxy)benzyloxyimino]-2-(2-tritylaminothiazol-4-yl) acetamido}-3-chloromethyl-3-cephem-4-carboxylate (syn-isomer) was dissolved in 10 ml of N,N-dimethylformamide, and 124 mg (0.83 mmol) of sodium iodide was added thereto. The mixture was stirred at room temperature for 30 minutes. To the reaction solution 0.185 g (0.88 mmol) of 5-(3,4-dihydroxyphenyll-2-mercaptooxazole was added and stirred at room temperature for 3 hours. Ethyl acetate was added to the reaction solution and washed sequentially with water and a saturated sodium hydrochloride aqueous solution, followed by drying over anhydrous sodium sulfate The filtrate was concentrated under reduced pressure and the residue was purified by silica gel column chromatography (Wakogel C-300, chloroform: methanol =98:2). The fraction containing the desired product was concentrated under reduced pressure to obtain 0.80 g (yield: 71%) of benzhydryl 7β-(2-[α-benzhydryloxycarbonyl-3,4di(2-methoxyethoxymethoxy) benzyloxyimino]-2-(2-tritylaminothiazol-4-yl)acetamido)-3-[5-(3, 4-dihydroxyphenyl)-oxazol-2-yl] thiomethyl-3-cephem-4-carboxylate (synisomer).

IR(KBr)cm$^{-1}$: 1 1790, 1730, 1680, 1510, 1450, 1250, 700

NMR(DMSO-d$_6$)δ: 3.17(3H,s), 3.20(3H,s), 3.25-3.50(6H,m), 3.60-3.85(4H,m), 3.95-4.50(2H,m), 5.05-5.35(3H,m), 5.65-5.90(2H,m), 6.70-7.70(45H,m), 8.85(1H,m), 9.15(1H,br s)

(B) 0.80 g (0.53 mmol) of the compound obtained in the above reaction (A) was dissolved in 8 ml of methylene chloride and 0.8 ml of anisole, and 11 ml of trifluoroacetic acid was added thereto at 0° C. The mixture was stirred at the same temperature for 2.5 hours. The reaction solution was concentrated under reduced pressure, and ethyl ether was added to the residue. The precipitates were collected by filtration and suspended in water. The suspension was adjusted to pH6.5 with a saturated sodium hydrogencarbonate aqueous solution, and insoluble substances were filtered off. The filtrate was subjected to reversed phase column chromatography (LC-Sorb RP-18, manufactured by Kemco Co.). The fraction (elution with a 3% methanol aqueous solution) containing the desired product was collected, concentrated and freeze-dried to obtain 70 mg (yield: 16.5%) of the above identified compound. MP: 180°) C. (decomposed)

IR(KBr)cm$^{-1}$: 1760, 1600, 1530, 1390, 1280

NMR(DMSO-d$_6$/D$_2$O)δ: 3.25-3.50(2H,m), 4.10-4.40(2H,m), 5.03(1H,m), 5.15(1H,s), 5.63(1H,m), 6.65-7.15(7H,m), 7.32(1H,s)

EXAMPLE 66

Preparation of disodium 7β-[2-(2-aminothiazol-4-yl)-2-(1-carboxylate-1-cyclopropoxyimino) acetamido]-3-[5-(3,4-dihydroxyphenyl)oxazol-2-yl]thiomethyl-3-cephem-4-carboxylate (syn-isomer)

A trifluoroacetate obtained by the same operation as in EXAMPLE 65 by using 0.65 g (0.68 mmol) of benzhydryl 7β-[2-(1-tert-butoxycarbonyl-1-cyclopropoxyimino)-2-(2-tritylaminothiazol-4-yl) acetamido]-3-chloromethyl-3-cephem-4-carboxylate (syn-isomer), 122 mg (0.81 mmol) of sodium iodide and 0.142 g (0.68 mmol) of 5-(3,4-dihydroxyphenyl)-2-mercaptooxazole, was suspended in water and adjusted to pH6.5 with a saturated sodium hydrogencarbonate aqueous solution. Insoluble substances were filtered off and the filtrate was subjected reversed phase column chromatography (LC Sorb RP-18, manufactured by Kemco Co.). The fraction (elution with a 3% methanol aqueous solution) containing the desired product was collected, concentrated and freeze-dried to obtain 22 mg (yield: 2.3%) of the above identified compound.

MP: 170°C. (decomposed)

IR(KBr)cm$^{-1}$: 1760, 1600, 1530, 1410

NMR(DMSO-d$_6$/D$_2$O)δ: 0.80-1.40(4H,m), 3.30-3.70(2H,m), 4.30(2H,br s), 5.02(1H,d,J=4.5Hz), 5.60(1H,d,J=4.5Hz), 6.70-7.15(4H,m), 7.33(1H,s)

EXAMPLE 67

Preparation of disodium 3-[5-(3,4-diacetoxyphenyl)-oxazol-2-yl]thiomethyl-7β-[2-(2-aminothiazol-4)-2-ethoxyiminoacetamido]-3-cephem-4-carboxylate isomer)

A trifluoroacetate obtained by the same operation as in EXAMPLE 26 by using 0.45 g (0.48 mmol) of benzhydryl 7β-[2-ethoxyimino-2-(2-tritylaminothiazol-4-yl) acetamido]-3-iodomethyl-3-cephem-4-carboxylate (syn-isomer), 0.1 g (0.48 mmol) of 5-(3,4-dihydroxyphenyl)-2-mercaptooxazole, 1.0 ml (1.06 mmol) of acetic anhydride and 0.86 ml (1.06 mmol) of pyridine, was suspended in water and adjusted to pH6.5 with a saturated sodium hydrogencarbonate aqueous solution. Insoluble substances were filtered off and the filtrate was subjected to reversed phase column chromatography (LC-Sorb RP-18, manufactured by Kemco Co.). The fraction (elution with a 40% methanol aqueous solution) containing the desired product was collected, concentrated and freeze-dried to obtain 23 mg (yield: 6.6%) the above identified compound.

MP: 190° C. (decomposed)

IR(KBr)cm$^{-1}$: 1760, 1670, 1610, 1530, 1500, 1370, 1210

NMR(DMSO-d$_6$D$_2$O)δ: 1.20(3H,t,J=6.0Hz), 2.30(6H,s), 3.35-3.65(2H,m), 4.13(2H,q,J=6.0Hz), 4.35(2H,br s), 5.02(1H,d,J=4.5Hz), 5.62(1H,d,J=4.5Hz), 6.75(1H,s), 7.30-7.70(4H,m)

EXAMPLE 68

Preparation of sodium 7β-[2-(2-aminothiazol-4-yl)-2-methoxyiminoacetamido]-3-(5, 6-dihydroxybenzimidazol-2-yl)thiomethyl-3-cephem-4-carboxylate (syn-isomer)

A trifluoroacetate obtained by the same operation as in EXAMPLE 1 by using 0.93 g (1.0 mmol) of benzhydryl 3-iodomethyl-7δ-[2-methoxyimino-2-(2-tritylaminothiazol-4-yl) acetamido]-3-cephem-4-carboxylate (syn-isomer) and 357 mg (1.0 mmol) of 2-mercapto-5,6-di(2-methoxyethoxymethoxy)benzimidazole, was suspended in water and adjusted to pH6.5 with a saturated sodium hydrogencarbonate aqueous solution. Insoluble substances were filtered off and the filtrate was subjected to ODS column chromatography (LC Sorb RP-18, manufactured by Kemco Co.). The fraction eluted with a 30% methanol aqueous solution was concentrated and freeze-dried to obtain 196 mg (yield: 33.8%) of the above identified compound.

MP: 170° C. (decomposed)

IR(KBr)cm$^{-1}$: 3400, 1770, 1675, 1640

NMR(DMSO-d$_6$)δ: 3.60–3.90(2H,m), 3.85(3H,s), 4.30(2H,br s), 5.15(1H,d,J=6Hz), 5.75(1H,m), 6.74(1H,s), 6.96(2H,s), 9.56(1H,br d,J=8Hz)

EXAMPLE 69

Preparation of
7β-[2-(2-aminothiazol-4-yl)-2-isopropoxyiminoacetamido]-3-(5,6-dihydroxy-2-methylbenzimidazol-2-yl)thiomethyl-3-cephem-4-carboxylic acid trifluoroacetate (syn-isomer)

The same operation as in EXAMPLE 32 by using 168 mg (0.18 mol) of benzhydryl 3-iodomethyl-7β-[2-methoxy-imino-2-(2-tritylaminothiazol-4-yl) acetamido]-3-cephem-4carboxylate (syn-isomer) and 67 mg (0.18 mmol) of 2-mercapto-5, 6-di(2-methoxyethoxymethoxy)-2-methylbenzimidazole, whereby 74 mg of the above identified compound was obtained.

MP: 180° C. (decomposed)

IR(KBr)cm$^{-1}$: 3400, 1775, 1675, 1635

NMR(DMSO-d$_6$)δ: 3.60(2H,m), 3.80(3H,s), 3.88(3H,s), 4.22(2H,m), 5.15(1H,d,J=5Hz), 5.78(1H,m), 6.78(1H,s), 7.02(2H,s)

EXAMPLE 70

Preparation of sodium
7β-[2-(2-aminothiazol-4-yl)-2-isopropoxyiminoacetamido]-3-(5,6,-dihydroxybenzimidazol-2-yl)thiomethyl-3-cephem-4-carboxylate (syn-isomer)

The trifluoroacetate obtained by the same operation as in EXAMPLE 1 by using 0.87 g (0.91 mmol) of benzhydryl 3-iodomethyl-7β-[2-isopropoxyimino-2-(2-tritylaminothiazol-4-yl) acetamido]-3-cephem-4-carboxylate (synisomer) and 357 mg (1.0 mmol) of 2-mercapto-5,6-di(2-methoxyethoxymethoxy) benzimidazole, was suspended in water and adjusted to pH6..5 with a saturated sodium hydrogen, carbonate aqueous solution. Insoluble substances were filtered off and the filtrate was subjected to ODS column chromatography (LC-Sorb RP-18, manufactured by Kemco Co.). The fraction (30% methanol aqueous solution) containing the desired product was concentrated under reduced pressure and freeze-dried, whereby 99 mg (yield: 25%) of the above identified compound was obtained.

MP: 150° C. (decomposed)

IR(KVBr)cm$^{-1}$: 3400, 1760, 1600

NMR(DMSO-d$_6$)δ: 1.17(6H,d,J=6Hz), 3.70(2H,m), 4.28(1H,m), 4.40-5.30(2H,m), 5.05(1H,d,J=6Hz), 5.60(1H,m), 6.61(1H,s), 6.70(2H,br s), 9.38(1H,m)

EXAMPLE 71

Preparation of sodium
7β-[2-(2-aminothiazol-4-yl)-2-allyloxyiminoacetamido]-3-(5,6-dihydroxybenzimidazol-2-yl)thiomethyl-3-cephem-4-carboxylate (syn-isomer)

The same operation as in EXAMPLE 1 was conducted by using 0.89 g (0.93 mmol) of benzhydryl 3-iodomethyl-7β-[2-allyloxyimino-2-(2-tritylaminothiazol-4-yl)acetamido]-3-cephem-4-carboxylate (syn-isomer) and 333 mg (0.93 mmol) of 2-mercapto-5,6-di(2-methoxyethoxymethoxy)benzimidazole, whereby 140 mg (yield: 25.8%) of the above identified compound was obtained.

MP: 165° C. (decomposed)

IR(KBr)cm$^{-1}$: 3280, 1760, 1600

NMR(DMSO-d$_6$)δ: 3.70(2H,m), 4,53(2H,br d,J=4Hz), 4.70–5.10(2H,m), 5.00–5.50(3H,m), 5.60(1H,m), 5.70–6.10(1H,m), 6.68(1H,s), 6.72(2H,br s), 7.15(2H,br s), 9.38(1H,br d)

EXAMPLE 72

Preparation of
7β-[2-(2-aminothiazol-4-yl)-2-(2-pyrrolidone-3-yl)oxyiminoacetamido]-3-(5,6-dihydroxybenzimidazol-2-yl)thiomethyl-3-cephem-4-carboxylic acid trifluoroacetate (syn-isomer)

The same operation as in EXAMPLE32 was conducted by using 0.90 g (0.90 mmol) of benzhydryl 3-iodomethyl-7β-[2-(2-pyrrolidone-3-yl) oxyimino-2-(2-tritylaminothiazol-4-yl-acetamido]-3-cephem-4-carboxylate (syn-isomer), whereby 155 mg (yield: 26.7%) of the above identified compound was obtained.

MP: 200°) C. (decomposed)

IR(KBr)cm$^{-1}$: 3400, 1775, 1630

NMR(DMSO-d$_6$)δ: 2.10–2.50(2H,m), 3.72(4H,m), 4.30(2H,br s), 4.70(1H,m), 5.18(1H,m), 5.80(1H,m), 6.80(1H,s), 6.98(2H,br s), 9.58(1H,m)

EXAMPLE 73

Preparation of
7β-[2-(2-aminothiazol-4-yl)-2-(1-carboxy-1-methylethoxyimino) acetamido]-3-(5,6-dihydroxybenzimidazol-2yl) thiomethyl-3cephem-4-carboxylic acid trifluoroacetate (syn-isomer)

The same operation as in EXAMPLE 32 was conducted by using 1.5 g (1.37 mmol) of benzhydryl 7β-[2-(1-benzhydryloxycarbonyl-1-methylethoxyimino)-2-(2-tritylaminothiazol-4-yl)acetamido]-3-iodomethyl-3-cephem-4carboxylate (syn-isomer) and 0.59 g (1.65 mmol) of 2-mercapto-5,6-di(2-methoxyethoxymethoxy)benzimidazole, whereby 519 mg (yield: 61.5%) of the above identified compound was obtained.

MP: 130° C. (decomposed)

IR(KBr)cm$^{-1}$: 3400, 1770, 1675, 1635

NMR(DMSO-d$_6$)δ: 1.46(6H,br s), 3.75(2H,m), 4.31(2H,m), 5.23(1H,d,J=5Hz), 5.82(1H,m), 6.78(1H,s), 6.99(2H,s), 9.45(1H,m)

EXAMPLE 74

Preparation of disodium
7β-[2-(2-aminothiazol-4-yl)-2-(1-carboxy-1-cyclopentyloxyimino)acetamido]-3-(5,6-dihydroxybenzimidazol-2-yl)thiomethyl-3-cephem-4-carboxylate (syn-isomer)

The same operation as in EXAMPLE 1 was conducted by using 1.1 g (0.91 mmol) of benzhydryl 7β-[2-(1-benzhydryloxycarbonyl-1-cyclopentyloxyimino)-2-(2-tritylaminothiazol-4-yl)acetamido]-3-iodomethyl-3-cephem-4carboxylate (syn-isomer) and 0.33 g (0.91 mmol) of 2-mercapto-5,6-di(2-methoxyethoxymethoxy)benzimidazole, whereby 77 mg (yield: 11.7%) of the above identified compound was obtained.

MP: 175°) C. (decomposed)

IR(KBr)cm$^{-1}$: 3425, 1760, 1600

NMR(DMSO-d$_6$)δ: 1.62(4H,m), 2.08(4H,m), 3.70(2H,m), 4.40–4.90(2H,m), 5.04(1H,d,J=5Hz), 5.69(1H,m), 6.70(1H,s), 6.76(2H,br s)

EXAMPLE 75

Preparation of sodium 7β-[2-(2-aminothiazol-4-yl)-2-methoxyiminoacetamido]-3-(5, 6-dihydroxybenzoxazol-2-yl)thiomethyl-3-cephem-4-carboxylate (syn-isomer)

The same operation as in EXAMPLE 1 was conducted by using 1.0 g (1.07 mmol) of benzhydryl 7β-[2-methoxyimino-2-(2-tritylaminothiazol-4-yl) acetamido]-3-iodomethyl-3-cephem-4-carboxylate (syn-isomer) and 380 mg (1.06 mmol) of 2-mercapto-5,6-di(2-methoxyethoxymethoxy)benzoxazole, whereby 106 mg (yield: 16.6%) of the above identified compound was obtained.

MP: 180° C. (decomposed)
IR(KBr)cm$^{-1}$: 3400, 1760, 1665, 1610
NMR(DMSO-d$_6$)δ: 3.72(2H,m), 3.80(3H,s), 4.35(2H,m), 4.96(1H,d,J=5Hz), 5.55(1H,m), 6.70(1H,s), 6.92(1H,s), 7.00(1H,s), 7.22(2H,m), 9.43(1H,br d,J=8Hz)

EXAMPLE 76

Preparation of disodium 7 β-[2-(2-aminothiazol-4-yl)-2-(1-carboxylate-1-methylethoxyimino) acetamido]-3-(5,6-dihydroxybenzoxazol-2-yl) thiomethyl-3-cephem-4-carboxylate (syn-isomer)

The filtrate obtained by the same operation as in EXAMPLE 1 by using 1.2 g (1.03 mmol) of benzhydryl 7β-[2-(1-benzhydryloxycarbonyl-1-methylethoxyimino)-2-(2-tritylaminothiazol-4-yl) acetamido]-3-iodomethyl-3-cephem-4-carboxylate (syn-isomer) and 0.37 g (1.03 mmol) of 2-mercapto-5,6-di(2-methoxyethoxymethoxy)benzoxazole, was subjected to ODS column chromatography and eluted with a 30% methanol aqueous solution, whereby 40 mg (yield; 5.06%) of the above identified compound was obtained.

MP: 185° C. (decomposed)
IR(KBr)cm$^{-1}$: 3400, 1770, 1630
NMR(DMSO-d6)δ: 1.42(6H,m), 3.70(2H,m), 4.00–4.60(2H,m), 5.06(1H,d,J=5Hz), 5.75(1H,m), 6.66(1H,s), 6.89(1H,s), 6.96(1H,s), 7.18(2H,br s), 9.40(1H,m)

REFERENCE EXAMPLE 1

Preparation of
7β-[2-(2-aminothiazol-4-yl)-2-methoxyiminoacetamido]-3-(5-phenyl-1,3,4-oxadiazol-2-yl)thiomethyl-3-cephem-4-carboxylic acid trifluoroacetate (syn-isomer)

The same operation as in EXAMPLE 1 was conducted by using 1.0 g (1.1 mmol) of benzhydryl 3-iodomethyl-7β-[2-methoxyimino-2-(2-tritylaminothiazol-4-yl)acetamido]-3-cephem-4-carboxylate (syn-isomer) and 0.19 mg (1.1 mmol) of 5-mercapto-2-phenyl-1,3,4-oxadiazole, whereby 225 mg (yield: 36.6%) of the above identified compound was obtained.

MP: 150°) C. (decomposed)
IR(KBr)cm$^{-1}$: 3380, 1780, 1675, 1635
NMR(DMSO-d$_6$)δ: 3.75(2H,m), 4.30(1H,br d,J=13Hz), 4.42(1H,br d,J=13Hz), 5.18(1H,d,J=5Hz), 5.78(1H,dd,J=5 and 8Hz), 6.86(1H,s), 7.27(1H,m), 7.60(2H,m), 7.96(2H,m), 9.70(1H,br d,J=8Hz)

REFERENCE EXAMPLE 2

Preparation of
7β-[2-(2-aminothiazol-4-yl)-2-methoxyiminoacetamido]-3-[5-(4-hydroxyphenyl)-1,3,4-trifluoroacetate (syn-isomer)

The same operation as in EXAMPLE 1 was conducted by using 1.0 g (1.1 mmol) of benzhydryl 3-iodomethyl-7β[2-methoxyimino-2-(2-tritylaminothiazol-4-yl)acetamido]-3-cephem-4-carboxylate (syn-isomer) and 0.21 mg (1.1 mmol) of 5-(4-hydroxyphenyl)-2-mercapto-1,3,4-oxadiazol-, whereby 444 mg (yield: 64.7%) of the above identified compound was obtained.

MP: 155° C. (decomposed)
IR(KBr)cm$^{-1}$: 3370, 1780, 1675, 1610
NMR(DMSO-d$_6$)δ: 3.72(2H,m), 4.36(2H,m). 5.20(1H,d,J=5Hz), 5.80(1H,m), 6.87(1H,s), 6.96(2H,d,J=9Hz), 7.80(2H,d,J=9Hz), 9.72(1H,br d,J=8Hz)

REFERENCE EXAMPLE 3

Preparation of disodium
7β-[2-(2-aminothiazol-4-yl)-2-(1-carboxylate-1-methylethoxyimino) acetamido]3-(5-phenyl-1,3,4-oxadiazol-2-yl) thiomethyl-3-cephem-4-carboxylate (syn-isomer)

The same operation as in EXAMPLE 1 was conducted by using 1.0 g (0.85 mmol) of benzhydryl 7β-[2-(1-benzhydryloxycarbonyl-1-methylethoxyimino)-2-(2-tritylaminothiazol-4-yl)acetamido]-3-iodomethyl-3-cephem-4carboxylate (syn-isomer) and 0.15 g (0.85 mmol) of 2-mercapto-5-phenyl-1,3,4-oxadiazole, whereby 195 mg (yield: 17.8%) of the above identified compound was obtained.

MP: 175° C. (decomposed)
IR(KBr)cm$^{-1}$: 3440, 1765, 1598
NMR(DMSO-d$_6$)δ: 1.40(3H,br s), 1.46(3H,br s), 3.60(2H,m), 4.42(2H,br s), 5.02(1H,d,J=5Hz), 5.68(1H,m), 6.71(1H,s), 7.18(1H,m), 7.60(2H,m), 7.95(2H,m)

REFERENCE EXAMPLE 4

Preparation of disodium
7β-[2-(2-aminothiazol-4-yl)-2-(1-carboxylate-1-methylethoxyimino) acetamido]-3-[5-(4-hydroxyphenyl)-1,3, 4-oxadiazol-2-yl]thiomethyl-3-cephem-4-carboxylate (syn-isomer)

The same operation as in EXAMPLE 1 was conducted by using 1.0 g (0.85 mmol) of benzhydryl 7β-2-(1-benzhydryloxycarbonyl-1-methylethoxyimino)-2-(2-tritylaminothiazol-4-yl)acetamido]-3-iodomethyl-3-cephem-4carboxylate (syn-isomer) and 0.16 g (0.85 mmol) of 5-(4-hydroxyphenyl)-2-mercapto-1,3,4-oxadiazole, whereby 84 mg (yield: 14%) of the above identified compound was obtained.

MP: 175° C. (decomposed)
IR(KBr)cm$^{-1}$: 3430, 1765, 1600
NMR(DMSO-d$_6$)δ: 1.40(3H,br s), 1.46(3H,br s), 3.50(2H,m), 4.38(2H,br s), 5.00(1H,d,J=5Hz), 5.68(1H,m), 6.71(1H,s), 6.88(2H,d,J=9Hz), 7.68(2H,d,J=9Hz)

REFERENCE EXAMPLE 5

Preparation of
7β-[2-(2-aminothiazol-4-yl)-2-methox-
yiminoacetamido]-3-( 5-phenyl-1,3,4-thiadiazol-2-yl)
thiomethyl-3-cephem-4-carboxylic acid trifluoroacetate
(syn-isomer)

The same operation as in EXAMPLE 32 was conducted by using 800 mg (0.86 mmol) of benzhydryl 3-iodomethyl-7β-[2-methoxyimino-2-( 2-tritylaminothiazol-4-yl)acetamido]-3-cephem-4-carboxylate (syn-isomer) and 167 mg (0.86 mmol) of 2-mercapto-5-phenyl-1,3,4-thiadiazole, whereby, 364 mg (yield: 71.2%) of the above identified compound was obtained.

MP: 165° C. (decomposed)
IR(KBr)cm$^{-1}$: 3400, 1780, 1675, 1630
NMR(DMSO-d$_6$)δ: 3.80(2H,m), 3.90(3H,s), 4.32(1H,d,J=12Hz), 4.63(1H,d,J=12Hz), 5.20(1H,d,J=5Hz), 5.82(1H,m), 6.86(1H,s), 7.60(3H,m), 7.95(2H,m), 9.72(1H,br d,J=8Hz)

REFERENCE EXAMPLE 6

Preparation of disodium
7β-[2-(2-aminothiazol-4-yl)-(1-carboxylate-1-methylethoxyimino)
acetamido]-3-(5-phenyl-1,3,4-thiadiazol-2-yl)
thiomethyl-3-cephem-4carboxylate (syn-isomer)

The same operation as in EXAMPLE 1 was conducted by using 800 mg (0.68 mmol) of benzhydryl 3-iodomethyl-7β-[2-( 1-benzhydryloxycarbonyl-1-methylethoxyimino)-2-(2-tritylaminothiazol-4-yl) acetamido]-3-cephem-4-carboxylate (syn-isomer) and 133 mg (0.68 mmol) of 2-mercapto-5phenyl-1,3,4-thiadiazole, whereby 171 mg (yield: 35%) of the above identified compound was obtained.

MP: 190°) C. (decomposed)
IR(KBr)cm$^{-1}$: 3430, 1765, 1600
NMR(DMSO-d$_6$)δ: 1.45(6H,br s), 3.80(2H,m), 4.20-4.80(2H,m), 5.06(1H,d,J=5Hz), 5.70(1H,m), 6.75(1H,s), 7.58(3H,m), 7.90(2H,m)

REFERENCE EXAMPLE 7

Preparation of
7β-[2-(2-aminothiazol-4-yl)-2methoxyiminoacetamido]-
3-[5-(4-hydroxyphenyl-1,3,4-thiadiazol-2-yl)
thiomethyl-3-cephem-4-carboxylic acid trifluoroacetate
(syn-isomer)

The same operation as in EXAMPLE 32 was conducted by using 800 mg (0.68 mmol) of benzhydryl 3-iodomethyl-7β-[2-methoxyimino-2-( 2-tritylaminothiazol-4-yl)acetamido]-3-cephem-4-carboxylate (syn-isomer) and 180 mg (0.85 mmol) of 5-(4-hydroxyphenyl)-2-mercapto-1,3,4-thiadiazole, whereby 276 mg (yield: 53%) of the above identified compound was obtained.

MP: 180°) C. (decomposed)
IR(KBr)cm$^{-1}$: 3400, 1780, 1675, 1630, 1600
NMR(DMSO-d$_6$)δ: 3.78(2H,m), 3.92(3H,s), 4.30(1H,d,J=14Hz), 4.60(1H,d,J=14Hz), 5.20(1H,d,J=5Hz), 5.80(1H,m), 6.88(1H,s), 6.92(2H,d,J=9Hz), 7.75(2H,d,J=9Hz)

REFERENCE EXAMPLE 8

Preparation of disodium
7β-[2-(2-aminothiazol-4-yl)-2-(1-carboxylate-1-
methylethoxyimino)
acetamido]-3-[5-(4-hydroxyphenyl)-1,3,4-thiadiazol-2-
yl)thiomethyl-3-cephem-4-carboxylate (syn-isomer)

The same operation as in EXAMPLE 1 was conducted by using 800 mg (0.68 mmol) of benzhydryl 3-iodomethyl-7 β-8 2-( 1-benzhydryloxycarbonyl-1-methylethoxyimino)-2-(2-tritylaminothiazol-4-yl) acetamido]-3-cephem-4-carboxylate (syn-isomer) and 200 mg (0.95 mmol) of 5-(4-hydroxyphenyl)-2-mercapto-1,3,4-thiadiazole, whereby 218 mg (yield: 44%) of the above identified compound was obtained.

MP: 195° C. (decomposed)
IR(KBr)cm$^{-1}$: 3400, 1760, 1600
NMR(DMSO-d$_6$)δ: 3.80(2H,m), 4.20-4.-90(2H,m), 5.08(1H,d,J=5Hz), 5.78(1H,m), 6.76(1H,s), 6.96(1H,d,J=9Hz), 7.70(2H,d,J=9Hz)

REFERENCE EXAMPLE 9

Preparation of sodium 7μ-[2-(2-aminothiazol-4-yl)-2-methoxyiminoacetamido]-3-( 4-phenylthiazol-2-yl)-thiomethyl-3-cephem-4-carboxylate (syn-isomer)

The same operation as in EXAMPLE 1 was conducted by using 1.0 g (1.1 mmol) of benzhydryl 3-iodomethyl-7β-[2-methoxyimino-2-( 2-tritylaminothiazol-4-yl)acetamido]3-cephem-4-carboxylate (syn-isomer) and 0.31 g (1.0 mmol) of 2-mercapto-4-phenylthiazole, whereby 117 mg (yield: 6.45%) of the above identified compound was obtained.

MP: 175° C. (decomposed)
IR(KBr)cm$^{-1}$: 3420, 1764, 1620
NMR(DMSO-d$_6$)δ: 3.57(2H,m), 3.86(3H,s), 4.48(1H,d,J=12Hz), 4.60(1H,d,J=12Hz), 5.04(1H,d,J=5Hz), 5.60(1H,dd,J=5 and 8Hz), 6.73(1H,s), 7.21(2H,br s), 7.38(3H,m), 7.95(1H,m), 7.99(1H,s), 9.50(1H,br d,J=8Hz)

REFERENCE EXAMPLE 10

Preparation of sodium
7β-[2-(2-aminothiazol-4-yl)-2-methox-
yiminoacetamido]-3-[4-(
4-hydroxyphenyl)thiazol-2-yl]thiomethyl-3-cephem-4-
carboxylate (syn-isomer)

The same operation as in EXAMPLE 1 was conducted by using 1.0 g (1.1 mmol) of benzhydryl 3-iodomethyl-7β- [2-methoxyimino-2-( 2-tritylaminothiazol-4-yl)acetamido]-3-cephem-4-carboxylate (syn-isomer) and 0.30 g (1.4 mmol) of 2-mercapto-4-(4-hydroxyphenyl)thiazole, whereby 205 mg (yield: 30.3%) of the above identified compound was obtained.

MP: 185° C. (decomposed)
IR(KBr)cm$^{-1}$: 1 3420, 1762, 1607
NMR(DMSO-d$_6$)δ: 3.56(2H,m), 4.47(1H,d,J=12Hz), 4.63(1H,d,J=12Hz), 5.08(1H,d,J=5Hz), 5.65(1H,dd,J=5 and 8Hz), 6.79(1H,s), 6.90(1H,d,J=8Hz), 7.26(2H,br s), 7.72(1H,s),

REFERENCE EXAMPLE 11

Preparation of disodium
7β-[2-(2-aminothiazol-4-yl)-2-(1-carboxylate-1-methylethoxyimino)
acetamido]-3-(4-phenylthiazol-2-yl)
thiomethyl-3-cephem-4-carboxylate (syn-isomer)

The same operation as in EXAMPLE 1 was conducted by using 1.2 g (1.0 mmol) of benzhydryl 7β-[2-(1-benzhydryloxycarbonyl-1-methylethoxyimino)-2-(2-tritylaminothiazol-4-yl) acetamido]-3-iodomethyl-3-cephem-4-carboxylate (synisomer) and 0.30 g (1.5 mmol) of 2-mercapto-4-phenylthiazole, whereby 170 mg (yield: 17%) of the above identified compound was obtained.
MP: 180° C. (decomposed)
IR(KBr)cm$^{-1}$: 3430, 1765, 1595
NMR(DMSO-d$_6$)δ: 1.42(3H,br s), 1.50(3H,br s), 3.55(2H,m), 4.37(1H,br d,J=13Hz), 4.62(1H,br d,J=13Hz), 5.03(1H,d,J=5Hz), 5 5.70(1H,m), 6.71(1H,s), 7.20(2H,br s), 7.39(3H,m), 7.95(1H,d,J=8Hz), 8.00(1H,s)

REFERENCE EXAMPLE 12

Preparation of disodium
7β-[2-(2-aminothiazol-4-yl)-2-(1-carboxylate-1-methylethoxyimino)
acetamido]-3-[4-(4-hydroxyphenyl)thiazol-2-yl]thiomethyl-3-cephem-4-carboxylate (syn-isomer)

The same operation as in EXAMPLE 1 was conducted by using 1.0 g (0.85 mmol) of benzhydryl 7β-[2-(1-benzhydryloxycarbonyl-1-methylethoxyimino)-2-(2-tritylaminothiazol-4-yl)acetamido]-3-iodomethyl-3-cephem-4-carboxylate (syn-isomer) and 0.27 g (1.3 mmol) of 4-(4-hydroxyphenyl)2-mercaptothiazole, whereby 30 mg (yield: 5.35%) of the above identified compound was obtained.
MP: 170° C. (decomposed)
IR(KBr)cm$^{-1}$: 3440, 1762, 1596
NMR(DMSO-d$_6$)δ: 1.43(3H,br s), 1.50(3H,br s), 3.60(2H,m), 4.36(1H,br d,J=12Hz), 4.60(1H,d,J=12Hz), 5.03(1H,d,J=5Hz), 5.70(1H,m), 6.73(1H,s), 6.86(1H,d,J=8Hz), 7.20(2H,br s), 7.69(1H,s), 7.72(1H,d,J=8Hz)

REFERENCE EXAMPLE 13

Preparation of
7β-[2-(2-aminothiazol-4-yl)-2-methoxyiminoacetamido)-3-[4-(3,4-dihydroxyphenyl)-thiazol-2-yl]thiomethyl-3-cephem-4-carboxylate trifluoroacetate (syn-isomer)

The same operation as in EXAMPLE 32 was conducted by using 1.0 g (1.1 mmol) of benzhydryl 3-iodomethyl-7β-[2-methoxyimino-2-( 2-tritylaminothiazol-4-)acetamido]-3-cephem-4-carboxylate (syn-isomer) and 0.27 g (1.1 mmol) of 4-(3-,4-dimethoxyphenyl-)-2-mercaptothiazole, whereby 262 mg-(yield: 62.3%) of the above identified compound was obtained.
MP: 135°) C. (decomposed)
IR(KBr)cm$^{-1}$: 3370, 1780, 1675
NMR(DMSO-d$_6$)δ: 3.80(2H,m), 3.82(3H,s), 3.88(3H,s), 3.93(3H,s), 4.28(1H,d,J=12Hz), 4.58(1H,d,J=12Hz), 5.20(1H,d,J=5Hz), 5.80(1H,dd,J=5 and 8Hz), 6.88(1H,s), 7.30(1H,d,J=6Hz), 7.50(1H,br s), 7.52(1H,br d,J=6Hz), 8.95(1H,s), 9.70(1H,br d,J=8Hz)

REFERENCE EXAMPLE 14

Preparation of trisodium
7β-[2-(2-aminothiazol-4-yl)-2-(1-carboxylate-1-methylethoxyimino)
acetamido]-3-[4-carboxylate-5-phenyl)
thiazol-2-yl]thiomethyl-3-cephem-4-carboxylate
(syn-isomer)

The same operation as in EXAMPLE 50 was conducted by using 1.08 g (1.0 mmol) of benzhydryl 7β-[2-(1-benzhydryloxycarbonyl-1-methylethoxyimino)-2-(2-tritylaminothiazol-4-yl)acetamido]-3-chloromethyl-3-cephem-4carboxylate (syn-isomer) and 237 mg (1.0 mmol) of 4-carboxy-5-phenyl-2-mercaptothiazole, whereby 212 mg (yield: 27.4%) of the above identified compound was obtained.
MP: 230° C. (decomposed)
IR(KBr)cm$^{-1}$: 1760, 1660, 1595, 1535, 1405, 1370
NMR(D$_2$O)δ: 1.52(6H,s), 3.61(2H,ABq), 4.23(2H,ABq), 5.18(1H,d,J=4.5Hz), 5.86(1H,d,J=4.5Hz), 6.96(1H,s), 7.47(5H,s)

REFERENCE EXAMPLE 15

Preparation of disodium
7β-[2-(2-aminothiazol-4-yl)-2-methoxyiminoacetamido]-3-(5-carboxylatemethyl-4-phenylthiazol-2-yl)thiomethyl-3-cephem-4-carboxylate (syn-siomer)

The same operation as in EXAMPLE 1 was conducted by using 1.0.g (1.07 mmol) of benzhydryl 3-iodomethyl-7β-[2-methoxyimino-2-( 2-tritylaminothiazol-4-yl)acetamido]-3-cephem-4 carboxylate (syn-isomer) and 0.45 g (1.08 mmol) of 5-(benzhydryloxycarbonylmethyl-2-mercapto-4phenylthiazole, whereby 276 mg (yield: 37%) of the above identified compound was obtained.
MP: 195-200°) C. (decomposed)
IR(KBr)cm$^1$: 3420, 1760, 1600, 1530, 1380
NMR(DMSO-d$_6$)δ: 3.92(3H,s), 4.32(1H,d,J=12.0Hz), 4.78(1H,d,J=12.0Hz), 5.10(1H,d,J=5.0Hz), 5.68(1H,m), 6.80(1H,s), 7.30-7.80(5H,m), 9.60(1H,br d,J=6.0Hz)

REFERENCE EXAMPLE 16

Preparation of trisodium
7β-[2-(2-aminothiazol-4-yl)-2-(1-carboxylate-1-methylethoxyimino)
acetamido]-3-(5-carboxylatemethyl-4-phenylthiazol-2-yl)thio-methyl-3-cephem-4-carboxylate (syn-isomer)
The same operation as in EXAMPLE 1 was conducted
by using 1.2 g (1.03 mol) of benzhydryl
7β-[2-(1-benzhydryloxycarbonyl-1-methylethoxyimino)-2-( 2-tritylaminothiazol-4-yl)
acetamido]-3-iodomethyl-3-cephem-4-carboxylate
(synisomer) and 0.43 g (1.04 mmol) of
5-benzhydryloxycarbonylmethyl-2-mercapto-4-phenyl-thiazole, whereby 178 mg (yield: 22%) of the above identified compound was obtained.

MP: 180° C. (decomposed).
IR(KBr)cm$^{-1}$: 3420, 1760, 1590, 1535, 1400
NMR(DMSO-d$_6$)δ: 1.40(3H,br s), 1.48(3H,br s), 4.10–4.70(2H,m), 5.10(1H,m), 5.68(1H,m), 6.72(1H,s), 7.30-7.80(5H,m)

REFERENCE EXAMPLE 17

Preparation of disodium 7β-[2-(2-aminothiazol-4-yl)-2-methoxyminoacetamido]-3-[5-carboxylatemethyl-4-(4-hydroxyphenyl)thiazol-2-yl]thiomethyl-3-cephem-4-carboxylate (syn-isomer)

The same operation as in EXAMPLE 1 was conducted by using 450 mg (0.48 mmol) of benzhydryl 3-iodomethyl-7β-[2-methoxyimino-2-( 2-tritylaminothiazol-4-yl)acetamido]-3-cephem-4-carboxylate (syn-isomer) and 250 mg (0.48 mmol) of 5-benzhydryloxycarbonylmethyl-4-[4-(2-methoxyethoxymethoxy)-phenyl]-2-mercaptothiazole, whereby 105 mg (yield: 31%) of the above identified compound was obtained.

MP: 200–205°) C. (decomposed)

IR(KBr)cm$^{-1}$: 3420, 1760, 1590, 1535, 1385

NMR(DMSO-d$_6$)δ: 3.85(3H,s), 4.25(1H,d,J=12.0Hz), 4.62(1H,d,J=12.0Hz), 5.00(1H,d,J=5.0Hz), 5.60(1H,m), 6.72(1H,s), 6.80(2H,d,J=8.0Hz), 7.46(2H,d,J=8.0Hz), 9.55(1H,m)

REFERENCE EXAMPLE 18

Preparation of disodium 3-[4-(4-acetoxyphenyl)-5-carboxylatemethylthiazol-2-yl]thiomethyl-7δ-[2-(2-aminothiazol-4-yl)-2-methoxyiminoacetamido]-3-cephem-4-carboxylate (syn-isomer)

The same operation as in EXAMPLE 1 was conducted by using 1.0 g (1.07 mmol) of benzhydryl 3-iodomethyl-7β-[2-methoxyimino-2-( 2-tritylaminothiazol-4-yl)acetamido]-3-cephem-4-carboxylate (syn-isomer) and 0.51 g (1.07 mmol) of 4-(4-acetoxyphenyl)-5-benzhydryloxycarbonylmethyl-2-mercaptothiazole, whereby 202 mg (yield: 25%) of the above identified compound was obtained.

MP: 180°–185° C. (decomposed)

IR(KBr)cm$^{-1}$: 3420, 1760, 1600, 1535, 1380

NMR(DMSO-d$_6$)δ: 2.30(6H,s), 3.83(3H,s), 4.10-4.48(2H,m), 5.02(1H,d,J=5.0Hz), 5.60(1H,m), 6.78(1H,s), 7.18(1H,d,J=8.0Hz), 7.78(1H,d,J=8.0Hz)

REFERENCE EXAMPLE 19

Preparation of trisodium 7β-[2-2-aminothiazol-4yl)-2-(1-carboxylate-1-methylethoxyimino) acetamido]-3-[5-carboxylatemethyl-4-(4-hydroxyphenyl) thiazol-2-yl]thiomethyl-3-cephem-4-carboxylate (syn-isomer)

The same operation as in EXAMPLE 1 was conducted by using 584 mg (0.50 mmol) of benzhydryl 7β-[2-(1-benzhydryloxycarbonyl-1-methylethoxyimino)-2-( 2-tritylaminothiazol-4-yl)acetamido]-3-iodomethyl-3-cephem-4carboxylate (syn-isomer) and 250 mg (0.48 mmol) of 5-benzhydryloxycarbonylmethyl-2-mercapto-4-[4-(2-methoxyethoxymethoxy)phenyl]-thiazole, whereby 104 mg (yield: 26%) of the above identified compound was obtained.

MP: 170°–175° C.

IR(KBr)cm$^{-1}$: 3400, 1760, 1585, 1535, 1400,

NMR(DMSO-d$_6$)δ: 1.42(3H,br s), 1.46(3H,br s), 4.10–4.70(2H,m), 5.00(1H,d,J=5.0Hz), 5.66(1H,d,J=5.0Hz), 6.75(1H,s), 6.86(2H,d,J=8.0Hz), 7.48(2H,d,J=8.0Hz)

REFERENCE EXAMPLE 20

Preparation of trisodium 3-[4-(4-acetoxyphenyl)-5-carboxylatemethylthiazol-2-yl]thiomethyl-7β-[2-(2-aminothiazol-4-yl)-2-(1-carboxylate-1-methylethoxyimino) acetamido]-3-cephem-4-carboxylate (syn-isomer)

The same operation as in EXAMPLE 1 was conducted by using 1.2 g (1.03 mmol) of benzhydryl 7β-[2-(1-benzhydryloxycarbonyl-1-methylethoxyimino)-2-( 2-tritylaminothiazol-4-yl)acetamido]-3-iodomethyl-3-cephem-4-carboxylate (syn-isomer) and 0.49 g (0.49 mmol) of 4-(4-acetoxyphenyl)-5-benzhydryloxycarbonylmethyl-2mercaptothiazole, whereby 247 mg (yield: 29%) of the above identified compound was obtained.

MP: 180°–185° C. (decomposed)

IR(KBr)cm$^{-1}$: 3420, 1760, 1590, 1535, 1400, 1370

NMR(DMSO-d$_6$)δ: 1.44(3H,br s), 1.48(3H,br s), 2.32(6H,s), 4.10–4.48(2H,m), 5.02(1H,m), 5.68(1H,m), 6.80–7.80(5H,m)

REFERENCE EXAMPLE 21

Preparation of sodium 7β-[2-(2-aminothiazol-4-yl)-2methoxyiminoacetamido]-3-( 5-phenyloxazol-2-yl)thiomethyl-3-cephem-4-carboxylate (syn-isomer)

The same operation as in EXAMPLE 65 was conducted by using 600 mg (0.71 mmol) of benzhydryl 3-chloromethyl-7β-[2-methoxyimino-2-( 2-tritylaminothiazol-4-yl)acetamido]-3-cephem-4-carboxylate (syn-isomer), 160 mg (1.07 mmol) of sodium iodide and 130 mg (0.72 mmol) of 2-mercapto-5-phenyloxazole, whereby 70 mg (yield: 7.1%) of the above identified compound was obtained.

MP: 180° C. (decomposed)

IR(KBr)cm$^{-1}$: 1760, 1610, 1530, 1390, 1350, 1040

NMR(DMSO-d$_6$/D$_2$O)δ: 3.40–3.65(2H,m), 3.83(3H,s), 4.32(2H,m), 5.03(1H,d,J=4.5Hz), 5.63(1H,d,J=4.5Hz), 6.80(1H,s), 7.30–7.75(6H,m)

REFERENCE EXAMPLE 22

Preparation of disodium 7β-[2-(2-aminothiazol-4-yl)-2-(1-carboxylate-1-methylethoxyimino) acetamido]-3(5-phenyloxazol-2-yl)thiomethyl-3-cephem-4-carboxylate (syn-isomer)

The same operation as in EXAMPLE$^{65}$ was conducted by using 850 mg (0.72 mmol) of benzhydryl 7β-[2-(1-benzhydryloxycarbonyl-1-methylethoxyimino)-2-( 2-tritylaminothiazol-4-yl)acetamido]-3-iodomethyl-3-cephem-4-carboxylate (syn-siomer) and 130 mg (0.72 mmol) of 2-mercapto -5-phenyloxazole, whereby 70 mg (yield: 15.7%) of the above identified compound was obtained.

MP: 180° C. (decomposed)

IR(KBr)cm$^{-1}$: 1760, 1600, 1530, 1470, 1400, 1360, 1160, 760

NMR(DMSO-d$_6$/D$_2$O)δ: 1.43(6H,m), 3.30–3.70(2H,m), 4,37(2H,m), 5.03(1H,d,J=4.5Hz), 5.65(1H,d,J=4.5Hz), 6.75(1H,s), 7.25–7.80(6H,m)

REFERENCE EXAMPLE 23

Preparation of sodium
7β-[2-(2-aminothiazol-4-yl)-2-methoxyiminoacetamido]-3-[5-(4-hydroxyphenyl)-oxazol-2-yl]thiomethyl-3-cephem-4-carboxylate (syn-isomer)

The same operation as in EXAMPLE 65 was conducted by using 840 mg (1.0 mmol) of benzhydryl 3-chloromethyl-7β-[2-methoxyimino-2-(2-tritylaminothiazol-4-yl)acetamido]-3-cephem-4-carboxylate (syn-isomer), 225 mg (1.5 mmol) of sodium iodide and 193 mg (1.0 mmol) of 5-(4-hydroxyphenyl)-2mercaptooxazole, whereby 55 mg (yield: 9.0%) of the above identified compound was obtained.

MP: 195° C. (decomposed)
IR(KBr)cm$^{-1}$: 1760, 1620, 1530, 1500, 1040
NMR(DMSO-d$_6$D$_2$O)δ: 3.30–3.70(2H,m), 3.83(3H,s), 4.32(2H,br s), 5.01(1H,d,J=4.5Hz), 5.63(1H,d,J=4.5Hz), 6.78(1H,s), 6.88(2H,d,J=9.0Hz), 7.40(1H,s), 7.50(2H,d,J=9.0Hz)

REFERENCE EXAMPLE 24

Preparation of disodium
7β-[2-(2-aminothiazol-4-yl)-2-(1-carboxylate-1-methylethoxyimino)acetamido]-3-[5-(4-hydroxyphenyl)oxazol-2-yl]thiomethyl-3-cephem-4-carboxylate (syn-isomer)

The same operation as in EXAMPLE 1 was conducted by using 1.0 g (0.85 mmol) of benzhydryl 7β-[2-(1-benzhydryloxycarbonyl-1-methylethoxyimino)-2-(2-tritylaminothiazol-4-yl)acetamido]-3-iodomethyl-3-cephem-4-carboxylate (syn-isomer) and 173 mg (0.89 mmol) of 5-(4-hydroxyphenyl)-2-mercaptooxazole, whereby 39 mg (yield: 7.3%) of the above identified compound was obtained.

MP: 190° C. (decomposed)
IR(KBr)cm$^{-1}$: 1760, 1620, 1530, 1500, 1400, 1360
NMR(DMSO-d6/D$_2$O)δ: 1.40(6H,br s), 3.35–3.60(2H,m), 4.25–4.55(2H,m), 5.00(1H,d,J=4.5Hz), 5.63(1H,m), 6.65–7.00(3H,m), 7.20–7.55(3H,m)

REFERENCE EXAMPLE 25

Preparation of
2-mercapto-5-[3,4-di(2-methoxyethoxymethoxy)phenyl]-1,3,4-oxadiazole (A) 2.5 g (14.9 mmol) of methyl protocatechuate was suspended in 50 ml of methylene chloride at 0° C., and 7.84 ml (45 mmol) of ethyldiisopropylamine was added thereto to obtain a uniform solution. 5.8 ml (45 mmol) of 2-methoxyethoxymethyl chloride was dropwise added and stirred for 30 minutes. The reaction solution was washed sequentially with water, 0.5 N sodium hydroxide aqueous solution and a saturated sodium chloride aqueous solution, and the water layer was extracted twice with methylene chloride. The organic layers were put together and dried over anhydrous sodium sulfate. The solvent was distilled off under reduced pressure to obtain 5.1 g (yield: 99%) of methyl 3,4-di(2-methoxyethoxymethoxy)benzoate.

NMR(CDCl$_3$)δ: 3.32(3H,s), 3.34(3H,s), 3.55(4H,m), 3.83(4H,m), 3,86(3H,s), 5.32(4H,m), 7.18(1H,d,J=9Hz), 7.67(1H,dd,J=2 and 9Hz), 7.79(1H,d,J=2Hz)

(B) 5.1 g (15 mmol) of the compound obtained in the above reaction (A) was dissolved in 100 mg of methanol, and 40 ml (300 mmol) of a 80% hydrazine hydrate was added. The mixture was heated under reflux, and 40 ml of a 80% hydrazine hydrate was further added. The mixture was heated under reflux for 2 hours again. The reaction solution was cooled, poured into water and extracted three times with ethyl acetate. The extract was washed with a saturated sodium chloride aqueous solution and dried over anhydrous sodium sulfate. The solvent was distilled off under reduced pressure to obtain 4.2 g of a crude product of 3,4-di(2-methoxyethoxymethoxy)benzohydrazide.

(C) To 42 ml of an ethanol solution containing 1.27 g (18 mmol) of a 80% potassium hydroxide(i.e. an aqueous solution comprising 1.0 g of potassium hydroxide and 0.27 ml of water), 4.2 g (12 mmol) of the compound obtained in the above reaction (B) and 3.64 ml (61 mmol) of carbon disulfide were added and heated for 1 hour under reflux. The solvent was distilled off under reduced pressure, and the residue was dissolved in water. The solution was adjusted to pH1.5 with 1N hydrochloric acid and extracted three times with ethyl acetate. The organic layer was washed with a saturated sodium chloride aqueous solution and dried over anhydrous sodium sulfate. The solvent was distilled off under reduced pressure and the residue was subjected to silica gel column chromatography (Wakogel C-300, ethyl acetate:hexane =3:1) to obtain 3.03 g (yield: 52.3%) of the above identified compound.

MP: 84°) C.
IR(KBr)cm$^{-1}$: 1620, 1585, 1520, 1500, 1360, 1250, 1105, 1090, 995
NMR(DMSO-d$_6$)δ: 3.27(6H,s), 3.51(4H,m), 3.80(4H,m), 5.38(2H,s), 5.39(2H,s), 7.32(1H,d,J=6.0Hz), 7.54(1H,dd,J=1.8 and 6.0Hz), 7.62(1H,d,J=1.8Hz)
Elemental analysis: as $C_{16}H_{22}N_2O_7S$ Calculated (%): C,49.73 ; H,5.74 ; N,7.25 ; S,8.30, Found (%) : C,49.66 ; H,5.85 ; N,7.10 ; S,8.24

REFERENCE EXAMPLE 26

Preparation of
7β-amino-3-[5-(3,4-dihydroxyphenyl)-1,3,4-oxadiazol-2-yl]thiomethyl-3-cephem-4-carboxylic acid (A) 19.8 g (0.353 mol) of potassium hydroxide was dissolved in 5.1 ml of water and 830 ml of ethanol, and 39.6 g (0.236 mol) of 3,4-dihydroxybenzohydrazide and 99 ml (1.65 mol) of carbon disulfide was added thereto. The mixture was heated for 24 hours under reflux. The reaction solution was stirred for 1.5 hours under cooling with ice. The precipitated crystals were collected by filtration and washed with 200 ml of ethanol. The crystals were dissolved in 3 liter of water and adjusted to pH1.5 with 6N hydrochloric acid under cooling with ice. The solution was extracted with 1 liter of ethyl acetate and 400 ml of ethyl acetate. The organic layers were put together, washed twice with 300 ml of a saturated sodium chloride aqueous solution, dried over anhydrous magnesium sulfate and concentrated under reduced pressure to obtain 42.8 g (yield: 86.5%) of 2-mercapto-5-(3,4-dihydroxyphenyl)-1,3,4-oxadiazole.

MP: 225-230° C. (decomposed)
IR(KBr)cm$^{-1}$: 1625, 1595, 1510, 1495, 1475, 1365, 1340, 1290, 1225, 1175, 1125, 710
NMR(DMSO-d$_6$)δ: 6.92(1H,d,J=9Hz), 7.24(1H,d,J=9Hz), 7.28(1H,s), 9.53(1H,br s), 9.80(1H,br s), 14.40(1H,br s)

(B) To 520 ml of acetonitrile 16.3 g (60 mmol) of 7β-aminocephalosporanic acid and 13.9 g (66 mmol) of 2-mercapto-5-(3,4-dihydroxyphenyl)-1,3,4-oxadiazole and 45.4 ml (360 mmol) of boron trifluoride diethyl etherate were added, and stirred at 50° C. for 3 hours. The reaction solution was cooled and poured into 450 ml of cold water. The mixture was stirred at room temperature for 1 hour and adjusted to pH2.0 with a 25% aqueous ammonia. The mixture was stirred at not more than 5° C. for 1 hour, and the precipitates were collected by filtration. The precipitates were washed with water and ethyl acetate and dried to obtain 21.3 g (yield: 84.1%) of the above identified compound.

MP: 188–193° C. (decomposed)

IR(KBr)cm$^{-1}$: 1805, 1620, 1520, 1485, 1415, 1350, 1290, 1190, 1120

NMR(DMSO-d$_6$)δ: 3.68(2H,ABq), 4.31(2H,ABq), 4.78(1H,d,J=4.5Hz), 4.98(1H,d,J=4.5Hz), 6.89(1H,d,J=9.0Hz), 7.27(1H,d,J=9.0Hz), 7.33(1H,s)

REFERENCE EXAMPLE 27

Preparation of 2-[α-benzhydryloxycarbonyl-3,4-di(2-(methoxyethoxyethoxy) benzyloxyimino]-2-(2-tritylaminothiazol-4-yl)acetic acid (syn-isomer)

(A) 500 ml of an aqueous solution containing 48 g (1.2 mol) of sodium hydroxide was dropwise added to a suspension of 88 g (0.8 mol) of catechol and 109.5 g (about 0.5 mol) of a 40% glyoxylic acid aqueous solution under a nitrogen atmosphere under cooling with ice, and heated to 40° C. for 5 hours. The reaction solution was adjusted to pH2.0 with 6N hydrochloric acid under cooling with ice, and unreacted catechol was extracted with ethyl acetate. The water layer was evaporated to dryness under reduced pressure. The residue was dissolved in 700 ml of N,N-dimethylformamide and 276 g (2 mol) of pottasium carbonate, 10 g (60 mmol) of pottasium iodide and 230 ml (2 mol) of benzylchloride were added thereto. The mixture was stirred for 15 hours at room temperature and further stirred for 8 hours at 40° C. The reaction solution was poured into 1.5 liter of ice water and extracted with ethyl acetate, followed by washing with water and a saturated sodium chloride aqueous solution. The extract was dried over anhydrous sodium sulfate and concentrated under reduced pressure to obtain crude benzyl 3,4-dibenzyloxymandelate. 1 liter of methanol and 200 ml of an aqueous solution containing 60 g of sodium hydroxide were added to the residue and stirred for 5 hours at room temperature. The reaction solution was concentrated under reduced pressure, and 1 liter of ice water was added to the residue. The solution was adjusted to pH2.0 with concentrated hydrochloric acid and extracted with ethyl acetate. The extract was dried over anhydrous sodium sulfate and concentrated under reduced pressure. After cooling, the precipitated crystals were collected and washed with isopropyl ether to obtain 83 g (yield: 45.5%) of 3,4-dibenzyloxymandelic acid.

IR(KBr)cm$^{-1}$: 3500, 1705, 1520, 1425, 1270, 1235, 1140, 1095, 1030, 735

NMR(DMSO-d$_6$)δ: 4.95(1H,s), 5.10(4H,s), 6.99(2H,s), 7.17(1H,s), 7.40(10H,br s)

(B) 2.00 g (5.49 mmol) of the compound obtained in the above reaction (A) was dissolved in 20 ml of tetrahydrofuran at room temperature, and 0.50 g of a 10% palladium carbon catalyst was added thereto and subjected to catalytic hydrogenation for 1.5 hours. The catalyst was filtered off and 1.20 g (6.1 mmol) of diphenydiazomethane was added to the filtrate and the mixture was stirred for 12 hours at room temperature. The solvent was distilled off under reduced pressure and the residue was dissolved in ethyl acetate, followed by washing with a 5% of sodium hydrogencarbonate aqueous solution. The organic layer was dried over anhydrous sodium sulfate, and the solvent was distilled off under reduced pressure to obtain 1.38 g (yield : 76%) of crude benzhydryl 3,4-dihydroxymandelate, which was used to the next reaction without purification.

NMR(DMSO-d$_6$)δ: 5.09(1H,d,J=4Hz), 5.86(1H,d,J=4Hz), 6.60–6.90(3H,m), 6.76(1H,s), 7.00–7.60(10H, m)

(C) 6.9 g (about 19.7 mmol) of the compound obtained in the above reaction (B) was dissolved in 140 ml of methylene chloride and 13.8 ml (79 mmol) of diisopropylethyl amine was added thereto and cooled to 0° C. 8.9 ml (79 mmol) of 2-methoxyethoxymethyl chloride was dropwise added thereto, and the mixture was stirred for 1 hour. The reaction solution was washed sequentially with 1N hydrochloric acid, 1N sodium hydroxide aqueous solution and a saturated sodium chloride aqueous solution, and dried over anhydrous sodium sulfate. The solvent was distilled under reduced pressure, and the residue was subjected to silica gel column chromatography (Wakogel C-300). The fractions containing the desired compound (ethyl acetate:hexane =2:1) were concentrated to obtain 6.0 g (yield: 58%) of benzhydryl 3,4-di(2-methoxyethoxymethoxy)mandelate.

NMR(DMSO-d$_6$)δ: 3.22(6H,s), 3.45(4H,m), 3.75 (4H,m), 5.18(2H,s), 5.22(2H,s), 5.25(1H,d,J=5Hz), 6.22(1H,d,J=5Hz), 6.78(1H, s), 6.90≧7.60(13H, m)

(D) 5.0 g (9.5 mmol) of the compound obtained in the above reaction (C) was dissolved in 100 ml of methylene chloride and 4.35 ml of (55.0 mmol) of pyridine was added thereto. Then, a solution comprising 1.2 ml (16.5 mmol) of thionyl chloride and 12 ml of methylene chloride was dropwise added at 0° C. and the mixture was stirred for 30 minutes. The reaction solution was poured into a 10% sodium hydrogencarbonate aqueous solution, and extracted with methylene chloride. The organic layer was dried over anhydrous sodium sulfate, and the solvent was distilled off under reduced pressure. The residue was subjected to silica gel column chromatography (Wakogel C-300), and the fractions containing the desired compound (ethyl acetate:hexane =1:1) was concentrated to obtain 3.35 g (yield: 65%) of benzhydryl 2-chloro-2-[3,4-di(2methoxyethoxymethoxy)phenyl]acetate, which was used for the next reaction immediately.

(E) 9.0 g (16.5 mmol) of the compound obtained in the above reaction (D) was dissolved in 90 ml of N,N-dimethylformamide. A solution of 3.1 g (19 mmol) of N-hydroxyphthalimide, 2.68 ml (19 mmol) of triethylamine and 31 ml of N,N-dimethylformamide was dropwise added at 0°) C., and stirred for 12 hours at room temperature. Then, the reaction solution was poured into a 10% sodium hydrogencarbonate aqueous solution, and extracted with ethyl acetate 3 times, followed by washing with a saturated sodium chloride aqueous solution. After the organic layer was dried over anhydrous sodium sulfate, the solvent was distilled off under reduced pressure. The residue was subjected to silica gel column chromatography, and the fractions containing the desired product (ethyl acetate:hexane =3:1) was concentrated to obtain 9.75 g (yield: 88%) of N-[α-benzhydryloxycarbonyl-3,4-di(2-methoxyethoxymethoxy) benzyloxy]phthalimide.

NMR(DMSO-d₆)δ: 3.20(6H,s), 3.38(4H,m), 3.70 (4H,m), 5.15(2H,s), 5.20(2H,m), 5.95(1H,s), 6.83(1H,s), 7.00-7.50(13H,m), 7.78(4H,s)

(F) 9.75 g (14.5 mmol) of the compound obtained in the above reaction (E) was dissolved 100 ml of methylene chloride, and 45 ml of methanol solution containing 3.12 ml (49 mmol) a 80% hydrazine hydrate was dropwise added at 0° C. The reaction solution was stirred for 15 minutes, and the precipitates were filtered off. The filtrate was dried over anhydrous sodium sulfate, and the solvent was distilled off under reduced pressure. The residue was subjected to silica gel column chromatography (Wakogel C-300). The fractions containing the desired product (ethyl acetate:hexane =1:3) was concentrated to obtain 5.1 g (yield: 65%) of O -[α-benzhydryloxycarbonyl-3,4-di(2-methoxyethoxymethoxy)benzyl]hydroxylamine.

NMR(DMSO-d₆)δ: 3.20(6H, s), 3.48(4H, m), 3.72 (4H, m), 5.14(3H, s), 5.22(2H, s), 6.38(2H, br s), 6.80(1H, s), 7.00-7.50(13H, m)

(G) 5.1 g (9.4 mmol) of the compound obtained in the above reaction (F) was dissolved in 50 ml of methanol, and a suspension of 3.5 g (8.5 mmol) of 2-(2-tritylaminothiazol-4-yl)glyoxylic acid and 41 ml of methanol was added thereto. After stirring for 15 minutes, white precipitates formed were filtered off, and washed with methanol, followed by drying. 4.87 g (yield: 55%) of the above identified compound was obtained.

NMR(DMSO-d₆)δ: 3.20(6H, s), 3.41(4H, m), 3.72 (4H, m), 5.15(2H, br s), 5.26(2H, br s), 5.77(1H, s), 6.85(2H,s), 6.90-7.70(28H, m), 8.80(1H, br s)

REFERENCE EXAMPLE 28

Preparation of
2-mercapto-5-[3,4-di(2-methoxyethoxymethoxy)phenyl]-1,3,4-thiadiazole (A) 15.0 g (50.7 mmol) of 3,4-di(2-methoxyethoxymethoxy)benzonitrile was dissolved in 15.0 ml of pyridine, and 7.5 ml (50 mmol) of triethylamine was added thereto. Hydrogen sulfide was introduced to the mixture at room temperature for 6 hours under stirring. After adding ethyl acetate and water to the reaction solution, the organic layer was separated and dried over anhydrous sodium sulfate. The solvent was distilled off under reduced pressure to obtain 18.8 g (yield: 100%) of a crude product of 3,4-di(2-methoxyethoxymethoxy)-thiobenzamide, which was used for the next reaction without purification.

IR(KBr)cm⁻¹: 3320, 3200, 2900, 1635, 1515

(B) 2.0 g (5.8 mmol) of the compound obtained in the above reaction (A) was dissolved in 20.0 ml of ethanol, and 0.40 ml of hydrazine hydrate was added thereto. The mixture was stirred at 70° C. for 1 hour. 0.40 g (5.70 mmol) of potassium hydroxide and 1.38 ml (18 mmol) of carbon disulfide was added to the reaction solution and refluxed for 20 minutes. The solvent was distilled off under reduced pressure. The residue was dissolved in water and washed with ethyl acetate. The water layer was adjusted to pH3.0 with 2N hydrochloric acid, extracted with ethyl acetate and dried over anhydrous sodium sulfate. The solvent was distilled off under reduced pressure, and the crystal residue was washed with ethyl ether to obtain 0.94 g (yield: 40%) of the above identified compound.

IR(KBr)cm⁻¹: 3160, 2500, 1600, 1585, 1510, 1455

NMR(DMSO-d₆)δ: 3.25(6H,s), 3.50(4H,m), 3.78(4H,m), 5.34(4H,br s), 7.26(1H,d,J=8Hz), 7.33(1H,dd,J=1 and 8Hz), 7.52(1H,d,J=1Hz)

Elemental analysis: as $C_{16}H_{22}N_2O_6S_2$ Calculated (%): C,47.75 ; H,5.51 ; N,6.9 ; S,15.93. Found (%) : C,47.75 ; H,5.44 ; N,6.94 ; S,15.72

REFERENCE EXAMPLE 29

Preparation of
5-(3,4-dihydroxyphenyl)-2-mercapto-1,3,4-thiadiazole (A) 10 g (178 mmol) of potassium hydroxide was dissolved in 400 ml of ethanol, and 20 g (119 mmol) of protocatechuohydrazide was added at not more than 5° C. under stirring. To the solution 28.0 ml of carbon disulfide was dropwise added in 10 minutes and stirred at a temperature from 0° to 10°) C., the precipitates were collected by filtration. The precipitates were washed and dried to obtained 25.3 g (yield: 75.3%) of potassium 3-protocatechuoyl dithiocarbazate.

(B) 25.3 g (89.6 mmol) of the compound obtained in the above reaction (A) was added in limited amounts to 125 ml of concentrated sulfuric acid at not more than 10° C. in 20 minutes. The mixture was stirred at 10° C. for 20 minutes. The reaction solution was added in limited amounts to 600 g of ice and 300 ml of water and further stirred for 10 minutes. The precipitates were collected by filtration. The precipitates were dissolved in 125 ml of acetone, and 600 ml. of ethyl acetate, 20 ml of water and 1 g of active carbon were added. The mixture was stirred for 15 minutes. After the active carbon was filtered off, the filtrate was washed sequentially with 200 ml of a 5% sodium thiosulfide aqueous solution, 150 ml of water and a saturated sodium chloride aqueous solution. The organic layer was dried over anhydrous magnesium sulfate, and the solvent was distilled off. The crystal residue was washed with ethyl ether to obtain 3.6 g (yield: 17.8%) of the above identified compound.

IR(KBr)cm⁻¹: 3600-2000, 1650, 1600, 1430, 1300, 1250

NMR(DMSO-d₆)δ: 6.82(1H,d,J=9Hz), 7.01(1H,dd,J=2 and 9Hz), 7.13(1H,d,J=2Hz), 9.50(2H,br s), 14.38(1H,br s)

REFERENCE EXAMPLE 30

Preparation of
4-(3,4-dihydroxyphenyl)-2-mercapto-thiazole 10.0 g (53.6 mmol) of 2-chloro-3'4'-dihydroxyacetophenone was dissolved in 100 ml of methanol, and 5.90 g (53.6 mmol) of ammonium dithiocarbamate. The mixture was stirred at room temperature for 30 minutes, and the solvent was distilled off under reduced pressure. Water was added to the residue, adjusted to pH2.0 and extracted twice with ethyl acetate. The extract was dried over anhydrous sodium sulfate and concentrated.

The crystal residue thus obtained was washed with ethyl ether to obtain 8.80 g (yield: 72.9%) of the above identified compound.

MP: 236°) C. (recrystalline solvent: ethylacetate)
IR(KBr)cm⁻¹: 3420, 1615, 1525, 1470
NMR(DMSO-d₆)δ: 6.77(1H,d,J=9Hz), 6.92(1H,s), 7.03(1H,dd,J=2 and 9Hz), 7.08(1H,d,J=2Hz), 9.15(1H,m)

Elemental analysis: as $C_9H_7NO_2S_2$ Calculated (%): C,47.98 ; H,3.13 ; N,6.21 ; S,28.47., Found (%) : C,48.07 ; H,3.02 ; N,6.22 ; S,28.16

REFERENCE EXAMPLE 31

Preparation of 4-carboxy-5-(3,4-dihydroxyphenyl)-2-mercaptothiazole (A) 48.3 g (yield: 58%) of 3-(3,4-methylenedioxyphenyl)pyruvic IR(KBr)cm : 3600-2000, 1650, 1600 acid was obtained in accordance with the method disclosed in organic synthesis Coll. Vol. II, P. 1-3, P. 11-12, P. 519-520by using 60.1 g of piperonal as a starting material.

IR(KBr)cm$^{-1}$: 1 670, 1500, 1490, 1450, 1250, 1040
NMR(DMSO-d$_6$)δ: 6.03(2H,s), 6.38(1H,s), 6.87(1H,d,J=7.5Hz), 7.23(1H,d,J=7.5Hz), 7.46(1H,s), 9.00(2H,s)

(B) 10.4 g (0.05 mol) of the compound obtained in the above reaction (A) was suspended in 100 ml of ethyl acetate, 2.56 ml (0.05 mol) of bromine was added thereto at −10° C. The mixture was stirred at the same temperature for 30 minutes. 200 ml of ethanol was added to the reaction solution at −10°) C., and 9.92 g (0.09 mol) of ammonium dithiocarbamate was added at −10° C. The mixture was stirred at the same temperature for 20 minutes and stirred at room temperature for 2 hours. The reaction solution was cooled in an ice bath for 40 minutes, and insoluble substances were collected by filtration. The insoluble substances were washed with 40 ml of ethyl acetate. The filtrate and the washing solution were put together and concentrated under reduced pressure. 350 ml of water was added to the residue and the solution was heated at 80° C. for 18 hours. The gummy insoluble substances were filtered off under heating. The filtrate was adjusted to pH1.5 with 6N hydrochloric acid under cooling with ice, and the precipitates were collected by filtration. The precipitates were washed with 30 ml of water and dried to obtain 7.23 g of the above identified compound as yellow powders. Further, the above gummy insoluble substances were suspended in 20 ml of acetone, and insoluble substances were collected by filtration and dried to obtain 1.02 g of the secondary crystal. The total yield was 8.25 g (yield: 66%). IR(KBr)cm$^{-1}$: 1710, 1690, 1500, 1490, 1450, 1430, 1320, 1260, 1060, 1040

NMR(DMSO-d$_6$)δ: 6.10(2H,s), 6.97(2H,s), 7.12(1H,s), 12.0-15.0(2H,br s)

(C) 6.79 g (0.024 mol) of the compound obtained in the above reaction (B) was suspended in 180 ml of methylene chloride and 13 ml of ethanethiol, and 16.0 g (0.12 mol) of anhydrous aluminum chloride was added thereto at 5° C. The mixture was stirred at the same temperature for 4 hours, and stirred at 10° C. for 24 hours. 100 ml of 6N hydrochloric acid was dropwise added to the mixture under cooling with ice and the mixture was stirred at the same temperature for 1.5 hours. Insoluble substances were collected by filtration, washed twice with 50 ml of water and dried to obtain 5.53 g of a crude product. The crude product was recrystallized in a mixed solvent of methanol and water to obtain 3.93 g (yield: 61%) of the above identified compound as yellow needles.

MP: 245-247° C. (decomposed)

IR(KBr)cm$^{-1}$: 1710, 1700, 1610, 1520, 1480, 1350, 1300, 1250, 1210, 1190, 1120, 1070, 1010
NMR(DMSO-d$_6$)δ: 6.79(2H,s), 6.90(1H,s),
UVλ$_{max}^{MeOH}$nm (E$_{1cm}^{1\%}$):340.5 (481)$^{309.5\ (480)}$,

REFERENCE EXAMPLE 32

Preparation of 4-(3,4-diacetoxyphenyl)-5-benzhydryloxycarbonylmethyl-2-mercaotothiazole (A) 70 g (0.7 mol) of succinic anhydride and 96.6 g (0.7 mol) of veratrol were dissolved in 2000 ml of methylene chloride, and 237 g (1.75 mol) of anhydrous aluminum chloride was added thereto at room temperature. The mixture was stirred at the same temperature for 6 hours. The reaction solution was allowed to stand for 15 hours, and then 1600 ml of 6N hydrochloric acid was dropwise added under stirring. The mixture was stirred for 1 hour, and the organic layer was separated. 300 ml of water was added to the organic layer and adjusted to pH7.5 with a saturated sodium hydrogencarbonate aqueous solution. The water layer was separated, adjusted to pH2.5 with 6N hydrochloric acid and allowed to stand in a refrigerator for 2 days. The precipitated crystals were collected by filtration, washed and dried to obtain 106.8 g (yield: 64%) of 3-(3,4-dimethoxybenzoyl)propionic acid.

IR(KBr)cm$^{-1}$: 3360, 1740, 1665, 1590, 1515, 1415 1335, 1270, 1150, 1020, 800, 770, 610,
NMR(DMSO-d$_6$)δ: 2.56(2H,t,J=6.0Hz), 3.21(2H,t,J=6.0Hz), 3.93(3H,s), 3.95(3H,s), 7.04(1H,d,J=8.7Hz), 7.45(1H,d,J=1.5Hz), 7.67(1H,dd,J=1.5 and 4.5Hz), 11.0-12.5(1H,br)

(B) To 106 g (0.445 mol) of the compound obtained in the above reaction (A), 1070 ml of a 48% hydrobromic acid was added and boiled under reflux for 5 hours. The solvent was distilled off under reduced pressure. 1000 ml of water was added to the residue, dissolved under heating and treated with an active carbon. The filtrate was kept to cool overnight to obtain blakish brown crystals. This colored crystals was dissolved in 1000 ml of water under heating, treated twice with active carbon and kept to cool overnight, whereby 37.2 g (yield: 39.8%) of 3-(3,4-dihydroxybenzoyl)propionic acid as colorless plates.

IR(KBr)cm$^{-1}$: 3460, 3370, 1740, 1660, 1590, 1405, 1380, 1245, 1165, 1125, 885, 820, 610
NMR(DMSO-d$_6$)δ: 2.53(2H,t,J=6.2Hz), 3.12(2H,t,J=6.2Hz), 6.82(1H,d,J=8.7Hz), 7.30-7.50(2H,m), 9.00-10.50(2H,br), 11.30-12.80(1H,br)

(C) To 2.0 g (9.52 mmol) of the compound obtained in the above reaction (B), 9.0 ml of acetic anhydride and 0.78 g (9.5 mmol) of sodium acetate were added and heated under reflux for 30 minutes. The solvent was distilled off under reduced pressure. The ethyl acetate was added to the residue, washed with a 5% sodium hydrogencarbonate aqueous solution and dried over anhydrous magnesium sulfate. The solvent was distilled off under reduced pressure, and the residue was purified by silica gel column chromatography (Wakogel C-300, 2% methanol/methylene chloride) to obtain 1.33 g (yield: 50%) of 4-(3,4-diacetoxyphenyl)-2(3H)-furanone.

NMR(DMSO-d$_6$)δ: 2.30(6H,s), 3.58(2H,m), 6.24(1H,m), 7.30-7.60(3H,m)

(D) 300 mg (1.08 mmol) of the compound obtained in the above reaction (C) was dissolved 8 ml of a mixed solvent of dioxane/water (3:1) and 193 mg of N-bromosuccinimide at room temperature. The mixture was stirred for 15 minutes. 300 mg (1.54 mmol) of diphenyldiazomethane was added to the filtrate and stirred for 1 hour. The solvent was distilled off under reduced pressure, and the residue was purified by silica gel chromatography (Wakogel C-300, methyl acetate:-hexane=1:3) to obtain 350 mg (yield: 60%) of benzhydryl 3-(3,4-diacetoxybenzoyl)-3-bromopropionate.

NMR((DMSO-d$_6$)δ: 2.33(6H,s), 3.20-3.80(2H,m), 6.00(1H,br t,J=8Hz), 6.80(1H,s), 7.10-7.60(13H,m)

(E) 700 mg (1.30 mmol) of the compound obtained in the above reaction (D) was dissolved in 7.0 ml of N,N-dimethylformamide, and 143 mg (1.30 mmol) of ammonium dithiocarbamate was added under cooling with ice. The mixture was stirred for 15 minutes. The solvent was distilled off under reduced pressure, and the residue was purified by silica gel column chromatography (Wakogel C-300, methyl acetate:hexane=1:2) to obtain 470 mg (yield: 68%) of the above identified compound.

IR(KBr)cm$^{-1}$: 3400, 3240, 1750, 1735, 1500, 1470, 1370, 1260, 1200, 1160, 1050

NMR(DMSO-d$_6$)δ: 2.30(6H,s), 3.00(2H,m), 4.40(1H,br t,J=7Hz), 6.78(1H,s), 7.10-7.60(13H,m)

REFERENCE EXAMPLE 33 mercaptooxazole 10 g (53.6 mmol) of 2-chloro-3',4'-dihydroxyacetophenone was dissolved in 50 ml of acetone, and 600 mg (4.0 mmol) of sodium iodide and 5.23 g (80.5 mmol) of sodium azide were added thereto. The mixture was refluxed for 24 hours. Insoluble substances in the reaction solution were filtered off and concentrated under reduced pressure. Ethyl acetate was added to the reaction solution, and washed sequentially with water and a saturated sodium chloride aqueous solution, and dried over anhydrous sodium sulfate. The solvent was distilled off under reduced pressure. The oily residue was dissolved in 100 ml of methanol and 13.6 ml of concentrated hydrochloric acid, and 1.5 g of a 10% palladium carbon catalyst was added thereto. The mixture was stirred at 40° C. for 5 hours under hydrogen gas atmosphere. The reaction solution was filtered and the filtrate was concentrated under reduced pressure. To the concentrated residue, acetone was added, and the precipitated crystals were collected by filtration to obtain 5.5 g (yield: 50.4%) of 2-amino-3',4'-dihydroxyacetophenone hydrochloride.

NMR(DMSO-d$_6$/D$_2$O)δ: 4.40(2H,s), 6.90(1H,d,J=9Hz), 7.30-7.50(2H,m)

(B) 1.0 g (4.9 mmol) of the compound obtained in the above reaction (A) was suspended in 17 ml of 0.043 N sodium ethoxide ethanol solution, and 2.1 ml (35 mmol) of carbon disulfide was added thereto. The mixture was stirred at 60°) C. for 20 hours. The reaction solution was poured into 50 ml of water, adjusted to pH1.5 with 6N hydrochloric acid, stirred for 1 hour and extracted with ethyl acetate. The organic layer was washed sequentially with water and a saturated sodium chloride aqueous solution and dried over anhydrous sodium sulfate. The solvent was distilled off under reduced pressure to obtain 750 mg (yield: 73%) of the above identified compound.

MP: 215-218° C.

IR(KBr)cm$^-$: 1640, 1600, 1520, 1500, 1300, 1180, 1120

NMR(DMSO-d$_6$/D$_2$O)δ :6.70-6.95(2H,m), 7.00(1H,s), 7.42(1H,s)

Elemental analysis: as C$_9$H$_7$NO$_3$S Calculated (%): C,51.12 ; H,3.12 ; N,6.43, Found (%) : C,51.67 ; H,3.37 ; N,6.69

REFERENCE EXAMPLE 34

Preparation of 2-mercapto-5,6-di(2-methoxyethoxymethoxy)benzimidazole (A) 10 g (44 mmol) of 4,5-dimethoxy-1,2-dinitrobenzene was suspended in 150 ml of a 45% hydrobromic acid and boiled under refluxing for 6 hours. The reaction solution was allowed to cool to room temperature, and 500 ml of water was added thereto The solution was extracted three times with ethyl acetate. The organic layer was washed with a 10% sodium hydrogencarbonate and dried over anhydrous sodium sulfate. The solvent was distilled off under reduced pressure, and the crystal residue was washed with methylene chloride to obtain 7 g (yield: 79%) of 4,5-dihydroxy-1,2-dinitrobenzene.

NMR(DMSO-d$_6$)δ: 7.48(2H,s), 8.50(2H, br s)

(B) 28 g (0.14 mol) of the compound obtained in the above reaction (A) was suspended in 280 ml of methylene chloride, and 30 ml (0.42 mol) of ethyl diisopropylamine was added and dissolved at room temperature. To the reaction solution, 30 ml (0.42 mol) of 2-methoxyethoxymethyl chloride was dropwise added at 0° d stirred for 30 minutes. The reaction solution was poured into water and the organic layer was washed with 1N sodium hydroxide aqueous solution and a saturated sodium chloride aqueous solution and dried over anhydrous sodium sulfate. The solvent was distilled off under reduced pressure to obtain 39 g (yield: 74%) of 4,5di(2-methoxyethoxymethoxy)-1,2-dinitrobenzene.

IR(KBr)cm$^{-1}$: 2900, 1525, 1362

NMR(DMSO-d$_6$)δ: 3.23(6H,s), 3.50(4H,m), 3.78(4H,m), 5.58(4H,s), 8.01(2H,s)

(C) 9.5 g (25 mmol) of the compound obtained in the above reaction (B) was dissolved in 180 ml of ethanol, and 1 g of a 10% palladium carbon catalyst was added thereto. A catalystic hydrogenation was conducted at 80° C. for 2 hours, and 1 g of a 10% palladium carbon catalyst was further added to the reaction solution. A catalystic hydrogenation under the same condition as in the previous hydrogenation was conducted (this operation was repeated twice). The catalysts were filtererd off, and the filtrate was concentrated under reduced pressure. The residue was subjected to silica gel column chromatograpy (Wakogel.C-300, ethyl acetate:hexane =1:1), and the fraction containing the desired product was concentrated to obtain 5.07 g (yield: 57%) of 4,5-di(2-methoxyethoxymethoxy)-2-nitroaniline (which was immediately used for the next reaction due to unstability).

(D) 3.5 g (10 mmol) of the compound obtained in the above reaction (C) was dissolved in 70 ml of ethanol, and 0.6 g of a 10% of palladium carbon catalyst was added thereto. A catalic hydrogenation was conducted at 80° C. for 1 hour, and 0.6 g of a 10% palladium carbon catalyst was further added to the reaction solution. Catalytic hydrogenation was conduced under the same conditions as in the previous catalytic hydrogenation (this operation was repeated twice). The catalysts were filtered off, and 10 g (6.1 mmol) of potassium 0-ethyl dithiocarbonate and 3 ml of water were added to the filtrate. The mixture was boiled under refluxing for 3 hours. The solvent was distilled off under reduced pressure. The residue was dissolved in water, adjusted to pH3.0 with acetic acid and extracted three times with ethyl acetate. The organic layer was dried, and concentrated under reduced pressure. The residue was subjected to silica gel column chromatography (Wakogel C-300, ethyl acetate:hexane =3:1), and the fraction containing the desired product was concentrated to obtain 2-mercapto-5,6-di(2-methoxyethoxymethoxy)-benzimidazole (yield: 61%).

IR(KBr)cm$^{-1}$: 3280, 1622, 1475, 1332
NMR(DMSO-d$_6$)δ: 3.25(6H,s), 3.32(2H,s), 3.48(4H,m), 3.75(4H,m), 5.20(4H,s), 6.94(2H,s)

REFERENCE EXAMPLE 35

Preparation of 2-mercapto-5,6-di(2-methoxyethoxymethoxy)-1-methylbenzimidazole (A) 1.57 g (4.54 mmol) of 4,5-di(2-methoxyethoxymethoxy)-2-nitroaniline obtained in REFERENCE EXAMPLE 34 (C) was dissolved in 16 ml of N,N-dimethylformamide, and 2 g (8.63 mmol) of silver oxide and 10 ml (160 mmol) of methyl iodide were added thereto. The mixture was stirred at room temperature for 1 hour. The solvent was distilled off under reduced pressure, and the residue was subjected to silica gel column chromatography (Wakogel C-300, ethyl acetate:hexane =1:1). The fraction containing the desired product was concentrated to obtain 0.85 g of a crude product of 4,5-di(2-methoxyethoxymethoxy)-N-methyl-2-nitroaniline.

(B) 0.85 g of the crude product obtained in the above reaction (A) was dissolved in 16 ml of ethanol, and 0.4 g of 20% palladium carbon catalyst was added thereto. A catalytic hydrogenation was conducted at 80° C. for 2 hours, and the catalyst was filtered off. 1 g (6.25 mmol) of potassium 0 ethyl dithiocarbonate was added to the filtrate and boiled under refluxing for 2 hours. The reaction solution was concentrated under reduced pressure. The residue was dissolved in water, adjusted to pH5.0 with acetic acid and extracted with ethyl acetate. The organic layer was dried over anhydrous sodium sulfate, and the solvent was distilled off under reduced pressure. The residue was subjected to silica gel column chromatography (Wakogel C-300, ethyl acetate:hexane =3:1) to obtain 67 mg of the above identified compound.

NMR(CDCl$_3$)δ: 3.40(6H,s), 3.60(4H,m), 3.68(3H,s), 3.88(4H,m), 5.27(2H,s), 5.30(2H,s), 7.02(1H,s), 7.08(1H,s)

REFERENCE EXAMPLE 36

Preparation of 2-mercapto-5,6-di(2-methoxyethoxymethoxy)benzoxazole (A) 5.4 g (17 mmol) of 3,4-di(2-methoxyethoxymethoxy)benzaldehyde was dissolved in 216 ml of methylene chloride, and a 80% m-chloroperbenzoic acid was added thereto. The mixture was boiled under refluxing for 20 hours. The reaction solution was washed with sodium hydrogencarbonate aqueous solution and a saturated sodium chloride aqueous solution, and dried. The solvent was distilled off under reduced pressure to obtain 4.85 g (yield: 86%) of 0-formyl-3,4-di(2-methoxyethoxymethoxy)phenol, which was used for the next reaction without purification.

NMR(CDCl$_3$/DMSO-d$_6$)δ: 3.36(6H,s), 3.58(4H,m), 3.82(4H,m), 5.28(4H,br s), 6.73(1H,dd,J=2 and 9Hz), 7.02(1H,d,J=2Hz), 7.29(1H,d,J=9Hz)

(B) 4.85.g (14.7 mmol) of the compound obtained in the above reaction (A) was dissolved in 4 ml of methanol, and 7.0 ml (17.6 mmol) of a 10% sodium hydroxide was added thereto. The mixture was stirred at room temperature for 30 minutes. The reaction solution was poured into 100 ml of water and washed with ethyl acetate. The water layer was adjusted to pH5.0 with 6N hydrochloric acid, extracted with ethyl acetate and dried over anhydrous sodium sulfate. The solvent was distilled off under reduced pressure. The residue was dissolved in 8 ml of acetic acid, and 0.70 ml (11 mmol) of concentrated nitric acid was added at 10° C. The mixture was stirred for 1 hour. The reaction solution was poured into ethyl acetate and washed sequentially with water and a saturated sodium hydrogencarbonate. The organic layer was dried and concentrated. The residue was subjected to silica gel column chromatography (Wakogel C-300, ethyl acetate:hexane=1:3), and the fraction containing the desired product was concentrated to obtain 1.51 g (yield: 29.6%) of 4,5-di(2-methoxyethoxymethoxy)-2-nitrophenol.

NMR(DMSO-d$_6$)δ: 3.25(6H,s), 3.50(4H,m), 3.76(4H,m), 5.23(4H,s), 6.87(1H,s), 7.75(1H,s)

(C) 1.5 g (4.3 mmol) of the compound obtained in the above reaction (B) was dissolved in 30 ml of ethanol, and 0.5 g of a 10% palladium carbon catalyst was added thereto. A catalytic hydrogenation was conducted at 70° C. for 1.5 hours. The catalyst was filtered off and 0.36 g (4.73 mmol) of carbon disulfide, 0.35 g (5.0 mmol) of a 80% potassium hydroxide aqueous solution and 0.78 ml (43 mmol) of water was added thereto. The mixture was boiled under refluxing for 1.5 hours. The solvent was distilled off under reduced pressure. The residue was dissolved in water, adjusted to pH5.0 with 6N hydrochloric acid and extracted with ethyl acetate. The organic layer was dried and concentrated . The residue was subjected to column chromatography (Wakogel C-300, ethyl acetate: hexane=1:1) to obtain 857 mg (yield: 55.5%) of the above identified compound.

NMR(DMSO-d$_6$)δ: 3.22(6H,s), 3.46(4H,m), 3.75(4H,m), 5.23(4H,s), 7.00(1H,s), 7.34(1H,s)

We claim:

1. A compound having the formula:

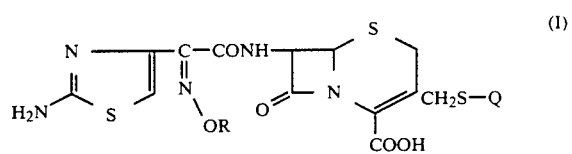

wherein R is a straight chain or branched chain lower alkyl, or cyclic lower alkyl group which may be substituted by a carboxyl group, and Q is,

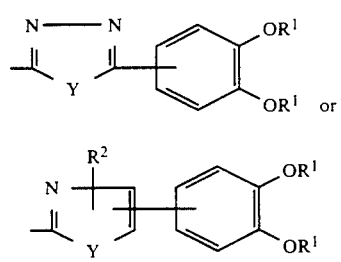

(wherein R$^1$ is a hydrogen atom or an acetyl group, R$^2$ is a hydrogen atom, a carboxyl group or a carboxymethyl group, Y is a sulfur atom or an oxygen atom); or a pharmaceutically acceptable salt, physiologically hydrolyzable ester or solvate thereof.

2. An antibacterial agent comprising an antibacterially effective amount of a compound having the formula:

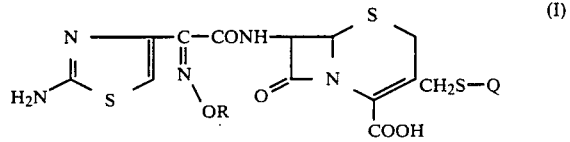

wherein R is a straight chain or branched chain lower alkyl, or cyclic lower alkyl group which may be substituted by a carboxyl group, and Q is,

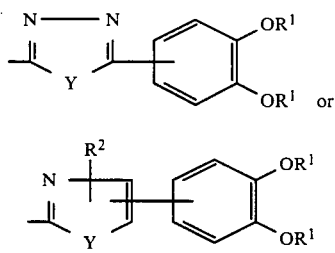

(wherein $R^1$ is a hydrogen atom or an acetyl group, $R^2$ is a hydrogen atom, a carboxyl group or a carboxymethyl group, Y is a sulfur atom or an oxygen atom); or a pharmaceutically acceptable salt, physiologically hydrolyzable ester or solvate thereof.

3. The compound according to claim 1, which is (1)  7β-[2-(2-aminothiazol-4-yl)-2-methoxyiminoacetamido]-3-[5-(3, 4-dihydroxyphenyl)-1,3,4-oxadiazol-2-yl]thiomethyl-3-cephem-4-carboxylic acid (2)  3-[5-(3,4-diacetoxyphenyl)-1,3,4-oxadiazol-2-yl]-thiomethyl-7β-[2-( 2-aminothiazol-4-yl)-2-methoxyiminoacetamido]-3-cephem-4-carboxylic acid (3)  7β-[2-(2-aminothiazol-4-yl)-2-ethoxyiminoacetamido]-3-[5-(3, 4-dihydroxyphenyl)-1,3,4-oxadiazol-2-yl]-thiomethyl-3-cephem-4-carboxylic acid (4)  3-[5-(3,4-diacetoxyphenyl)-1,3,4-oxadiazol-2-yl]-thiomethyl-7β-[2-(2-aminothiazol-4-yl)-2-ethoxyiminoacetamido]-3-cephem-4-carboxylic acid (5)  7β-[2-(2-aminothiazol-4-yl)-2-isopropoxyiminoacetamido]-3-[5-(3, 4-dihydroxyphenyl)-1,3,4-oxadiazol-2-yl]thiomethyl-3-cephem-4-carboxylic acid (6)  7β-[2-allyloxyimino-2-(2-aminothiazol-4-yl)acetamido]-3-[5-(3, 4-dihydroxyphenyl)-1,3,4-oxadiazol-2-yl]thiomethyl-3-cephem-4-carboxylic acid (7)  7β-[2-(2-aminothiazol-4-yl)-2-propargyloxyiminoacetamido]-3-[5-(3, 4-dihydroxyphenyl)-1,3,4-oxadiazol-2-yl]thiomethyl-3-cephem-4-carboxylic acid (8)  7β-[2-(2-aminothiazol-4-yl)-2-carboxymethoxyiminoacetamido]-3-[5-(3, 4-dihydroxyphenyl)-1,3,4-oxadiazol-2-yl]thiomethyl-3-cephem-4-carboxylic acid (9)  7β-[2-(2-aminothiazol-4-yl)-2-(1-carboxy-1-methylethoxyimino) acetamido]-3-[5-(3,4-dihydroxyphenyl)-1'3,4-oxadiazol-2-yl]thiomethyl-3-cephem 4-carboxylic acid

(10)  7β-[2-(2-aminothiazol-4-yl]-2-(1-carboxy-1-cyclopropoxyimino) acetamido]-3-[5-(3,4-dihydroxyphenyl)-1,3,4-oxadiazol-2-yl]thiomethyl-3-cephem-4carboxylic acid

(11)  7η-[2-(2-aminothiazol-4-yl)-2-benzyloxyiminoacetamido]-3-[5-(3, 4-dihydroxyphenyl)-1,3,4-oxadiazol-2-yl]thiomethyl-3-cephem-4-carboxylic acid

(12)  7β-[2-(2-aminothiazol-4-yl)-2-(3,4-dihydroxybenzyloxyimino) acetamido]-3-[5-(3,4-dihydroxyphenyl)-1,3, 4-oxadiazol-2-yl]thiomethyl-3-cephem-4-carboxylic acid

(13)  7β-[2-(2-aminothiazol-4-yl)-2-(α-carboxybenzyloxyimino) acetamido]-3-[5-(3,4-dihydroxyphenyl)-1,3, 4-oxadiazol-2-yl]thiomethyl-3-cephem-4-carboxylic acid

(14)  7β-[2-(2-aminothiazol-4-yl)-2-(o-carboxy-3,4dihydroxybenzyloxyimino) acetamido]-3-[5-(3,4-dihydroxyphenyl)-1,3,4-oxadiazol-2-yl]thiomethyl-3-cephem-4-carboxylic acid

(15)  7β-[2-(2-aminothiazol-4-yl)-2-(4-hydroxybenzyloxyimino) acetamido]-3-[5-(3,4-dihydroxyphenyl)-1,3,4-oxadiazol-2-yl]thiomethyl-3-cephem-4carboxylic acid

(16)  7β-[2-(2-aminothiazol-4-yl)-2-(3-carboxy-4-hydroxybenzyloxyimino) acetamido]-3-[5-(3,4-dihydroxyphenyl)-1,3,4-oxadiazol-2-yl]thiomethyl-3-cephem-4-carboxylic acid

(17)  7β-[2-(2-aminothiazol-4-yl)-2-(4-carboxybenzyloxyimino) acetamido]-3-[5-(3,4-dihydroxyphenyl)-1,3,4-oxadiazol-2-yl]thiomethyl-3-cephem-4-carboxylic acid

(18)  7β-[2-(2-aminothiazol-4-yl)-2-(3-carboxybenzyloxyimino) acetamido]-3-[5-(3,4-dihydroxyphenyl)-1,3,4-oxadiazol-2-yl]thiomethyl-3-cephem-4carboxylic acid

(19)  7β-[2-(2-aminothiazol-4-yl)-2-(4-carboxylmethylbenzyloxyimino) acetamido]-3-[5-(3,4-dihydroxyphenyl)-1,3,4-oxadiazol-2-yl]thiomethyl-3-cephem-4-carboxylic acid

(20)  7β-[2-(2-aminothiazol-4-yl)-2-phenoxyiminoacetamido]-3-[5-(3, 4-dihydroxyphenyl)-1,3,4-oxadiazol-2-yl]thiomethyl-3-cephem-4-carboxylic acid

(21)  7β-[2-(2-aminothiazol-4-yl)-2-(2-carboxymethylbenzyloxyimino) acetamido]-3-[5-(3,4-dihydroxyphenyl)-1,3,4-oxadiazol-2-yl]thiomethyl-3-cephem-4-carboxylic acid

(22)  7β-[2-(2-aminothiazol-4-yl)-2-(α-carboxybenzyloxyimino) acetamido]-3-[5-(3,4-dihydroxyphenyl)-1,3, 4-oxadiazol-2-yl]thiomethyl -3-cephem-4carboxylic acid

(23)  7β-[2-(2-aminothiazol-4-yl)-2-methoxyiminoacetamido]-3-[5-(3, 4-dihydroxyphenyl)-1,3,4-thiadiazol2-yl]thiomethyl-3-cephem-4-carboxylic acid

(24)  3[5-(3,4-diacetoxyphenyl)-1,3,4-thiadiazol-2-yl]thiomethyl-7β-[2-(2-aminothiazol-4-2-methoxyiminoacetamido] 3-cephem-4-carboxylic acid

(25)  7β-[2-(2-aminothiazol-4-yl)-2-methoxyiminoacetamido]-3-[5-(3, 4-dihydroxyphenyl)-1,3,4-thiadiazol-2-yl]thiomethyl-3-cephem-4-carboxylic acid

(26) 3-[5-(3,4-diacetoxyphenyl)-1,3,4-thiadiazol-2-yl]-thiomethyl-7β-[2-(2-aminothiazol-4-yl)-2-ethoxyiminoacetamido]-3-cephem-4-carboxylic acid

(27)  7β-[2-(2-aminothiazol-4-yl)-2-isopropoxyiminoacetamido]-3-[5-(3, 4-dihydroxyphenyl)-

(28) 7β-[2-allyloxyimino-2-(2-aminothiazol-4-yl)acetamido]-3-[5-(3, 4-dihydroxyphenyl)-1,3,4-thiadiazol-2-yl]thiomethyl-3-cephem-4-carboxylic acid

(29) 7β-[2-(2-aminothiazol-4-yl)-2-propargyloxyiminoacetamido]-3-[5-(3, 4-dihydroxyphenyl)-1,3,4-thiadiazol-2-yl]thiomethyl-3-cephem-4-carboxylic acid

(30) 7β-[2-(2-aminothiazol-4-yl)-2-benzyloxyiminoacetamido]-3-[5-(3, 4-dihydroxyphenyl)-1,3,4-thiadiazol-2-yl]thiomethyl-3-cephem-4-carboxylic acid

(31) 7β-[2-(2-aminothiazol-4-yl)-2-(3,4-dihydroxybenzyloxyimino) acetamido]-3-[5-(3,4-dihydroxyphenyl)-1,3,4-thiadiazol-2-yl]thiomethyl-3-cephem-4carboxylic acid

(32) 7β-[2-(2-aminothiazol-4-yl)-2-(1-carboxy-1methylethoxyimino) acetamido]-3-[5-(3,4-dihydroxyphenyl)-1, 3,4-thiadiazol-2-yl]thiomethyl-3-cephem-4carboxylic acid

(33) 7β-[2-(2-aminothiazol-4-yl)-2-(1-carboxy-1-cyclopropoxyimino) acetamido]-3-[5-(3,4-dihydroxyphenyl)-1,3, 4-thiadiazol-2-yl]thiomethyl-3-cephem-4carboxylic acid

(34) 7β-[2-(2-aminothiazol-4-yl)-2-(2-carboxymethylbenzyloxyimino) acetamido]-3-[5-(3,4-dihydroxyphenyl)-1,3, 4-thiadiazol-2-yl]thiomethyl-3-cephem-4carboxylic acid

(35) 7β-[2-(2-aminothiazol-4-yl)-2-(α-carboxybenzyloxyimino) acetamido]-3-[5-(3,4-dihydroxyphenyl)-1,3, 4-thiadiazol-2-yl]thiomethyl-3-cephem-4carboxylic acid

(36) 7β-[2-(2-aminothiazol-4-yl)-2-(o-carboxy-3,4dihydroxybenzyloxyimino) acetamido]-3-[5-(3,4-dihydroxyphenyl)-1,3, 4-thiadiazol-2-yl]thiomethyl-3-cephem-4-carboxylic acid

(37) 7β-[2-(2-aminothiazol-4-yl)-2-methoxyiminoacetamido]-3-[4-(3, 4-dihydroxyphenyl)-thiazol-2-yl]-thiomethyl-3-cephem-4-carboxylic acid

(38) 3-[4-(3,4-diacetoxyphenyl)thiazol-2-yl]thiomethyl-7β-[2-(2-aminothiazol-4-yl)-2-methoxyiminoacetamido]-3-cephem-4-carboxylic acid

(39) 7β-[2-(2-aminothiazol-4-yl)-2-isopropoxyiminoacetamido]-3-[4-(3, 4-dihydroxphenyl)-thiazol-2-yl]- thiomethyl-3-cephem-4-carboxylic acid

(40) 7β-[2-allyloxyimino-2-(2-aminothiazol-4-yl)acetamido]-3-[4-(3, 4-dihydroxyphenyl)thiazol-2-yl]-thiomethyl-3-cephem-4-carboxylic acid

(41) 7β-[2-(2-aminothiazol-4-yl)-2-(carboxymethoxyimino) acetamido]-3-[4-(3,4-dihydroxyphenyl)-thiazol-2-yl]thiomethyl-3-cephem-4-carboxylic acid

(42) 7β-[2-(2-aminothiazol-4-yl)-2-(1-carboxy-1-methylethoxyimino) acetamido]-3-[4-(3,4-dihydroxyphenyl)-thiazol-2-yl]thiomethyl-3-cephem-4-carboxylic acid

(43) 7β-[2-(2-aminothiazol-4-yl)-2-(1-carboxy-1-cyclopropoxyimino) acetamido]-3-[4-(3,4-dihydroxyphenyl)-thiazol-2-yl]thiomethyl-3-cephem-4-carboxylic acid

(44) 7β-[2-(2-aminothiazol.-4-yl)-2-benzyloxyiminoacetamido]-3-[4-(3, 4-dihydroxyphenyl)-thiazol-2-yl]-thiomethyl-3-cephem-4-carboxylic acid

(45) 7β-[2-(2-aminothiazol-4-yl)-2-(3,4-dihydroxybenzyloxyimino) acetamido]-3-[4-(3,4-dihydroxyphenyl) thiazol-2-yl]thiomethyl-3-cephem-4-carboxylic acid

(46) 7β-[2-(2-aminothiazol-4-yl-2-methoxyiminoacetamido]-3-[4-(3, 4-dihydroxyphenyl)-thiazol-2-yl]-thiomethyl-3-cephem-4-carboxylic acid

(47) 3-[4-(3,4-diacetoxyphenyl)thiazol-2-yl]thiomethyl-7β-[2-(2-aminothiazol-4-yl)-2-ethoxyiminoacetamido]-3-cephem-4-carboxylic acid

(48) 7β-[2-(1-carboxy-1-methylethoxyimino)acetamido]-3[5-(3, 4-dihydroxyphenyl)4-carboxythiazol-2yl]-thiomethyl-3-cephem-4-carboxylic acid

(49) 7β-[2-(2-aminothiazol-4-yl)-2-(a-carboxybenzyloxyimino) acetamido]-3-[5-(3,4-dihydroxyphenyl)-4-carboxythiazol-2-yl]thiomethyl-3-cephem-4carboxylic acid

(50) 7β-[2-(2-aminothiazol-4-yl)-2-methoxyiminoacetamido]-3-[5-(3, 4-dihydroxyphenyl-4-carboxythiazol-2-yl]thiomethyl-3-cephem-4-carboxylic acid

(51) 7β-[2-(2-aminothiazol-4-yl)-2-ethoxyiminoacetamido]-3-[5-(3, 4-dihydroxyphenyl)-4-carboxythiazol-2-yl]-thiomethyl-3-cephem-4-carboxylic acid

(52) 7β-[2-(2-aminothiazol-4-yl)-2-cyclopentyloxyiminoacetamido]-3-[5-(3, 4-dihydroxyphenyl)-4-carboxythiazol-2-yl]thiomethyl-3-cephem-4-carboxylic acid

(53) 7β-[2-allyloxyimino-2-(2-aminothiazol-4-yl)acetamido]-3-[5-(3, 4-dihydroxyphenyl)-4-carboxythiazol-2-yl]thiomethyl-3-cephem-4-carboxylic acid

(54) 7β-[2-(2-aminothiazol-4-yl)-2-propargyloxyiminoacetamido]-3-[5-(3, 4-dihydroxyphenyl)-4-carboxythiazol-2-yl]thiomethyl-3-cephem-4-carboxylic acid

(55) 7β-[2-(2-aminothiazol-4-yl)-2-benzyloxyiminoacetamido]-3-[5-(3, 4-dihydroxyphenyl)-4-carboxythiazol-2-yl thiomethyl-3-cephem-4-carboxylic acid

(56) 7β-[2-(2-aminothiazol-4-yl)-2-methoxyiminoactamido]-3-[4-(3, 4-dihydroxyphenyl)-5-carboxymethylthiazol-2-yl]thiomethyl-3-cephem-4carboxylic acid

(57) 7β-[2-(2-aminothiazol-4yl)-2-(1-carboxy-1-methylethoxyimino) acetamido]-3-[4-(3,4-dihydroxyphenyl)-5-carboxymethylthiazol-2-yl]thiomethyl-3-cephem-4-carboxylic acid

(58) 3-[4-(3,4-diacetoxyphenyl)-5carboxymethylthiazol-2-yl]thiomethyl-7β-[2-(2-aminothiazol-4yl)-2-(1-carboxy-1-methylethoxyimino) acetamido]-3-cephem-4carboxylic acid

(59) 7β-[2-(2-aminothiazol-4yl)-2-(1-carboxy-1cyclopropoxyimino) acetamido]-3-[4-(3,4-dihydroxyphenyl)-5carboxymethylthiazol-2-yl]thiomethyl-3-cephem-4-carboxylic acid

(60) 3-[4-(3,4-diacetoxyphenyl)-5-carboxymethylthiazol-2-yl]thiomethyl-7β-[2(2-aminothiazol-4yl)-2-(1-carboxy-1-cyclopropoxyimino) acetamido]-3-cephem-4-carboxylic acid

(61) 3-[4-(3,4-diacetoxyphenyl)-5carboxymethylthiazol-2-yl]thiomethyl-7β-[2-(2-aminothiazol-4-yl)-2-(α-carboxybenzyloxyimino) acetamido]-3-cephem-4-carboxlic acid

(62) 7β-[2-(2-aminothiazol-4yl)-2-methoxyiminoacetamido]-3-[5-(3, 4-dihydroxyphenyl)oxazol-2yl]-thiomethyl-3-cephem-4carboxylic acid

(63) 7β-[2-(2-aminothiazol-4-yl)-2-ethoxyiminoacetamido]-3-[5-(3, 4-dihydroxyphenyl)oxazol-2yl]thiomethyl-3cephem-4carboxylic acid

(64) 7β-[2-(2aminothiazol-4yl)-2-(1-carboxy-1methylethoxyimino) acetamido]-3-[5-(3,4-dihydroxyphenyl)-oxazol-2-yl]thiomethyl-3-cephem-4-carboxylic acid

(65) 7β-{2-(2-aminothiazol-4-yl)-2-[(α-carboxy-3,4dihydroxybenzyl) oxyimino]acetamido}-3-[5-(3,4-dihydroxyphenyl) oxazol-2-yl]thiomethyl-3-cephem-4carboxylic acid

(66) 7β-[2-(2-aminothiazol-4-yl)-2-(1-carboxy-1-cyclopropoxyimino) acetamido]-3-[5-(3,4-dihydroxyphenyl)oxazol-2-yl]thiomethyl-3-cephem-4-carboxylic acid

(67) 3-[5-(3,4-diacetoxyphenyl)oxazol-2-yl]thiomethyl-7β-[2-(2-aminothiazol-4-yl)-2-ethoxyiminoacetamido]-3-cephem-4-carboxylic acid

(68) 78-[2-(2-aminothiazol-4-yl)-2-methoxyiminoacetamido]-3-(5, 6-dihydroxybenzimidazol-2-yl)thiomethyl-3-cephem-4-carboxylic acid 4. The antibacterial agent according to claim 2, which is effective against glucose non-fermentative Gram-negative rods.

5. The antibacterial agent according to claim 2 which is effective against pseudomonads.

6. A method of treating infectious disease which comprises administering to a human or animal an antibacterially effective amount of the compound according to claim 1, as an antibacterial agent.

7. The treatment according to claim 6 wherein the compound is used as the antibacterial agent against glucose non-fermentative Gram-negative rods.

8. The treatment according to claim 6 wherein the compound is used as the antibacterial agent against pseudomonads.

* * * * *